(12) United States Patent
Hoye et al.

(10) Patent No.: US 10,047,100 B2
(45) Date of Patent: Aug. 14, 2018

(54) COMPOUNDS FROM RENEWABLE RESOURCES

(71) Applicant: REGENTS OF THE UNIVERSITY OF MINNESOTA, Minneapolis, MN (US)

(72) Inventors: Thomas R. Hoye, Minneapolis, MN (US); Ashok Pehere, Minneapolis, MN (US); Shu Xu, Minneapolis, MN (US)

( * ) Notice: Subject to any disclaimer, the term of this patent is extended or adjusted under 35 U.S.C. 154(b) by 0 days.

(21) Appl. No.: 15/474,401

(22) Filed: Mar. 30, 2017

(65) Prior Publication Data

US 2017/0291906 A1    Oct. 12, 2017

Related U.S. Application Data

(60) Provisional application No. 62/320,087, filed on Apr. 8, 2016.

(51) Int. Cl.
| | |
|---|---|
| *C07D 493/18* | (2006.01) |
| *C07C 1/213* | (2006.01) |
| *C07D 493/04* | (2006.01) |
| *C08F 124/00* | (2006.01) |
| *C07D 493/08* | (2006.01) |

(52) U.S. Cl.
CPC ............ *C07D 493/18* (2013.01); *C07C 1/213* (2013.01); *C07D 493/04* (2013.01); *C07D 493/08* (2013.01); *C08F 124/00* (2013.01)

(58) Field of Classification Search
CPC .. C07D 493/18; C07D 493/04; C07D 493/08; C07C 1/213; C08F 124/00
See application file for complete search history.

(56) References Cited

U.S. PATENT DOCUMENTS 5,084,539 A * 1/1992 Feast ...................... C08G 61/12
526/268

OTHER PUBLICATIONS

Adams, et al., "Furfural", Organic Syntheses vol. 1, 49 (1921).
Cai, et al., "Integrated furfural production as a renewable fuel and chemical platform from lignocellulosic biomass", J Chem Technol Biotechnol 89, 2-10 (2014).
Kaufmann, et al., "The use of platinum oxide as a catalyst in the reduction of organic compounds. IV. Reduction of furfural and its derivatives", J Am Chem Soc 45, 3029-3044 (1923).

(Continued)

*Primary Examiner* — Ling Choi
*Assistant Examiner* — David L Miller
(74) *Attorney, Agent, or Firm* — Viksnins Harris Padys Malen LLP

(57) ABSTRACT

Compounds of formula III:

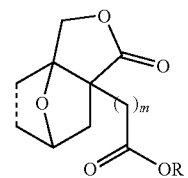

and salts thereof are disclosed. Also disclosed are methods for preparing compounds of formula III, intermediates useful for preparing compounds of formula III and methods for preparing compounds and materials from compounds of formula III.

19 Claims, 22 Drawing Sheets

(56) References Cited

OTHER PUBLICATIONS

Mahmoud, et al., "Renewable production of phthalic anhydride from biomass-derived furan and maleic anhydride", Green Chem 16, 167-175 (2014).
Medway, "Heterocycle construction using the biomass-derived building block itaconic acid", Green Chem 16, 2084-2101 (2014).
Pehere, et al., "Diels-Alder Reactions of Furans with Itaconic Anhydride: Overcoming Unfavorable Thermodynamics", Org Lett 18(11), 2584-2587 (2016).
Ritter, "Biomass or Bust Technology to use plant-derived sugars to produce chemical feedstocks is ready . . . and waiting", Chem Eng News 82(22), 31-33 (2004).
Werpy, et al., "Top Value Added Chemicals from Biomass vol. I—Results of Screening for Potential Candidates from Sugars and Synthesis Gas", Werpy et al., US Department of Energy, 2004; nrel.gov/docs/fy04osti/35523.pdf (accessed Jan. 15, 2016).

\* cited by examiner

Figure 3
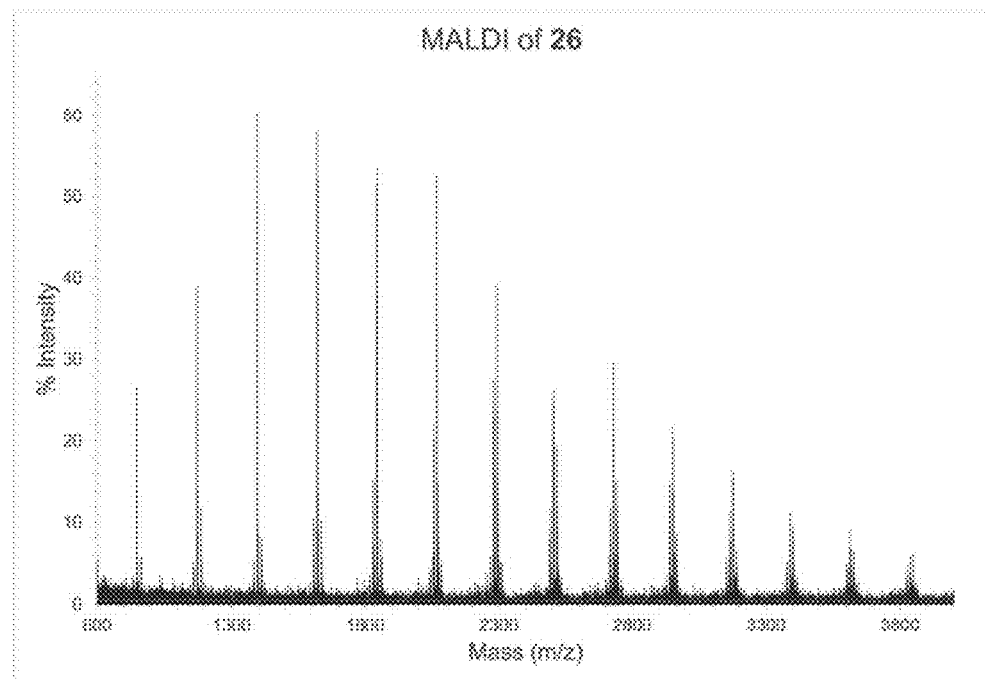
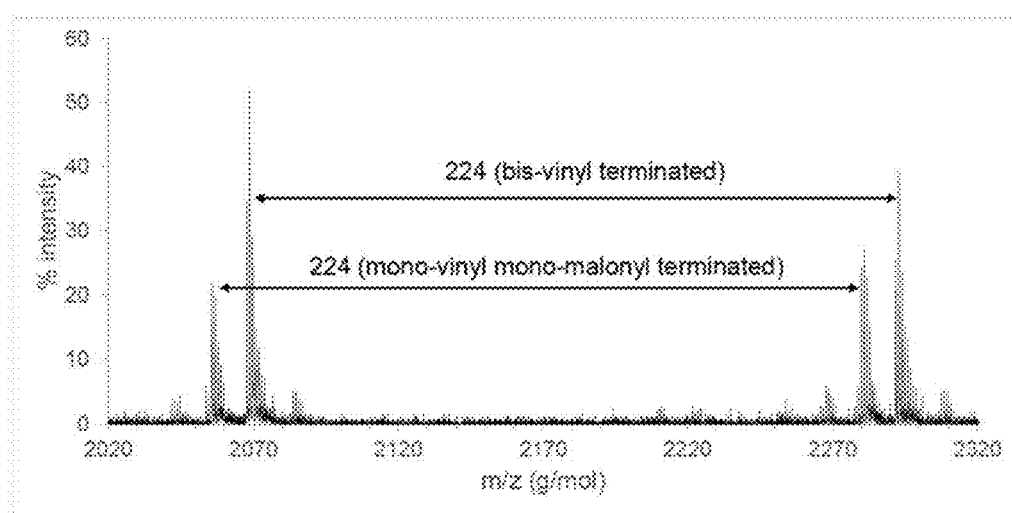

Figure 11A

CMAE of exp vs. DFT $^1$H data

|  | 4-exo$_{DFT}$ | 4-endo$_{DFT}$ |
|---|---|---|
| 4-exo$_{exp}$ | 0.14 | 0.35 |
| 4-endo$_{exp}$ | 0.24 | 0.08 |

Figure 11B

CMAE of exp vs. DFT $^{13}$C data

|  | 4-exo$_{DFT}$ | 4-endo$_{DFT}$ |
|---|---|---|
| 4-exo$_{exp}$ | 2.5 | 2.7 |
| 4-endo$_{exp}$ | 1.6 | 0.7 |

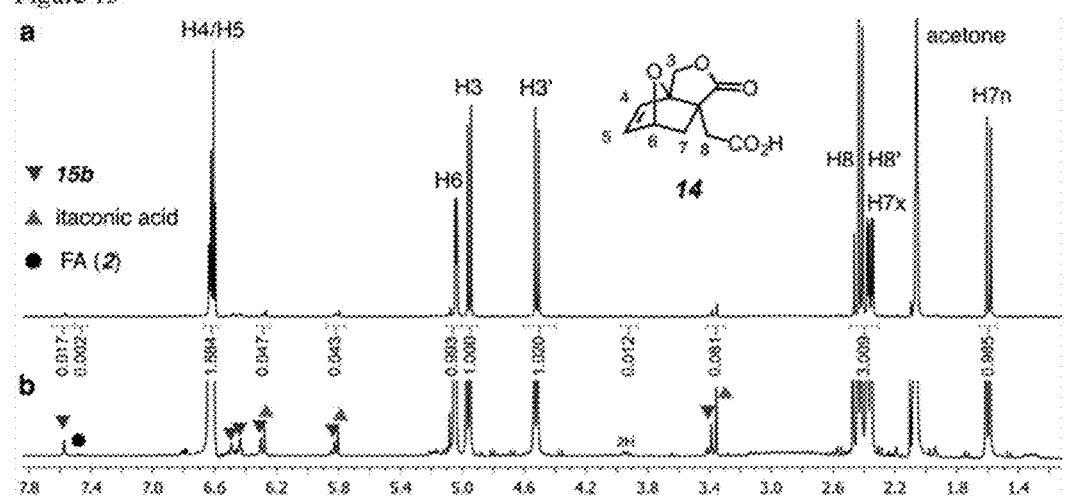

Condition: 1 mol% raft agent, 0.3 mol% AIBN, 95 °C

300

COMPOUNDS FROM RENEWABLE RESOURCES

CROSS-REFERENCE TO RELATED APPLICATIONS

This application claims priority to U.S. Provisional Application No. 62/320,087 that was filed on Apr. 8, 2016. The entire content of the application referenced above is hereby incorporated by referenced herein.

BACKGROUND

Itaconic acid (or itaconate, depending on its prevailing ionization state; Medway, A. M., Sperry, *Green Chem.* 2014, 16, 2084-2101) and furfural (Cai, C. M., et al., *J. Chem. Technol. Biotechnol.* 2014, 89, 2-10) are two chemicals abundantly available from biomass. They are prominent entries on master lists of privileged compounds for potential use in preparing bio-sourced/sustainable/renewable polymers and materials (e.g., Ritter, S. K., Chem. *Eng. News* 2004, 82, 31-34; Top value added chemicals from biomass, Volume I-Results of screening for potential candidates from sugars and synthesis gas. eds. Werpy T., Petersen, G., US Department of Energy, 2004. nrel.gov/docs/fy04osti/35523.pdf (accessed Jan. 15, 2016)). The first arises by metabolic pathways as textbook as the citric acid (also known as the tricarboxylic or Krebs) cycle; the second by acid-catalyzed dehydration of 5-carbon sugars prevalent in, for example, corncobs (Adams, R., Voorhees, V., *Organic Syntheses*, Vol. 1, 1921, 49) and oat husks. For a century it has been known that each of itaconic anhydride (1, IA) and furfuryl alcohol (2, FA) is readily available by simple conversions such as dehydration (Fittig R., et al., *J. Liebigs Ann. Chem.* 1904, 331, 151-196) and reduction (Kaufmann W. E., Adams, R., *J. Am. Chem. Soc.* 1923, 45, 3029-3044) of these abundantly available precursors (Scheme 1).

The Diels-Alder (DA) [4+2] cycloaddition reaction to produce cyclohexene derivatives is among the most iconic of all reactions in organic chemistry. The ability of IA to function as a dienophile, the $2\pi$-component, to engage various dienes was, in fact, described in the ground-breaking first publication by Diels and Alder (Diels O., Alder K., *J. Liebigs Ann. der Chem.* 1928, 460, 98-122). The use of furan as a diene, the $4\pi$-component, was reported one year later in their second paper on the subject of "hydroaromatic synthesis" (Diels O., K., *Ber. Dtsch. Chem. Ges.* 1929, 62, 554-562). It appears that there have been no reports regarding the reaction of IA (1) or itaconic acid (or its esters) with any furan derivative in the intervening >85 years. A recent study of the DA reactions of 2-methyl- and 2,5-dimethylfuran with maleic anhydride, a more reactive, bio-derivable anhydride, has been reported (Mahmoud E., et al., *Green Chem.* 2014, 16, 167-175).

There is a continually growing interest in sourcing organic compounds from renewable resources. Compounds from renewable resources may be useful as such, or these compounds may be useful as intermediates to prepare other compounds or materials such as bio-sourced materials (e.g., polymers). The vast majority of plastics commonly used today (e.g., polyethylene and polystyrene) are produced from crude oil (petroleum) and natural gas. These plastics are widely used in applications ranging from automotive, packaging, adhesive, and construction materials.

However, because they are derived from non-renewable feedstocks, these are, necessarily, unsustainable materials. Alternatively, polymeric materials derived from renewable raw materials (e.g., sugars, cellulosics, vegetable oil, and terpenes) that have comparable properties to those of petroleum-derived polymers and plastics have the potential to meet the needs (and desires) of humans while having zero net impact on the earth's environment. Bio-soured plastics could find utility in essentially all of the myriad applications of today's plastics. Common chemical classes of polymers that can be bio-sourced include polyolefins, polyesters, polyamides, polyurethanes, and polycarbonates. Sustainable polymers or "green materials" can be both durable and Scheme 1

Itaconic anhydride (IA, 1) and furfuryl alcohol (FA, 2) are abundantly available for biomass.

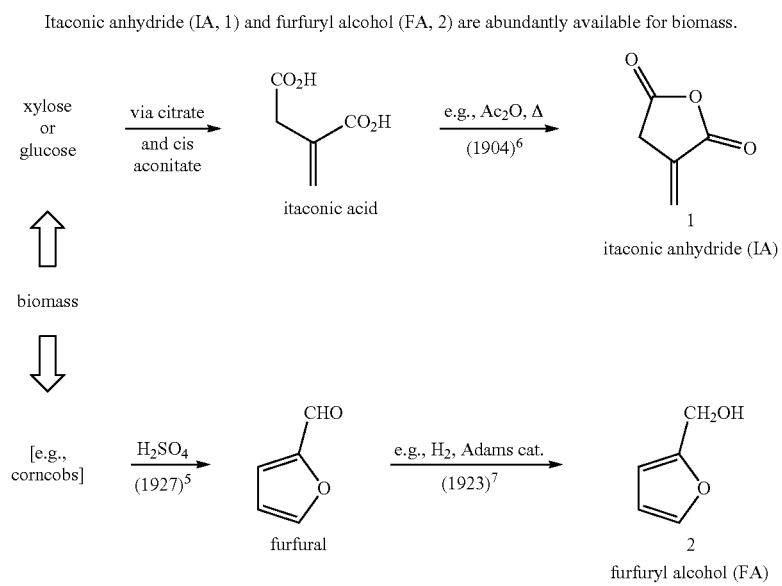

degradable, they can be used in applications ranging from adhesives to packaging to clothing to building materials, and they can, in principle, be produced both economically and with minimal environmental impact.

SUMMARY OF INVENTION

One embodiment provides a compound of formula I or a salt thereof, or a compound of formula II or an enantiomer thereof:

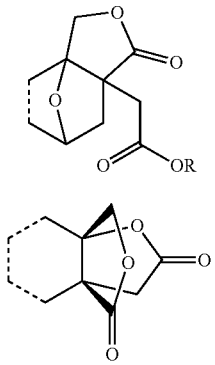

wherein R is H, $(C_1$-$C_6)$alkyl, or $(C_3$-$C_6)$cycloalkyl and each dashed bond is a single bond or double bond provided no two double bonds of the compound of formula II are cumulated.

One embodiment provides a compound of formula III or a salt thereof:

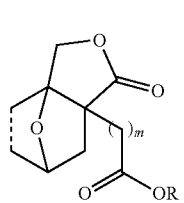

wherein: m is 1 or 2; R is H, $(C_1$-$C_6)$alkyl, or $(C_3$-$C_6)$cycloalkyl; and the dashed bond is a single bond or double bond.

One embodiment provides a method for preparing a compound of formula Ic1:

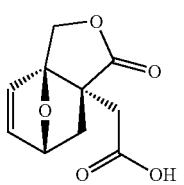

or a salt thereof or an enantiomer or a salt thereof, comprising converting furfuryl alcohol to the compound of formula Ic1 or a salt thereof or an enantiomer or a salt thereof.

One embodiment provides a method for preparing a compound of formula Ic1:

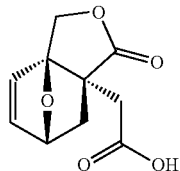

or a salt thereof or an enantiomer or a salt thereof, comprising converting itaconic anhydride to the compound of formula Ic1 or a salt thereof or an enantiomer or a salt thereof.

One embodiment provides a method for preparing a compound of formula Ic1:

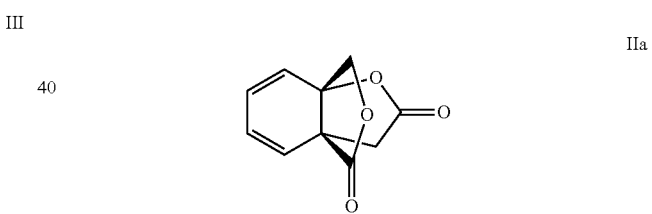

or a salt thereof or an enantiomer or a salt thereof, comprising contacting furfuryl alcohol with itaconic anhydride to provide the compound of formula Ic1 or a salt thereof or an enantiomer or a salt thereof.

One embodiment provides a method for preparing a compound of formula IIa:

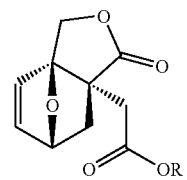

or enantiomer thereof comprising converting a compound of formula Ic:

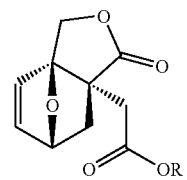

or a salt thereof or an enantiomer or a salt thereof to the compound of formula IIa wherein R is H, $(C_1$-$C_6)$alkyl, or $(C_3$-$C_6)$cycloalkyl.

One embodiment provides a method for preparing a compound of formula 18:

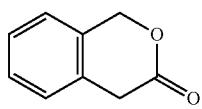

comprising converting a compound of formula Ic:

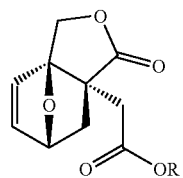
Ic or a salt thereof or an enantiomer or a salt thereof to the compound of formula 18, wherein R is H, $(C_1-C_6)$alkyl, or $(C_3-C_6)$cycloalkyl.

One embodiment provides a method for preparing a compound of formula 18:

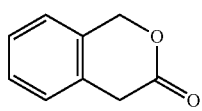
18 comprising converting a compound of formula IIa:

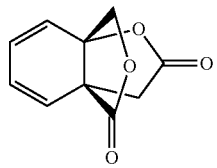
IIa or an enantiomer thereof to the compound of formula 18.

One embodiment provides a method for preparing a compound of formula 23:

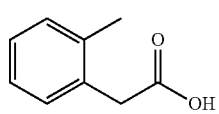
23 or a salt thereof, comprising converting a compound of formula Id:

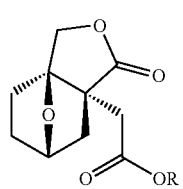
Id or a salt thereof or an enantiomer or a salt thereof to the compound of formula 23, wherein R is H, $(C_1-C_6)$alkyl, or $(C_3-C_6)$cycloalkyl.

One embodiment provides a polymer comprising two or more residues of formula 26:

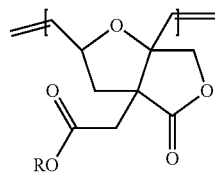
26 or a salt thereof, wherein R is H, $(C_1-C_6)$alkyl, or $(C_3-C_6)$cycloalkyl.

One embodiment provides a method for preparing a polymer comprising two or more residues of formula 26:

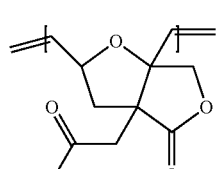
26 or a salt thereof, comprising polymerizing a compound of formula I:

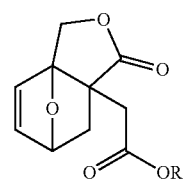
I or a salt thereof, wherein R is H, $(C_1-C_6)$alkyl, or $(C_3-C_6)$cycloalkyl.

One embodiment provides a method for preparing a polymer comprising two or more residues of formula 26a:

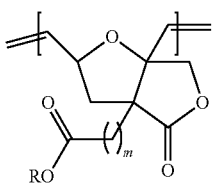
26a wherein: m is 1 or 2; and R is H, $(C_1-C_6)$alkyl, or $(C_3-C_6)$cycloalkyl; or a salt thereof, comprising polymerizing a corresponding compound of formula III:

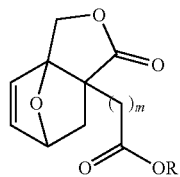

IIIa wherein: m is 1 or 2; R is H, $(C_1-C_6)$alkyl, or $(C_3-C_6)$cycloalkyl.

One embodiment provides a method for preparing a compound of formula IIIc1:

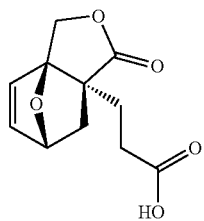

IIIc1 or a salt thereof or an enantiomer or a salt thereof, comprising converting furfuryl alcohol to the compound of formula IIIc1 or a salt thereof or an enantiomer or a salt thereof.

One embodiment provides processes and intermediates disclosed herein that are useful for preparing a compound of formula I or useful for preparing compounds from a compound of formula I.

BRIEF DESCRIPTION OF FIGURES

FIG. 3 shows the MALDI mass spectrum of 26, entry 1 (Table 1).

FIGS. 11A and 11B show the CMAEs for $^1$H (11A) and $^{13}$C (11B) computed chemical shifts between matched and unmatched 4-exo and 4-endo.

FIG. 13 shows the 1H NMR spectrum in acetone-d6 of an aliquot of the bulk reaction mixture from 1:1 IA (1) and FA (2). For spectrum A the resonances from the major product 14 are assigned. For spectrum b the vertical scale has been increased 5× and the principal minor components are denoted. Integration of all minor components indicates a 94% yield of 14.

DETAILED DESCRIPTION

Figure 1:
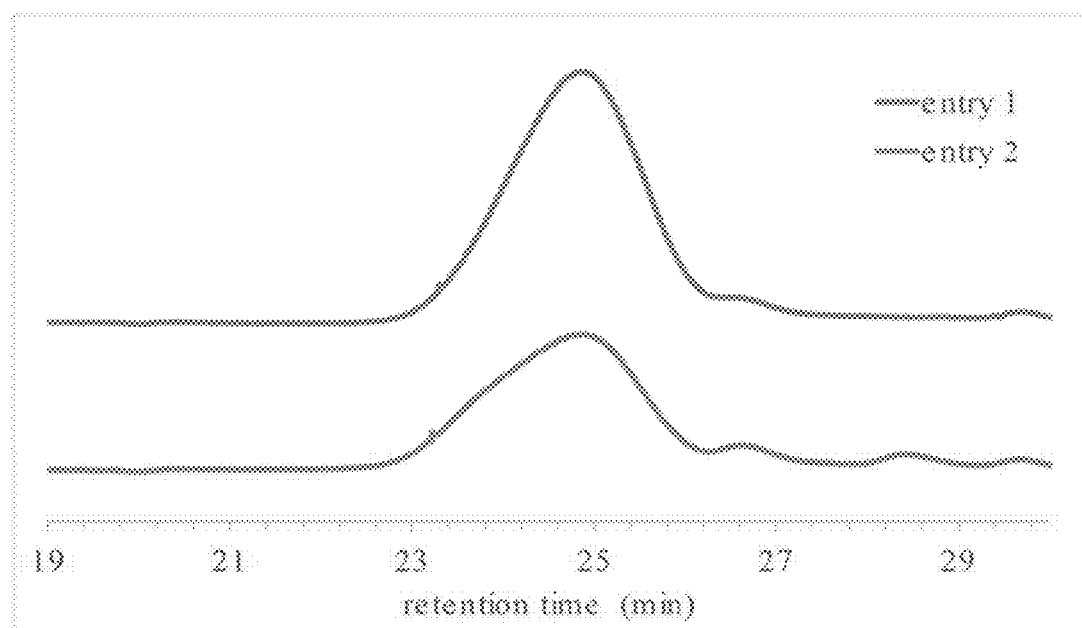
FIG. 1 shows the GPC chromatograms of 26, entries 1 and 2 (Table 1).
Figure 2:
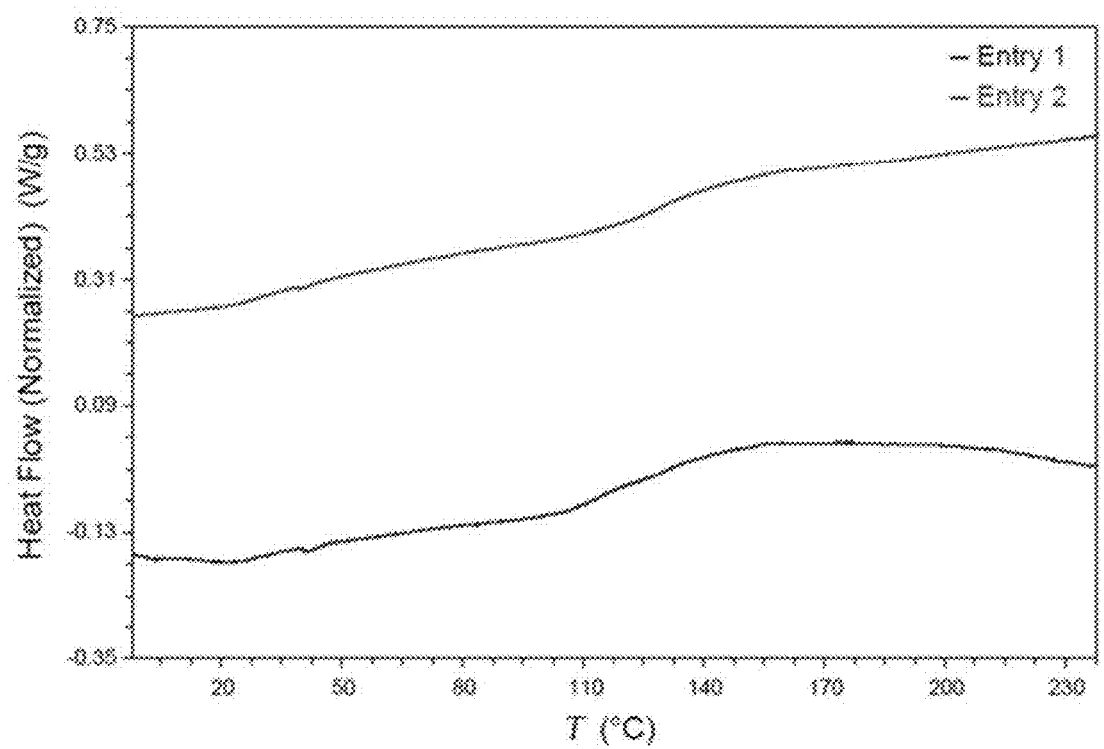
FIG. 2 shows the DSC heating curves of 26, entries 1 and 2 (Table 1); data shown are for the second heating cycle (10° C.·min$^{-1}$).
Figure 4:
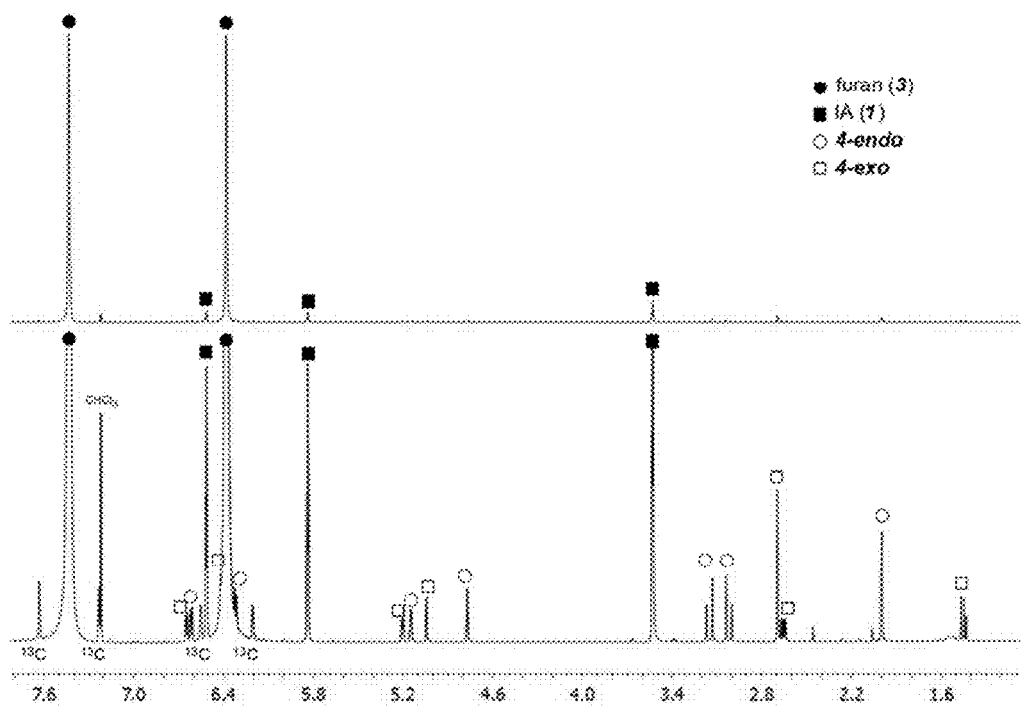
FIG. 4 shows the equilibrium state $^1$H NMR spectrum for formation of 4-endo and 4-exo.
Figure 5:
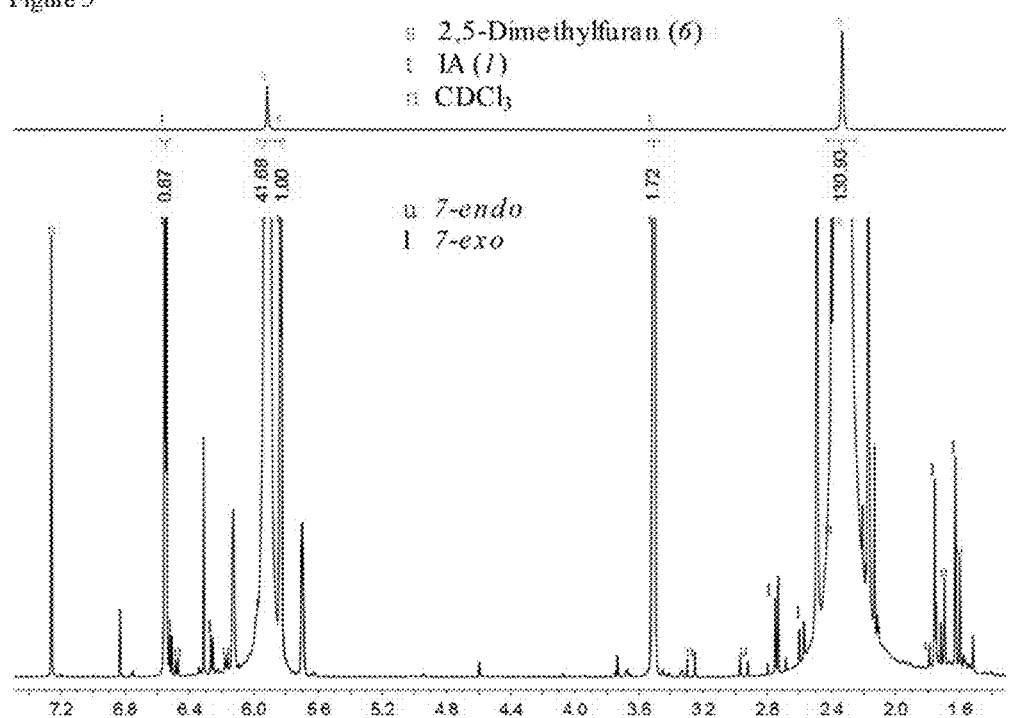
FIG. 5 shows the equilibrium state $^1$H NMR spectrum for formation of 7-endo and 7-exo.
Figure 6:
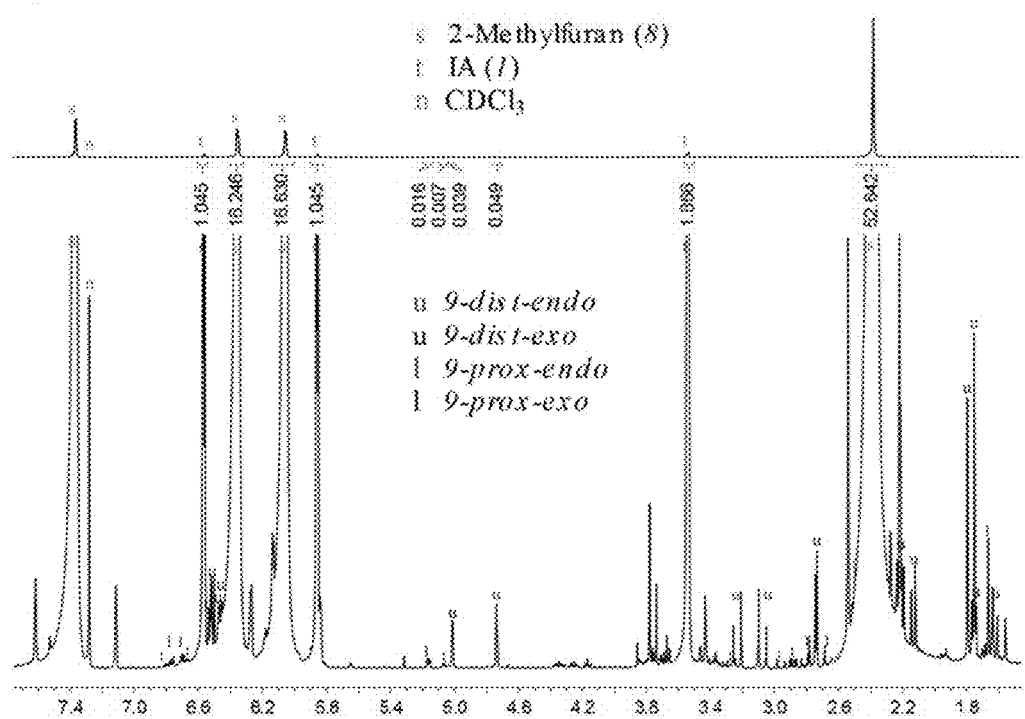
FIG. 6 shows the equilibrium state $^1$H NMR spectrum for formation of 9-dist-endo, 9-dist-exo, 9-prox-endo, and 9-prox-exo.
Figure 7:
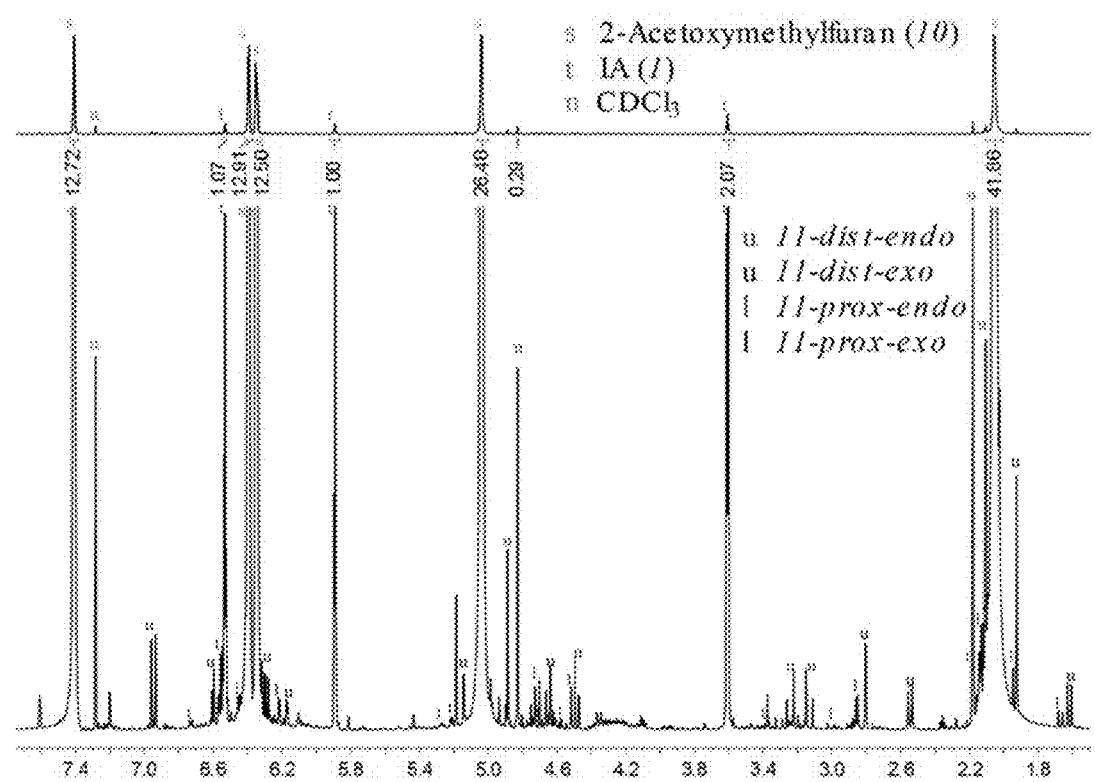
FIG. 7 shows the equilibrium state $^1$H NMR spectrum for formation of 11-dist-endo, 11-dist-exo, 11-prox-endo, and 11-prox-exo.
Figure 8:
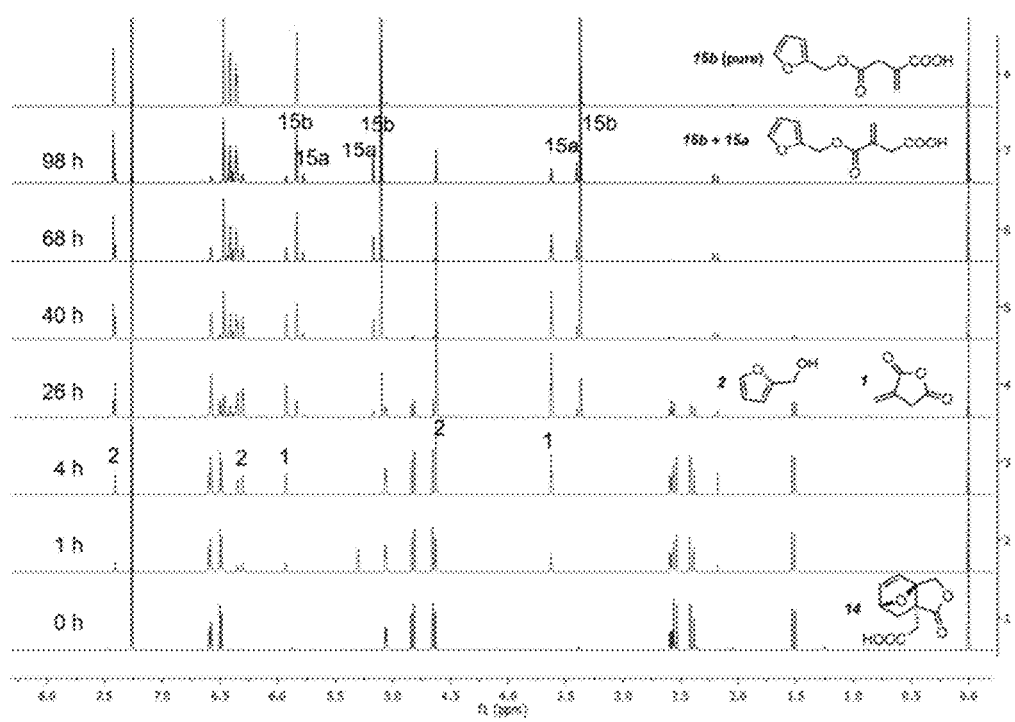
FIG. 8 shows the in situ $^1$H NMR monitoring of the reaction of 14 in CDCl$_3$ to produce 15a and 15b via 1 and 2 (and, presumably, 12-prox-exo).

Described herein is the discovery of highly versatile organic compounds (e.g., compounds of formula I) that are sourced from renewable resources. Also described herein are methods to prepare such compounds (e.g., compounds of formula I) and methods to prepare other compounds and materials from such compounds.

The following definitions are used, unless otherwise described.

The term "alkyl" refers to a straight or branched saturated hydrocarbon. For example, an alkyl group can have 1 to 8 carbon atoms (i.e., $(C_1-C_8)$alkyl) or 1 to 6 carbon atoms (i.e., $(C_1-C_6$ alkyl).

The term "cycloalkyl" refers to a cyclic saturated hydrocarbon. For example, $(C_3-C_6)$cycloalkyl can have 3 to 6 cyclic carbon atoms.

The term "cumulated" as used herein refers to carbon-carbon double bonds that share a carbon atom.

It will be appreciated by those skilled in the art that compounds of the invention having one or more chiral centers may exist in and be isolated for example in optically active and racemic forms. Some compounds may exhibit polymorphism. It is to be understood that the present invention encompasses any racemic, optically-active, polymorphic, or stereoisomeric form, or mixtures thereof, of a compound of the invention that possess the useful properties described herein, it being well known in the art how to prepare optically active forms (for example, by resolution of the racemic form by recrystallization techniques, by synthesis from optically-active starting materials, by enantioselective synthesis methods (including asymmetric catalysis), or by chromatographic separation using a chiral stationary phase.

When a bond in a compound formula herein is drawn in a non-stereochemical manner (i.e., flat), the atom to which the bond is attached includes all stereochemical possibilities. When a bond in a compound formula herein is drawn in a defined stereochemical manner (i.e., bold, bold-wedge, dashed, or dashed-wedge), it is to be understood that the atom to which the stereochemical bond is attached is enriched in the absolute stereoisomer depicted unless otherwise noted. In one embodiment, the compound may be at least 51% the absolute stereoisomer depicted. In another embodiment, the compound may be at least 60% the absolute stereoisomer depicted. In another embodiment, the compound may be at least 80% the absolute stereoisomer depicted. In another embodiment, the compound may be at least 90% the absolute stereoisomer depicted. In another embodiment, the compound may be at least 95 the absolute stereoisomer depicted. In another embodiment, the compound may be at least 99% the absolute stereoisomer depicted.

It is to be understood that the term "and/or an enantiomer thereof" refers to the compound and the enantiomer. For example, the term "a compound of formula Ia or/and an enantiomer thereof":

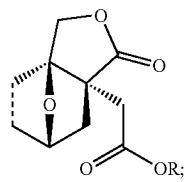

Ia refers to both the compound of formula Ia (as shown above) and its enantiomer (the compound of formula Ib):

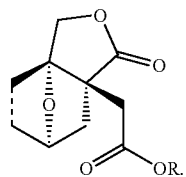

Ib

Specific embodiments listed below for radicals, substituents, and ranges, are for illustration only; they do not exclude other defined embodiments or values or other values within defined ranges for the radicals and substituents. It is to be understood that two or more embodiments may be combined. Specific embodiments listed below are embodiments for compounds of formula I and formula II as well as all related formulas (e.g., compounds of formulas Ia, Ib, Ic, Id, Ia1).

One embodiment provides a compound of formula Ia or a salt thereof or an enantiomer thereof or a salt thereof, or a compound of formula II or an enantiomer thereof:

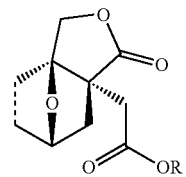

Ia

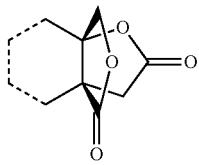

II wherein R is H, $(C_1-C_6)$alkyl, or $(C_3-C_6)$cycloalkyl and each dashed bond is a single bond or double bond provided no two double bonds of the compound of formula II are cumulated.

One embodiment provides a compound of formula Ia:

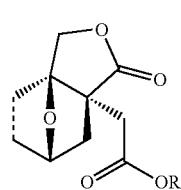

Ia or a salt thereof or an enantiomer or a salt thereof, wherein R is H, $(C_1-C_6)$alkyl, or $(C_3-C_6)$cycloalkyl.

One embodiment provides a compound of formula Ic or Id:

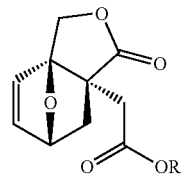

Ic

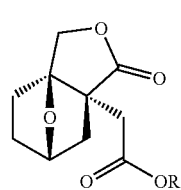

Id or a salt thereof or an enantiomer or a salt thereof, wherein R is H, $(C_1-C_6)$alkyl, or $(C_3-C_6)$cycloalkyl.

One embodiment provides a compound of formula Ic or Id:

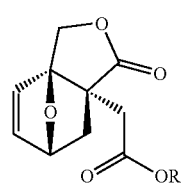

Ic

-continued
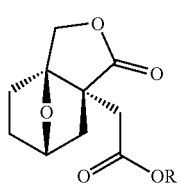
Id
or an enantiomer thereof, wherein R is H, $(C_1-C_6)$alkyl, or $(C_3-C_6)$cycloalkyl.
One embodiment provides a compound of formula II:
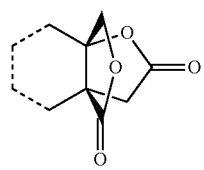
II
or an enantiomer thereof.
One embodiment provides a compound that is:
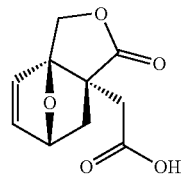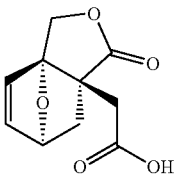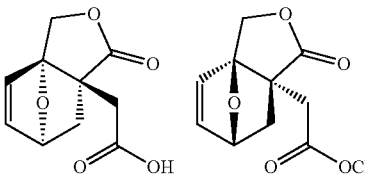
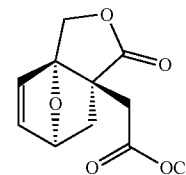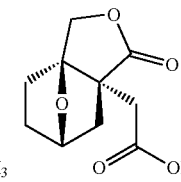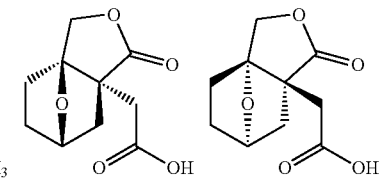
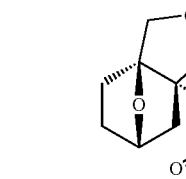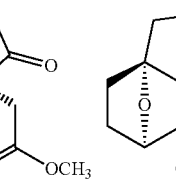
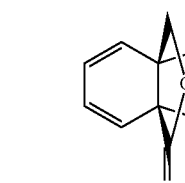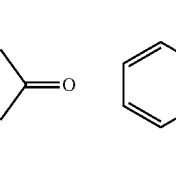
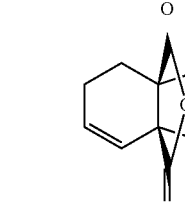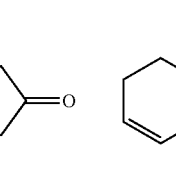
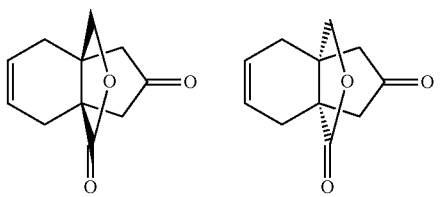
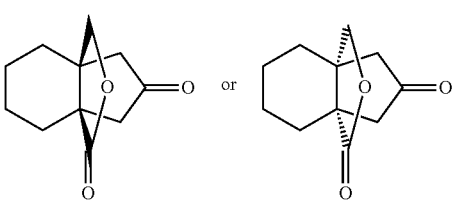
or a salt thereof.
One embodiment provides a compound that is:
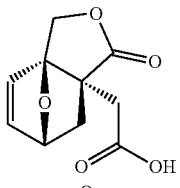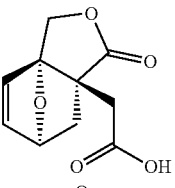
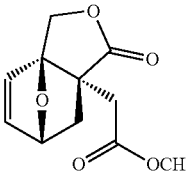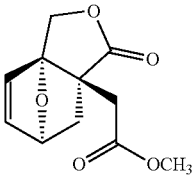
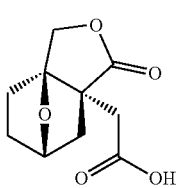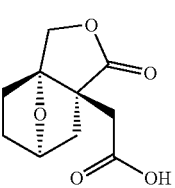
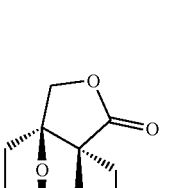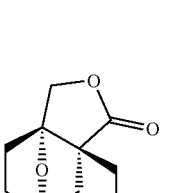
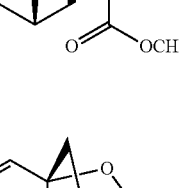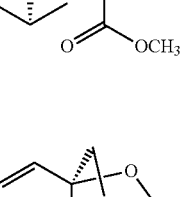
or a salt thereof.

One embodiment provides a compound that is:

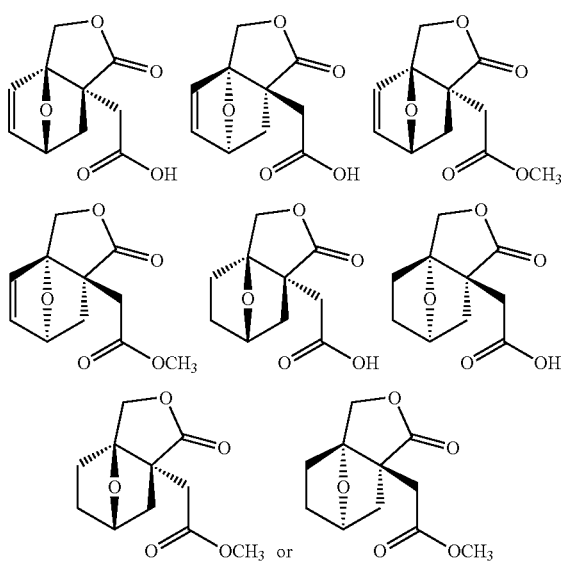

or a salt thereof.

One embodiment provides a compound that is:

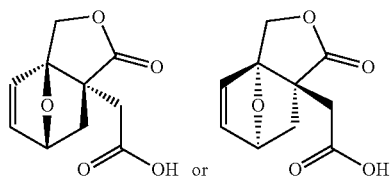 [SMILES: O=C(O)C[C@]12C[C@@H]3C=C[C@@]1(COC2=O)O3 ; O=C(O)C[C@@]12C[C@H]3C=C[C@]1(COC2=O)O3]

or a salt thereof.

One embodiment provides a compound that is:

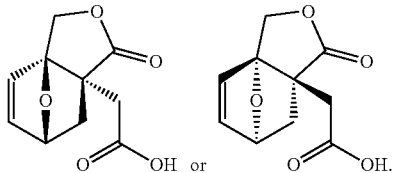 [SMILES: O=C(O)C[C@]12C[C@@H]3C=C[C@@]1(COC2=O)O3 ; O=C(O)C[C@@]12C[C@H]3C=C[C@]1(COC2=O)O3]

One embodiment provides a composition comprising:

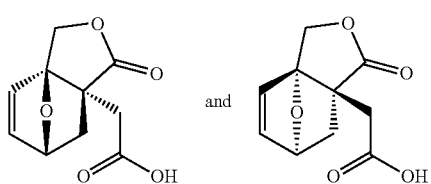 [SMILES: O=C(O)C[C@]12C[C@@H]3C=C[C@@]1(COC2=O)O3 ; O=C(O)C[C@@]12C[C@H]3C=C[C@]1(COC2=O)O3]

or salts thereof.

One embodiment provides a composition comprising:

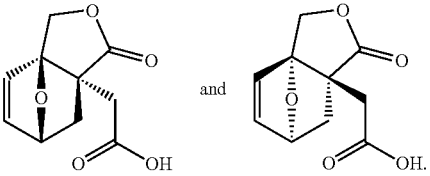 [SMILES: O=C(O)C[C@]12C[C@@H]3C=C[C@@]1(COC2=O)O3 ; O=C(O)C[C@@]12C[C@H]3C=C[C@]1(COC2=O)O3]

Methods for the Preparation of the Compound of Formula Ic1 and the Enantiomer Thereof.

The compound of formula Ic1 and the enantiomer thereof (Ic2), which compounds are also shown as compound 14 and the enantiomer thereof, may be prepared by contacting (i.e., reacting) furfuryl alcohol and itaconic anhydride as described in Example I.

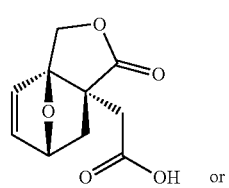

Ic1 or

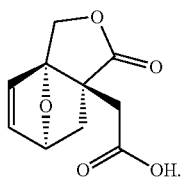

Ic2

The reaction of furfuryl alcohol and itaconic anhydride can be performed at a variety of temperatures including ambient temperature (room temperature such as about 20-25° C.). The reaction can be performed in the presence or absence of solvent. The ratio of reactants (ratio of furfuryl alcohol to itaconic) can also be varied.

Accordingly, one embodiment provides a method for preparing a compound of formula Ic1 or a salt thereof or an enantiomer or a salt thereof, comprising converting furfuryl alcohol to the compound of formula Ic1 or a salt thereof or the enantiomer or a salt thereof. Another embodiment provides a method for preparing a compound of formula Ic1 or a salt thereof or an enantiomer or a salt thereof, comprising converting itaconic anhydride to the compound of formula Ic1 or a salt thereof or the enantiomer or a salt thereof. Another embodiment provides a method for preparing a compound of formula Ic1 or a salt thereof or an enantiomer or a salt thereof, comprising contacting furfuryl alcohol with itaconic anhydride to provide the compound of formula Ic1 or a salt thereof or the enantiomer or a salt thereof.

In one embodiment the contacting is done at or about ambient temperature. In one embodiment the contacting is performed in the absence of solvent. In one embodiment the ratio of furfuryl alcohol to itaconic anhydride is about 1.5/1 to 2.5/1. In one embodiment the ratio of furfuryl alcohol to itaconic anhydride is about 2/1. One embodiment provides a method for preparing a composition comprising the compound of formula Ic1 or a salt thereof and the enantiomer of the compound of formula Ic1 or a salt thereof.

One embodiment provides a method for preparing a preparing a composition comprising a compound of formula Ic1 and a compound of formula Ic2:

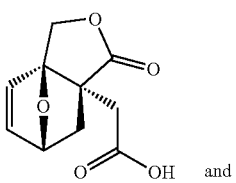

Ic1

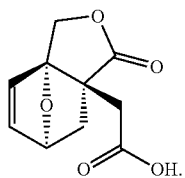

Ic2

One embodiment provides a compound as provided herein. One embodiment provides a compound as shown in Scheme 2A.

The compound of formula Ic1 and the enantiomer thereof may be converted to other compounds that have utility, for example as monomers or intermediates to prepare monomers, which monomers may be used to prepare useful polymers. Accordingly, certain embodiments provide methods to prepare compounds including but not limited to compounds of formula 17, 18, 20, 21, 22, 23, and 24 and enantiomers thereof. Certain compounds prepared from the compound of formula Ic1 and the enantiomer thereof are novel. For example, certain embodiments provide a compound of formula 17, 20, 21 and 22 and enantiomer thereof.

In one embodiment the invention provides a polymer having a backbone that comprises one or more groups of the following formula in the backbone:

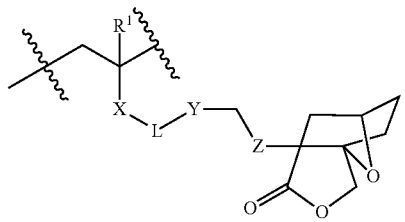

wherein:

each $R^1$ is independently H or $(C_1-C_6)$ alkyl;

each X is independently absent or is —C(=O)—;

each Y is independently absent or is —C(=O)—;

each Z is absent or is $CH_2$; and each L is independently a divalent, branched or unbranched, saturated or unsaturated, hydrocarbon chain, having from 2 to 10 carbon atoms, wherein one or more (e.g. 1, 2, 3, or 4) of the carbon atoms is optionally replaced by (—O—), and wherein the chain is optionally substituted on carbon with one or more (e.g. 1, 2, 3, or 4) substituents selected from $(C_1-C_6)$alkoxy, halo, and oxo (=O).

In one embodiment the invention provides a polymer that comprises at least two repeating units of the following formula:

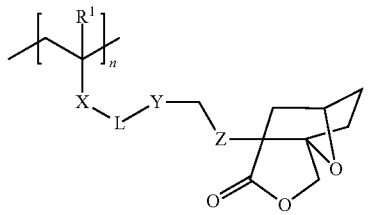

wherein:

each $R^1$ is independently H or $(C_1-C_6)$ alkyl;

each X is independently absent or is —C(=O)—;

each Y is independently absent or is —C(=O)—;

each Z is absent or is $CH_2$; and each L is independently a divalent, branched or unbranched, saturated or unsaturated, hydrocarbon chain, having from 2 to 10 carbon atoms, wherein one or more (e.g. 1, 2, 3, or 4) of the carbon atoms is optionally replaced by (—O—), and wherein the chain is optionally substituted on carbon with one or more (e.g. 1, 2, 3, or 4) substituents selected from $(C_1-C_6)$alkoxy, halo, and oxo (=O).

In one embodiment the invention provides a polymer that has the following formula:

[structure with subscript $n$]

wherein:

n is an integer from 3 to 200, inclusive;

each $R^1$ is independently H or $(C_1-C_6)$ alkyl;

each X is independently absent or is —C(=O)—;

each Y is independently absent or is —C(=O)—;

each Z is absent or is $CH_2$; and each L is independently a divalent, branched or unbranched, saturated or unsaturated, hydrocarbon chain, having from 2 to 10 carbon atoms, wherein one or more (e.g. 1, 2, 3, or 4) of the carbon atoms is optionally replaced by (—O—), and wherein the chain is optionally substituted on carbon with one or more (e.g. 1, 2, 3, or 4) substituents selected from $(C_1-C_6)$alkoxy, halo, and oxo (=O).

In one embodiment the invention provides a polymer having a backbone that comprises one or more groups of the following formula in the backbone:

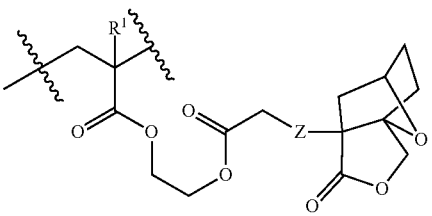

wherein each $R^1$ is independently H or methyl; and each Z is absent or is $CH_2$.

In one embodiment the invention provides a method comprising, polymerizing the compound:

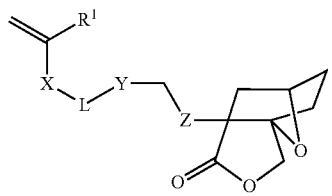

wherein:
R$^1$ is H or (C$_1$-C$_6$) alkyl;
X is absent or is —C(=O)—;
Y is absent or is —C(=O)—;
each Z is absent or is CH$_2$; and
L is a divalent, branched or unbranched, saturated or unsaturated, hydrocarbon chain, having from 2 to 10 carbon atoms, wherein one or more (e.g. 1, 2, 3, or 4) of the carbon atoms is optionally replaced by (—O—), and wherein the chain is optionally substituted on carbon with one or more (e.g. 1, 2, 3, or 4) substituents selected from (C$_1$-C$_6$)alkoxy, halo, and oxo (=O).

In one embodiment the invention provides a compound:

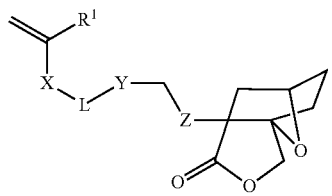

wherein:
R$^1$ is H or (C$_1$-C$_6$) alkyl;
X is absent or is —C(=O)—;
Y is absent or is —C(=O)—;
each Z is absent or is CH$_2$; and
L is a divalent, branched or unbranched, saturated or unsaturated, hydrocarbon chain, having from 2 to 10 carbon atoms, wherein one or more (e.g. 1, 2, 3, or 4) of the carbon atoms is optionally replaced by (—O—), and wherein the chain is optionally substituted on carbon with one or more (e.g. 1, 2, 3, or 4) substituents selected from (C$_1$-C$_6$)alkoxy, halo, and oxo (=O).

In one embodiment the invention provides a polymer having a backbone that comprises one or more groups of the following formula in the backbone:

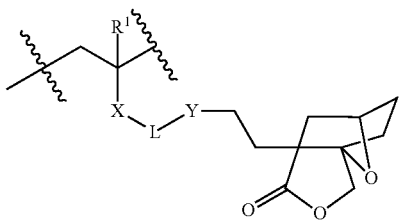

wherein:
each R$^1$ is independently H or (C$_1$-C$_6$) alkyl;
each X is independently absent or is —C(=O)—;
each Y is independently absent or is —C(=O)—; and
each L is independently a divalent, branched or unbranched, saturated or unsaturated, hydrocarbon chain, having from 2 to 10 carbon atoms, wherein one or more (e.g. 1, 2, 3, or 4) of the carbon atoms is optionally replaced by (—O—), and wherein the chain is optionally substituted on carbon with one or more (e.g. 1, 2, 3, or 4) substituents selected from (C$_1$-C$_6$)alkoxy, halo, and oxo (=O).

In one embodiment the invention provides a polymer that comprises at least two repeating units of the following formula:

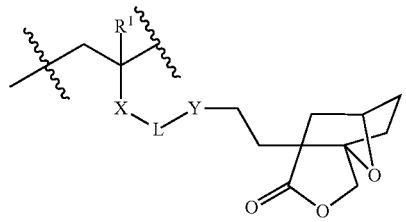

wherein:
each R$^1$ is independently H or (C$_1$-C$_6$) alkyl;
each X is independently absent or is —C(=O)—;
each Y is independently absent or is —C(=O)—; and
each L is independently a divalent, branched or unbranched, saturated or unsaturated, hydrocarbon chain, having from 2 to 10 carbon atoms, wherein one or more (e.g. 1, 2, 3, or 4) of the carbon atoms is optionally replaced by (—O—), and wherein the chain is optionally substituted on carbon with one or more (e.g. 1, 2, 3, or 4) substituents selected from (C$_1$-C$_6$)alkoxy, halo, and oxo (=O).

In one embodiment the invention provides a polymer that has the following formula:

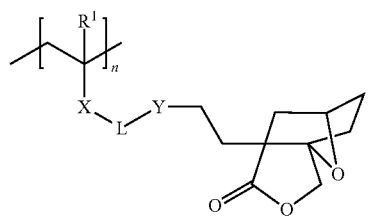

wherein:
n is an integer from 3 to 200, inclusive;
each R$^1$ is independently H or (C$_1$-C$_6$) alkyl;
each X is independently absent or is —C(=O)—;
each Y is independently absent or is —C(=O)—; and
each L is independently a divalent, branched or unbranched, saturated or unsaturated, hydrocarbon chain, having from 2 to 10 carbon atoms, wherein one or more (e.g. 1, 2, 3, or 4) of the carbon atoms is optionally replaced by (—O—), and wherein the chain is optionally substituted on carbon with one or more (e.g. 1, 2, 3, or 4) substituents selected from (C$_1$-C$_6$)alkoxy, halo, and oxo (=O).

In one embodiment the invention provides a polymer having a backbone that comprises one or more groups of the following formula in the backbone:

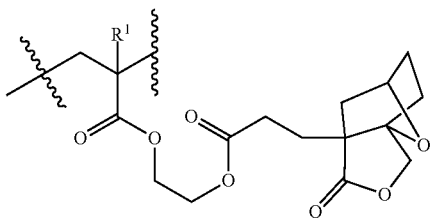

wherein each R¹ is independently H or methyl.

In one embodiment the invention provides a method comprising, polymerizing the compound:

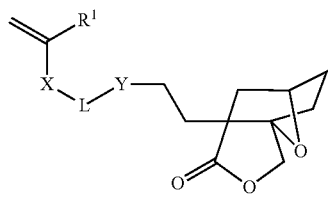

wherein:

R¹ is H or ($C_1$-$C_6$) alkyl;

X is absent or is —C(=O)—;

Y is absent or is —C(=O)—; and

L is a divalent, branched or unbranched, saturated or unsaturated, hydrocarbon chain, having from 2 to 10 carbon atoms, wherein one or more (e.g. 1, 2, 3, or 4) of the carbon atoms is optionally replaced by (—O—), and wherein the chain is optionally substituted on carbon with one or more (e.g. 1, 2, 3, or 4) substituents selected from ($C_1$-$C_6$)alkoxy, halo, and oxo (=O).

In one embodiment the invention provides a compound:

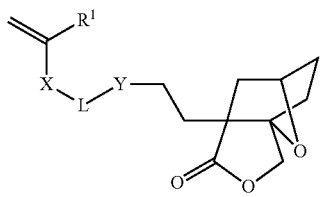

wherein:

R¹ is H or ($C_1$-$C_6$) alkyl;

X is absent or is —C(=O)—;

Y is absent or is —C(=O)—; and

L is a divalent, branched or unbranched, saturated or unsaturated, hydrocarbon chain, having from 2 to 10 carbon atoms, wherein one or more (e.g. 1, 2, 3, or 4) of the carbon atoms is optionally replaced by (—O—), and wherein the chain is optionally substituted on carbon with one or more (e.g. 1, 2, 3, or 4) substituents selected from ($C_1$-$C_6$)alkoxy, halo, and oxo (=O).

In one embodiment the invention provides a polymer having a backbone that comprises one or more groups of the following formula in the backbone:

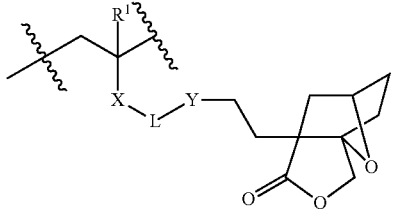

wherein:

each R¹ is independently H or ($C_1$-$C_6$) alkyl;

each X is independently absent or is —C(=O)—;

each Y is independently absent or is —C(=O)—; and each L is independently a divalent, branched or unbranched, saturated or unsaturated, hydrocarbon chain, having from 2 to 10 carbon atoms, wherein one or more (e.g. 1, 2, 3, or 4) of the carbon atoms is optionally replaced by (—O—), and wherein the chain is optionally substituted on carbon with one or more (e.g. 1, 2, 3, or 4) substituents selected from ($C_1$-$C_6$)alkoxy, halo, and oxo (=O).

In one embodiment the invention provides a polymer that comprises at least two repeating units of the following formula:

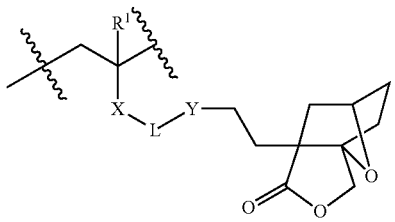

wherein:

each R¹ is independently H or ($C_1$-$C_6$) alkyl;

each X is independently absent or is —C(=O)—;

each Y is independently absent or is —C(=O)—; and each L is independently a divalent, branched or unbranched, saturated or unsaturated, hydrocarbon chain, having from 2 to 10 carbon atoms, wherein one or more (e.g. 1, 2, 3, or 4) of the carbon atoms is optionally replaced by (—O—), and wherein the chain is optionally substituted on carbon with one or more (e.g. 1, 2, 3, or 4) substituents selected from ($C_1$-$C_6$)alkoxy, halo, and oxo (=O).

In one embodiment the invention provides a polymer that has the following formula:

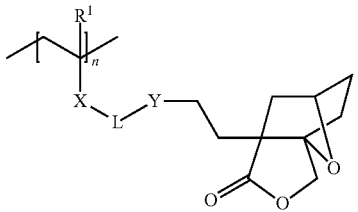

wherein:

n is an integer from 3 to 200, inclusive;

each R¹ is independently H or ($C_1$-$C_6$) alkyl;

each X is independently absent or is —C(=O)—;

each Y is independently absent or is —C(=O)—; and each L is independently a divalent, branched or unbranched, saturated or unsaturated, hydrocarbon chain, having from 2 to 10 carbon atoms, wherein one or more (e.g. 1, 2, 3, or 4) of the carbon atoms is optionally replaced by (—O—), and wherein the chain is optionally substituted on carbon with one or more (e.g. 1, 2, 3, or 4) substituents selected from ($C_1$-$C_6$)alkoxy, halo, and oxo (=O).

In one embodiment the invention provides a polymer having a backbone that comprises one or more groups of the following formula in the backbone:

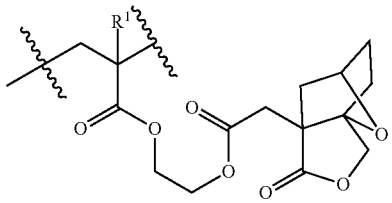

wherein each $R^1$ is independently H or methyl.

In one embodiment the invention provides a method comprising, polymerizing the compound:

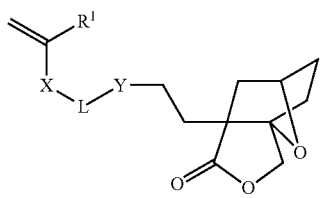

wherein:
$R^1$ is H or ($C_1$-$C_6$) alkyl;
X is absent or is —C(=O)—;
Y is absent or is —C(=O)—; and
L is a divalent, branched or unbranched, saturated or unsaturated, hydrocarbon chain, having from 2 to 10 carbon atoms, wherein one or more (e.g. 1, 2, 3, or 4) of the carbon atoms is optionally replaced by (—O—), and wherein the chain is optionally substituted on carbon with one or more (e.g. 1, 2, 3, or 4) substituents selected from ($C_1$-$C_6$)alkoxy, halo, and oxo (=O).

In one embodiment the invention provides a compound:

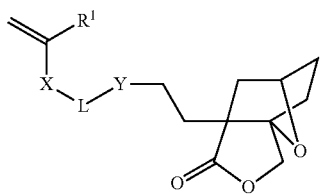

wherein:
$R^1$ is H or ($C_1$-$C_6$) alkyl;
X is absent or is —C(=O)—;
Y is absent or is —C(=O)—; and
L is a divalent, branched or unbranched, saturated or unsaturated, hydrocarbon chain, having from 2 to 10 carbon atoms, wherein one or more (e.g. 1, 2, 3, or 4) of the carbon atoms is optionally replaced by (—O—), and wherein the chain is optionally substituted on carbon with one or more (e.g. 1, 2, 3, or 4) substituents selected from ($C_1$-$C_6$)alkoxy, halo, and oxo (=O).

In one embodiment n is an integer from 3 to 100, inclusive.

In one embodiment n is an integer from 3 to 50, inclusive.

In one embodiment n is an integer from 3 to 25, inclusive.

In one embodiment each $R^1$ is independently H or methyl.

In one embodiment each X is —C(=O)—.

In one embodiment each X is absent.

In one embodiment each Y is —C(=O)—.

In one embodiment each Y is absent.

In one embodiment each L is a divalent, branched or unbranched, saturated or unsaturated, hydrocarbon chain, having from 2 to 10 carbon atoms, wherein one or more (e.g. 1, 2, 3, or 4) of the carbon atoms is optionally replaced by (—O—), and wherein the chain is optionally substituted on carbon with one or more (e.g. 1, 2, 3, or 4) substituents selected from halo.

In one embodiment each L is a divalent, branched or unbranched, saturated or unsaturated, hydrocarbon chain, having from 2 to 10 carbon atoms, wherein one or more of the carbon atoms is replaced by (—O—), and wherein the chain is optionally substituted on carbon with one or more (e.g. 1, 2, 3, or 4) substituents selected from halo.

In one embodiment each L is a divalent, branched or unbranched, saturated or unsaturated, hydrocarbon chain, having from 2 to 5 carbon atoms, wherein one or more of the carbon atoms is replaced by (—O—), and wherein the chain is optionally substituted on carbon with one or more (e.g. 1, 2, 3, or 4) substituents selected from halo.

In one embodiment each L is a divalent, branched or unbranched, saturated or unsaturated, hydrocarbon chain, having from 2 to 5 carbon atoms, wherein one or more of the carbon atoms is optionally replaced by (—O).

In one embodiment each L is —O—$CH_2$—$CH_2$—O—.

The compound of formula III may be polymerized to provide organic-based polymers. Since these polymers are derived from the compound of formula III they are ultimately sourced from renewable resources. The compound of formula III may be polymerized by ring-opening metathesis polymerization (ROMP) with an appropriate catalyst (e.g., a Grubb's catalyst such as a Grubb's III catalyst) to provide a polymer comprising residues of formula 26a:

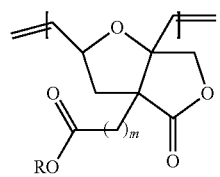

26a wherein: m is 1 or 2; and R is H, ($C_1$-$C_6$)alkyl, or ($C_3$-$C_6$) cycloalkyl; or a salt thereof. In one embodiment the residues of formula 26a are selected from:

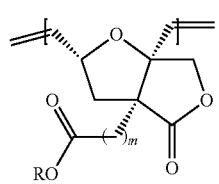 and 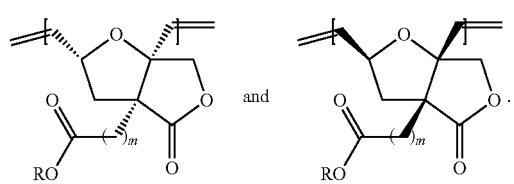

The compound of formula I (e.g., formula Ic1 and the enantiomer thereof) may be polymerized to provide organic-based polymers. Since these polymers are derived from the compound of formula I (e.g., formula Ic1 and the enantiomer thereof) they are ultimately sourced from renewable resources. The compound of formula I (e.g., formula Ic1 and the enantiomer thereof) may be polymerized by ring-opening metathesis polymerization (ROMP) with an appropriate catalyst (e.g., a Grubb's catalyst such as a Grubb's III catalyst) to provide a polymer comprising residues of formula 26:

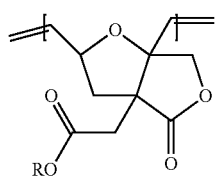

26 wherein R is H, $(C_1-C_6)$alkyl, or $(C_3-C_6)$cycloalkyl; or a salt thereof. In one embodiment the residues of formula 26 are selected from:

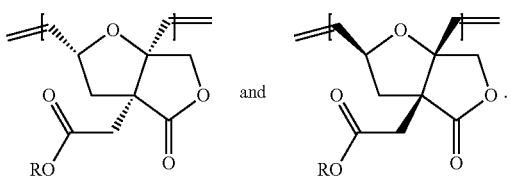

In one embodiment the polymer comprises about 10 or more residues of formula 26 or 26a. In one embodiment the polymer comprises about 50 or more residues of formula 26 or 26a. In one embodiment the polymer comprises about 100 or more residues of formula 26 or 26a. In one embodiment the polymer comprises about 1000 or more residues of formula 26 or 26a. In one embodiment the polymer comprises about 2 or more repeating residues of formula 26 or 26a. In one embodiment the polymer comprises about 5 or more repeating residues of formula 26 or 26a. In one embodiment the polymerization includes an initiator diene (e.g., diethyl diallylmalonate) to promote the polymerization. In one embodiment R is $(C_1-C_6)$alkyl. In one embodiment R is methyl. In one embodiment the residues of formula 26 or 26a form the backbone of the polymer.

In cases where compounds are sufficiently acidic, a salt of a compound of formula I can be useful as an intermediate for isolating or purifying a compound of formula I. Additionally, administration of a compound of formula I as a pharmaceutically acceptable acid or base salt may be appropriate. Examples of pharmaceutically acceptable salts include organic acid addition salts formed with acids that form a physiological acceptable anion, for example, tosylate, methanesulfonate, acetate, citrate, malonate, tartrate, succinate, benzoate, ascorbate, α-ketoglutarate, and α-glycerophosphate. Suitable inorganic acid addition salts may also be formed, that include a physiological acceptable anion, for example, chloride, sulfate, nitrate, bicarbonate, and carbonate salts.

The invention will now be illustrated by the following non-limiting Examples.

EXAMPLES

Example 1

A. General Experimental Protocols $^1$H and $^{13}$C NMR spectra were recorded on a Bruker Avance III or Avance II 500 (500 MHz), a Bruker Avance III 400 (400 MHz), or Varian VXR 300 (300 MHz) spectrometer. $^1$H NMR chemical shifts in $CDCl_3$, $C_6D_6$, or $CD_3OD$ are referenced to TMS (0.00 ppm), $C_6HD_5$ (7.16 ppm), or $CHD_2OD$ (3.31 ppm), respectively. A non-first order multiplet is designated as "nfom". $^{13}$C NMR chemical shifts are referenced to chloroform $CDCl_3$ at 77.16 ppm or benzene $C_6D_6$, at 128.06 ppm. Proton resonances are reported using the following format: chemical shift in ppm (multiplicity, coupling constants (J) in Hz, integral value to the nearest whole proton, and assignment). Coupling constant analysis followed protocols previously reported (Hoye, T. R., et al., J Org. Chem. 1994, 59, 4096-4103; Hoye, T. R., Zhao, H. J. Org. Chem. 2002, 67, 4014-4016).

Infrared (IR) spectra were recorded as solid samples on a Bruker Alpha Platinum spectrometer using attenuated total reflectance (ATR) sampling. The wavenumber of absorption bands are reported in $cm^{-1}$.

Medium pressure liquid chromatography (MPLC, 50-100 psi) was carried out on hand-packed silica gel (25-35 μm, 60 Å pores) columns. A Waters HPLC pump outfitted with a Waters R401 differential refractive index detector and a Gilson UV detector was used. Flash chromatography was performed on silica gel columns (E. Merck, 40-63 μm).

Mass spectrometry data were collected on: i) an Agilent 5973 GC-MS instrument with electron impact ionization (at 70 eV) or ii) a Bruker BioTOF II instrument using electrospray ionization and a PEG internal calibrant for HRMS measurements, or iii) a Bruker Biflex III instrument to carry out the matrix-assisted laser desorption ionization time-of-flight mass spectroscopy (MALDI-ToF-MS), using 2,5-dihydroxybenzoic acid as the matrix.

Size exclusion chromatography (SEC) measurements were performed on an Agilent 1100 series liquid chromatograph equipped with a Varian PLgel 5 mm guard column three Varian Plgel mixed C columns. Analyses were performed at 35° C. with chloroform as the mobile phase. A flow rate of 1 mL·min$^{-1}$ was used and effluent peaks were detected with a differential refractive index detector (HP1047A). Molar masses were determined using a 10-point calibration curve, established using polystyrene standards obtained from Polymer Laboratories.

Differential scanning calorimetry (DSC) was carried out on a Discovery DSC instrument manufactured by TA Instruments. Samples were initially heated to 240° C. and equilibrated at that temperature for 5 min, cooled to −20° C., and ramped back to 240° C. at 10° C. per min. Data were analyzed using Trios Software from TA Instruments.

B. Preparation, Procedures and Characterization Data for Compounds

Preparation of (±)-(1R,2S,4R)-2'H-7-oxaspiro[bicyclo[2.2.1]heptane-2,3'-furan]-5-ene-2',5'(4'H)-dione (4-endo) and (±)-(1R,2R,4R)-2'H-7-oxaspiro[bicyclo[2.2.1]heptane-2,3'-furan]-5-ene-2',5'(4'H)-dione (4-exo)

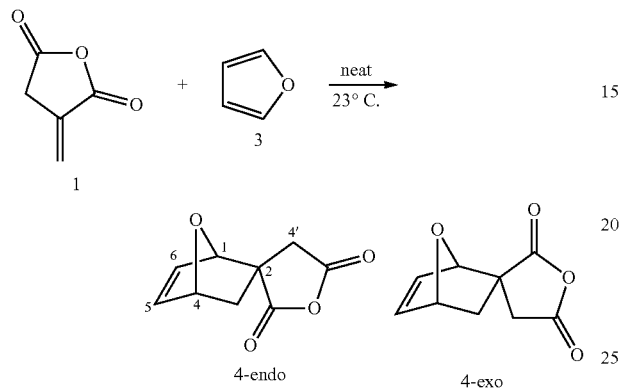

Itaconic anhydride (1, 164 mg, 1.46 mmol) was added to furan (3, 110 µL, 1.47 mmol). The resulting suspension was stirred at ambient temperature for 48 h. The reaction mixture never became homogenous. An aliquot of the mixture was dissolved in $CDCl_3$ and quickly analyzed by $^1H$ NMR spectroscopy, which indicated ca. 60% of each of 1 and 3 along with ca. 40% of a combined mixture of the two isomeric adducts 4-endo and 4-exo. The material was purified by MPLC on silica gel (3:1 hexanes:EtOAc elution) to provide, in order of elution, 4-endo (26.4 mg, 0.147 mmol, 10%) followed by 4-exo (39.6 mg, 0.22 mmol, 15%).

Data for 4-Endo:
$^1H$ NMR ($CDCl_3$, 500 MHz) δ 6.66 (dd, J=5.9, 1.7 Hz, 1H), 6.36 (dd, J=5.9, 1.5 Hz, 1H), 5.20 (nfom, 1H, H4), 4.83 (dd, J=1.8, 1.0 Hz, 1H, H1), 3.20 (d, J=19.1 Hz, 1H, C4'$H_aH_b$), 3.08 (d, J=19.1 Hz, 1H, C4'$H_aH_b$), 2.07 (dd, J=11.6, 3.6 Hz, 1H, C3$H_aH_b$), and 2.05 (ddd, J=11.7, 4.8, 1.2 Hz, 1H, C3$H_aH_b$).

$^1H$ NMR ($C_6D_6$, 500 MHz) δ 5.95 (dd, J=5.8, 1.4 Hz, 1H), 5.80 (dd, J=5.8, 1.0 Hz, 1H), 4.32 (br d, J=4.3 Hz, 1H, H4), 3.68 (br s, 1H, H1), 2.29 (d, J=18.9 Hz, 1H, C4'$H_aH_b$), 1.90 (d, J=18.9 Hz, 1H, C4'$H_aH_b$), 1.24 (d, J=11.6 Hz, 1H, C3$H_aH_b$), and 0.91 (dd, J=11.6, 4.5 Hz, 1H, C3$H_aH_b$).

$^{13}C$ NMR ($C_6D_6$, 125 MHz) δ 173.1, 169.0, 137.9, 132.1, 85.9, 79.5, 49.3, 41.9, and 41.2.

IR (neat): 3014, 2961, 1845, 1767, 1697, 1307, 1238, 987, and 874 $cm^{-1}$.

mp: 102-104° C.

Data for 4-Exo:
$^1H$ NMR ($CDCl_3$, 500 MHz) δ6.71 (dd, J=5.8, 1.7 Hz, 1H), 6.48 (dd, J=5.8, 1.5 Hz, 1H), 5.26 (d, J=4.3 Hz, 1H, H4), 5.11 (s, 1H, H1), 2.77 (d, J=19.3 Hz, 1H, C4'$H_aH_b$), 2.76 (d, J=19.3 Hz, 1H, C4'$H_aH_b$), 2.71 (dd, J=11.5, 4.7 Hz, 1H, C3$H_{exo}H_{endo}$), and 1.53 (d, J=11.5 Hz, 1H, C3$H_{exo}H_{endo}$).

$^1H$ NMR ($C_6D_6$, 500 MHz) δ 5.67 (dd, J=5.8, 1.7 Hz, 1H), 5.38 (dd, J=5.8, 1.6 Hz, 1H), 4.44 (dd, J=4.7, 1.6 Hz, 1H, H4), 4.17 (s, 1H, H1), 2.00 (dd, J=11.5, 4.7 Hz, 1H, C3$H_{exo}H_{endo}$), 1.61 (d, J=18.9 Hz, 1H, C4'$H_aH_b$), 1.52 (d, J=19.0 Hz, 1H, C4'$H_aH_b$), and 0.30 (dd, J=11.5 Hz, 1H, C3$H_{exo}H_{endo}$).

$^{13}C$ NMR ($C_6D_6$, 125 MHz) δ 174.6, 169.0, 139.5, 133.2, 82.5, 79.1, 49.0, 40.8, and 37.7.

IR (neat): 3032, 2947, 1839, 1769, 1229, 1097, 971, 921, 698, 434 $cm^{-1}$.

mp: 159-162° C.

Preparation of (±)-(1R,2S,4S)-2'H-7-oxaspiro[bicyclo[2.2.1]heptane-2,3'-furan]-2',5'(4'H)-dione (4-endo-h2) and (±)-(1R,2R,4S)-2'H-7-oxaspiro[bicyclo[2.2.1]heptane-2,3'-furan]-2',5'(4'H)-dione (4-exo-h2)

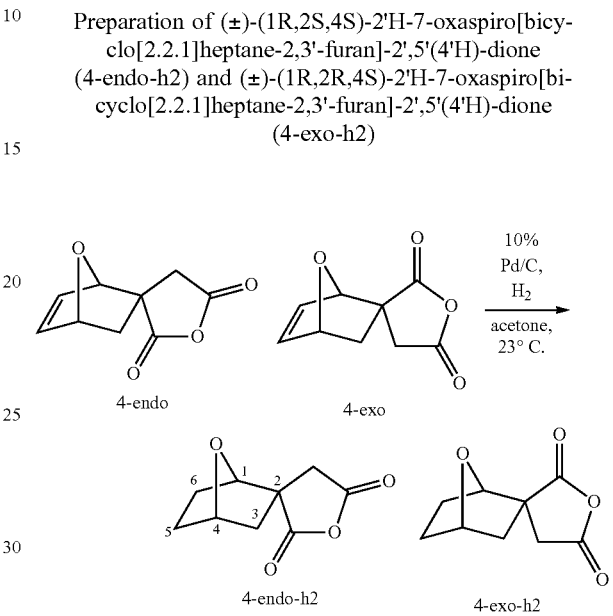

Acetone (100 mL) was placed in a 250 mL, two-neck, round-bottom flask. 10% Pd/C (600 mg) was added. The homogeneous mixture of DA-adducts 4-endo and 4-exo described in the preceding procedure (6.0 g, 33.3 mmol) was added, and the reaction flask headspace was immediately sparged with $H_2$. This suspension was stirred for 3 h and then filtered through a pad of Celite®, that was washed thoroughly with acetone (20 mL). The filtrate was concentrated in vacuo to provide an off-white solid, that was dried overnight under vacuum to give the crude mixture of products 4-endo-h2 and 4-exo-h2 (along with some methylsuccinic anhydride resulting from reduction of the portion of itaconic anhydride in the reactant mixture). A portion of this material (ca. 200 mg) was purified by MPLC on silica gel (5:1 hexanes:EtOAc elution) to provide, in order of elution, 4-endo-h2 (26.4 mg, 0.147 mmol, 10%) followed by 4-exo-h2 (39.6 mg, 0.22 mmol, 15%).

Data for 4-Endo-h2:
$^1H$ NMR ($CDCl_3$, 500 MHz) δ 4.76 (dd, J=5.3, 5.3 Hz, 1H, H4), 4.43 (d, J=5.0 Hz, 1H, H1), 3.22 (d, J=18.9 Hz, 1H, C4'$H_aH_b$), 2.76 (d, J=19.0 Hz, 1H, C4'$H_aH_b$), 2.26 (d, J=12.5 Hz, 1H, C3$H_{endo}H_{exo}$), 2.14 (ddd, J=12.7, 9.0, 4.3 Hz, 1H, H6$_{endo}$), 1.92 (ddd, J=12.4, 5.4, 2.7 Hz, 1H, H3$_{exo}$), 1.86-1.78 (nfom, 1H, H5$_{exo}$), and 1.73-1.65 (m, 2H, H6$_{exo}$ and H5$_{endo}$).

$^1H$ NMR ($C_6D_6$, 500 MHz) δ 4.00 (dd, J=5.3, 5.3 Hz, 1H, H4), 3.31 (d, J=5.2 Hz, 1H, H1), 2.37 (d, J=18.7 Hz, 1H, C4'$H_aH_b$), 1.77 (ddd, J=12.7, 9.0, 4.3 Hz, 1H, H6$_{endo}$), 1.55 (d, J=18.7 Hz, 1H, C4'$H_aH_b$), 1.52 (d, J=12.5 Hz, 1H, C3$H_{endo}H_{exo}$), 1.28 (ddddd, J=12.1, 12.1, 4.7, 4.7, 2.6 Hz, 1H, H5exo), 1.18 (ddd, J=11.7, 9.1, 4.6 Hz, 1H, H5$_{endo}$), 1.07 (dddd, J=12.6, 12.6, 4.9, 4.9 Hz, 1H, H6$_{exo}$), and 0.85 (ddd, J=12.5, 5.4, 2.7 Hz, 1H, H3$_{exo}$).

$^{13}$C NMR (C$_6$D$_6$, 125 MHz) δ 173.7, 168.7, 84.4, 77.8, 54.3, 43.9, 43.9, 29.3, and 24.8.

IR (neat): 1843, 1762, 1237, 1104, 965, 872, and 460 cm$^{-1}$. mp: 149-153° C.

HRMS (ESI-TOF): Calcd for C$_{10}$H$_{14}$NaO$_5$$^+$ [M+MeOH+Na$^+$] requires 237.0733; found 233.0725.

Data for 4-Exo-h2:

$^1$H NMR (500 MHz, CDCl$_3$) δ 4.79 (dd, J=5.1, 5.1 Hz, 1H, H4), 4.73 (d, J=4.6 Hz, 1H, H1), 3.09 (d, J=18.7 Hz, 1H, C4'H$_a$H$_b$), 3.02 (d, J=18.8 Hz, 1H, C4'H$_a$H$_b$), 2.50 (ddd, J=12.3, 5.4, 1.9 Hz, 1H, H3$_{exo}$), 1.93-1.84 (m, 2H), 1.84-1.75 (nfom, 1H, H6$_{endo}$), 1.63 (d, J=12.3 Hz, 1H, H3$_{endo}$), and 1.60-1.52 (nfom, 1H, H5$_{endo}$).

$^1$H NMR (C$_6$D$_6$, 500 MHz) δ 4.12 (dd, J=4.1, 4.1 Hz, 1H, H4), 3.92 (d, J=5.2 Hz, 1H, H1), 1.86 (d, J=18.5 Hz, 1H, C4'H$_a$H$_b$), 1.86 (ddd, J=12.3, 5.4, 2.7 Hz, 1H, H3$_{exo}$), 1.77 (d, J=18.5 Hz, 1H, C4'H$_a$H$_b$), 1.22 (ddddd, J=12.1, 12.1, 5.4, 3.9, 2.8 Hz, 1H, H5$_{exo}$), 1.09 (dddd, J=12.7, 12.7, 4.9, 4.9 Hz, 1H, H6exo), 0.75 (ddd, J=12.8, 9.0, 3.9 Hz, 1H, H6$_{endo}$), 0.62 (ddd, J=11.8, 9.3, 4.9 Hz, 1H, H5$_{endo}$), and 0.47 (d, J=12.3 Hz, 1H, H3$_{endo}$).

$^{13}$C NMR (C$_6$D$_6$, 125 MHz) δ 174.2, 169.0, 80.8, 76.9, 52.3, 43.7, 36.8, 29.0, and 26.3.

IR (neat): 3007, 2975, 2949, 2875, 1843, 1762, 1455, 1307, 1237, 1104, 965, and 873 cm$^{-1}$.

HRMS (ESI-TOF): Calcd for C$_{10}$H$_{14}$NaO$_5$$^+$ [M+MeOH+Na$^+$] requires 237.0733; found 233.0740.

mp: 156-158° C.

Preparation of (±)-(1R,2S,4S)-2-(carboxymethyl)-7-oxabicyclo[2.2.1]heptane-2-carboxylic acid (5)

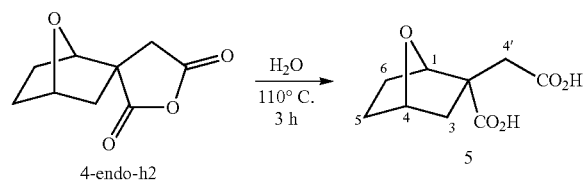

Anhydride 4-endo-h2 (4 mg) was suspended in deionized water (1 mL) in a 10 mL culture tube. The reaction mixture was heated to 110° C. to give a clear solution that was stirred for 3 hours.

The solution was cooled to room temperature and extracted with 4 mL of ethyl acetate. The organic layer was dried over anhydrous MgSO$_4$ and concentrated in vacuo to give the diacid 5 as a white solid (3.5 mg, 81%).

$^1$H NMR (500 MHz, acetone-d$_6$) δ 11.12-10.60 (br s, 2H, CO$_2$H), 4.56 (dd, J=5.2, 5.2 Hz, 1H, H4), 4.25 (d, J=4.7 Hz, 1H, H1), 3.05 (d, J=16.5 Hz, 1H, C4'H$_a$H$_b$), 2.60 (d, J=16.5 Hz, 1H, C4'H$_a$H$_b$), 2.31 (d, J=12.5 Hz, 1H, C3H$_{endo}$H$_{exo}$), 1.72-1.65 (m, 1H), 1.65-1.59 (m, 1H), 1.59-1.54 (m, 2H), and 1.54-1.48 (m, 1H).

$^{13}$C NMR (125 MHz, acetone-d$_6$) δ 174.9, 172.8, 82.8, 79.0, 56.0, 43.7, 41.2, 29.8, and 26.9.

IR (neat): 3300-2500 (br), 2997, 2990, 2974, 1727, 1692, 1411, 1255, 1190, 1145, 1039, 980, 913, 859, and 821 cm$^{-1}$ HRMS (ESI-TOF): Calcd for C$_9$H$_{12}$NaO$_5$$^+$ [M+Na$^+$] requires 233.0577; found 233.0573.

mp: 170-173° C.

Isolation of anhydrides (12-dist) (±)-(1S,2R,4S)-4-(hydroxymethyl)-2'H-7-oxaspiro-[bicyclo[2.2.1]heptane-2,3'-furan]-5-ene-2',5'(4'H)-dione (12-dist-endo) and (±)-(1S,2S,4S)-4-(hydroxymethyl)-2'H-7-oxaspiro[bicyclo[2.2.1]heptane-2,3'-furan]-5-ene-2',5'(4'H)-dione (12-dist-exo)

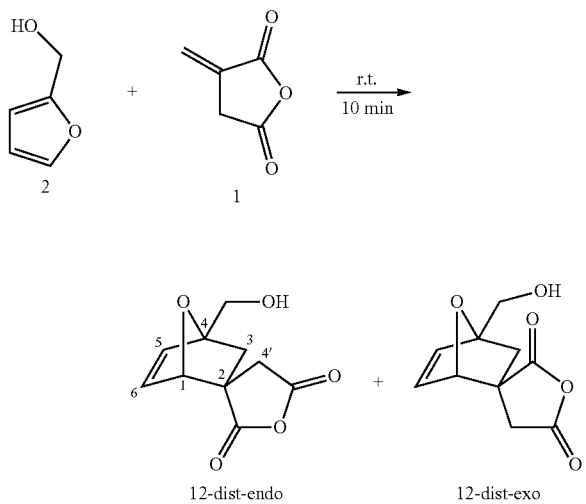

Itaconic anhydride (1, 3.0 g, 26.7 mmol) was suspended in furfuryl alcohol (2, 2.3 mL, 2.6 g, 26.7 mmol) and this slurry was allowed to stir (magnetically) at ambient temperature. After ca. 10 minutes, a portion (200 mg) of the mixture was purified by MPLC (hexanes:EtOAc 3:1) to give the anhydrides 12-dist-endo (1 mg, 0.5%) and 12-dist-exo (1 mg, 0.5%), each as a white solid.

The chromatographic effluent and NMR sample solutions of these compounds were handled and analyzed quickly, because they were susceptible to reversion back to 1 and 2. (also, see following procedure for isolation of 12-prox-endo and 13.)

Data for 12-Dist-Endo:

$^1$H NMR (500 MHz, CDCl$_3$) δ 6.59 (d, J=5.8 Hz, 1H, H5), 6.42 (dd, J=5.8, 1.3 Hz, 1H, H6), 4.84 (d, J=1.5 Hz, 1H, H1), 4.18 (d, J=12.5 Hz, 1H, CH$_a$H$_b$OH), 4.05 (d, J=12.6 Hz, 1H, CH$_a$H$_b$OH), 3.22 (d, J=19.1 Hz, 1H, C4'H$_a$), 3.12 (d, J=19.1 Hz, 1H, C4'H$_b$), 2.08 (d, J=11.5 Hz, 1H, C3H$_a$), 2.02 (d, J=11.5 Hz, 1H, C3H$_b$), and 1.78 (br s, 1H, OH).

Data for 12-Dist-Exo:

$^1$H NMR (500 MHz, CDCl$_3$) δ 6.67 (d, J=5.8 Hz, 1H, H5), 6.54 (dd, J=5.8, 1.4 Hz, 1H, H6), 5.11 (d, J=1.6 Hz, 1H, H1), 4.18 (d, J=12.6 Hz, 1H, CH$_a$H$_b$OH), 4.11 (d, J=12.6 Hz, 1H, CH$_a$H$_b$OH), 2.79 (s, 2H, H4'), 2.62 (d, J=11.5 Hz, 1H, C3H$_a$), 1.95 (br s, 1H, OH), and 1.55 (d, J=11.5 Hz, 1H, C3H$_b$).

Isolation of lactone acid (±)-(4aS,6R,8aR)-3-oxo-3,4,5,6-tetrahydro-1H,4aH-6,8a-epoxyisochromene-4a-carboxylic acid (13)

Preparation of methyl (±)-(4aS,6R,8aR)-3-oxo-3,4,5,6-tetrahydro-1H,4aH-6,8a-epoxyisochromene-4a-carboxylate ($13^{Me}$)

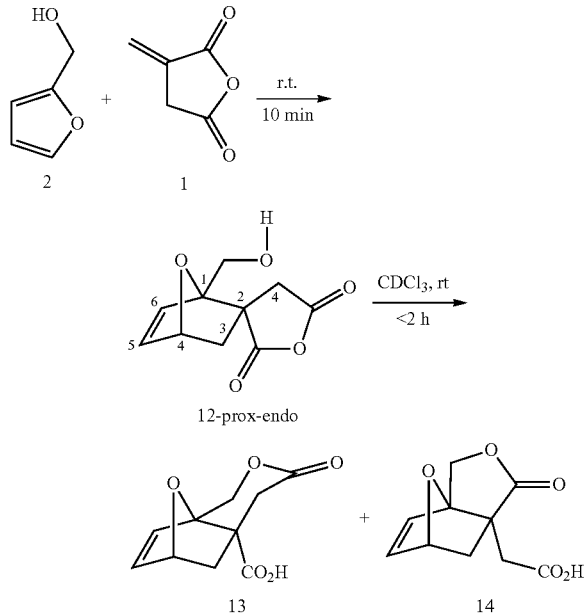

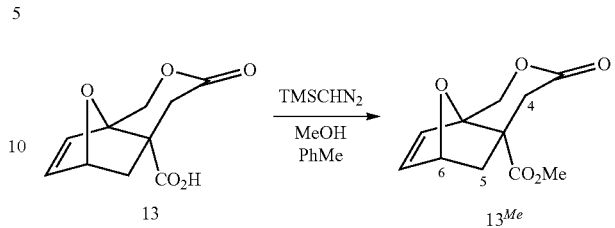

Lactone acid 13 (1 mg) was dissolved in a 1:1 mixture of MeOH and toluene (1 mL) in a 5 mL vial. Excess TMSCHN$_2$ (2 drops) was added to the solution, and the top portion of the solution turned yellow. The vial was capped and gently shaken and allowed to stand for 30 minutes. The reaction mixture was then concentrated in vacuo to give $13^{Me}$ as an off-white solid (1 mg).

$^1$H NMR (400 MHz, CDCl$_3$) δ 6.61 (dd, J=5.7, 1.8 Hz, 1H, H7), 6.06 (d, J=5.7 Hz, 1H, H8), 5.13-5.02 (m, 2H, H6 and C1H$_a$H$_b$), 4.81 (d, J=13.3 Hz, 1H, C1H$_a$H$_b$), 3.71 (s, 3H, CO$_2$CH$_3$), 3.05 (d, J=16.8 Hz, 1H, C4H$_a$H$_b$), 2.74 (d, J=16.8 Hz, 1H, C4H$_a$H$_b$), 2.20 (d, J=12.0 Hz, 1H, H5$_{endo}$), and 1.97 (dd, J=12.0, 4.7 Hz, 1H, H5$_{exo}$).

Preparation of (±)-2-((3aR,6R,7aR)-1-oxo-6,7-dihydro-3H-3a,6-epoxyisobenzofuran-7a(1H)-yl) acetic acid (14)

Itaconic anhydride (1, 3.0 g, 26.7 mmol) was suspended in furfuryl alcohol (2, 2.3 mL, 2.6 g, 26.7 mmol) and this slurry was allowed to stir (magnetically) at ambient temperature. After approximately 10 minutes, a portion (200 mg) of the mixture was purified by MPLC (hexanes:EtOAc 3:1) to give a fraction containing, principally, 12-prox-endo and 13. Upon standing, the 12-prox-endo in a CDCl$_3$ solution of this mixture was observed to fully convert to the 6-membered lactone acid 13 (see copy of $^1$H NMR spectrum for 12-prox-endo), that was then obtained as white solid (1 mg, 0.5%). (also, see previous procedure for isolation of 12-dist-endo and 12-dist-exo.)

Data for 13:

$^1$H NMR (500 MHz, acetone-d$_6$) δ 6.64 (dd, J=5.7, 1.7 Hz, 1H, H7), 6.21 (d, J=5.7 Hz, 1H, H8), 5.12 (d, J=13.2 Hz, 1H, H1a), 5.06 (dd, J=4.8, 1.6 Hz, 1H, H6), 4.69 (d, J=13.2 Hz, 1H, H1b), 3.03 (d, J=16.8 Hz, 1H, C4H$_a$H$_b$), 2.70 (d, J=16.8 Hz, 1H, C4H$_a$H$_b$), 2.15 (d, J=11.8 Hz, 1H, H5endo), and 1.96 (dd, J=11.8, 4.8 Hz, 1H, H5exo). $^{13}$C NMR (125 MHz, CDCl$_3$) δ 176.8, 168.6, 140.3, 132.4, 84.6, 79.2, 68.5, 50.5, 39.9, and 39.5.

IR (neat): 3300-2700 (br s), 3088, 2951, 1715, 1696, 1454, 1423, 1311, 1262, 1184, 1016, 954, and 853 cm$^{-1}$.

HRMS (ESI-TOF): Calcd for C$_{10}$H$_{10}$NaO$_5$$^+$ [M+Na$^+$] requires 233.0420; found 233.0422.

mp: 116-121° C.

Data for 12-Prox-Endo $^1$H NMR (500 MHz, CDCl$_3$) δ 6.66 (br d, J=5.6 Hz, 1H, H5), 6.44 (d, J=5.8 Hz, 1H, H6), 5.13 (dd, J=4.5, 1.7 Hz, 1H, H4), 4.20 (d, J=10.9 Hz, 1H, CH$_a$H$_b$OH), 4.07 (d, J=10.9 Hz, 1H, CH$_a$H$_b$OH), 3.40 (d, J=19.1 Hz, 1H, C4'H$_a$), 2.93 (d, J=19.1 Hz, 1H, C4'H$_b$), 2.22 (d, J=11.6 Hz, 1H, C3H$_{endo}$), and 2.14 (dd, J=11.6, 4.6 Hz, 1H, C3H$_{exo}$).

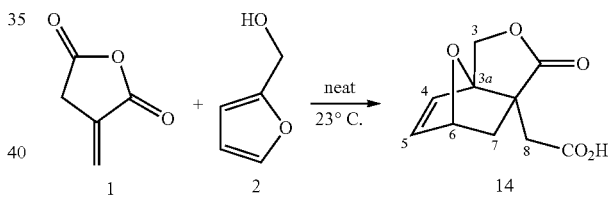

Method A:

Itaconic anhydride (1, 3.0 g, 26.7 mmol) was suspended in furfuryl alcohol (2, 2.3 mL, 2.6 g, 26.7 mmol) and this slurry was allowed to stir (magnetically) at ambient temperature. After approximately five hours, the suspension had thickened to a paste and could no longer be stirred. After approximately 12 hours, this mixture had turned to a solid light brown mass. The lactone 14 could be stored indefinitely as a tan crystalline solid.

Method B:

Itaconic anhydride (1, 1.5 g, 13.3 mmol) was added to furfuryl alcohol (2, 2.3 mL, 2.6 g, 26.7 mmol). This slurry was allowed to stir (magnetically) at ambient temperature and it turned into a clear solution in 30 minutes. After five hours, lactone acid 14 began to precipitate from this solution. After 48 hours the slurry was filtered and the solid was washed with 5 mL of dichloromethane to give 14 as a white solid (1.97 g, 70%).

$^1$H NMR (500 MHz, CDCl$_3$, sparingly soluble) δ 6.59 (dd, J=5.8, 1.7 Hz, 1H, H15), 6.49 (d, J=5.8 Hz, 1H, H4), 5.06 (dd, J=4.7, 1.6 Hz, 1H, H6), 4.83 (d, J=10.8 Hz, 1H, C3H$_a$H$_b$), 4.64 (d, J=10.8 Hz, 1H, C3H$_a$H$_b$), 2.58 (dd, J=12.3, 4.7 Hz, 1H, C7H$_{endo}$H$_{exo}$), 2.54 (d, J=15.1 Hz, 1H, C8H$_a$H$_b$), 2.40 (d, J=15.1 Hz, 1H, C8H$_a$H$_b$), and 1.52 (d, J=12.3 Hz, 1H, C7H$_{endo}$H$_{exo}$).

¹H NMR (500 MHz, acetone-d₆) δ 6.62 (dd, J=5.8, 1.5 Hz, 1H, H5), 6.59 (d, J=5.8 Hz, 1H, H4), 5.03 (dd, J=4.7, 1.3 Hz, 1H, H6), 4.94 (d, J=10.8 Hz, 1H, C3H$_a$H$_b$), 4.51 (d, J=10.8 Hz, 1H, C3H$_a$H$_b$), 2.44 (d, J=15.0 Hz, 1H, C8H$_a$H$_b$), 2.39 (d, J=15.0 Hz, 1H, C8H$_a$H$_b$), 2.35 (dd, J=12.2, 4.8 Hz, 1H, C7H$_{exo}$H$_{endo}$), and 1.58 (d, J=12.2 Hz, 1H, C7H$_{exo}$H$_{endo}$). ¹³C NMR (125 MHz, acetone-d₆) δ 177.8, 171.2, 139.0, 131.5, 95.1, 79.6, 69.1, 52.6, 40.2, and 37.4.

IR (neat): 3300-2500 (br), 2994, 1705, 1397, 1324, 1154, 974, 709, and 646 cm⁻¹.

HRMS (ESI-TOF): Calcd for C₁₀H₉O₅ [M−1⁻] requires 209.0455; found 209.0453.

mp: 137-139° C.

Preparation of (±)-methyl 2-((3aR,6R,7aR)-1-oxo-6, 7-dihydro-3H-3a,6-epoxyisobenzofuran-7a(1H)-yl) acetate (14$^{Me}$)

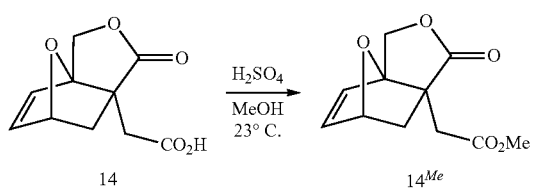

Lactone acid (14, 2.78 g, 13.2 mmol) was dissolved in methanol (10 mL) in a 50 mL two-neck round-bottom flask. Sulfuric acid (0.20 mL, 3.8 mmol) was added. The solution immediately turned deep brown. This solution was stirred overnight at room temperature and the color turned darker. The reaction mixture was concentrated in vacuo and the residue was purified by flash column chromatography on silica gel (CH₂Cl₂ elution) to give lactone ester 14$^{Me}$ (2.30 g, 10.3 mmol, 80%) as a white solid.

¹H NMR (500 MHz, CDCl₃) δ 6.54 (d, J=5.8 Hz, 1H, H5), 6.48 (d, J=5.8 Hz, 1H, H4), 5.03 (d, J=4.7 Hz, 1H, H6), 4.78 (d, J=10.8 Hz, 1H, C3H$_a$H$_b$), 4.59 (d, J=10.8 Hz, 1H, C3H$_a$H$_b$), 3.67 (s, 3H, OCH₃), 2.53 (d, J=11.4 Hz, 1H, C7H$_{endo}$H$_{exo}$), 2.10 (d, J=14.6 Hz, 1H, C8H$_a$H$_b$), 2.31 (d, J=14.6 Hz, 1H, C8H$_a$H$_b$), and 1.48 (d, J=12.2 Hz, 1H, C7H$_{endo}$H$_{exo}$).

¹³C NMR (125 MHz, CDCl₃) δ 177.2, 170.0, 138.2, 130.7, 94.1, 78.8, 68.8, 52.3, 52.1, 39.9, and 36.8.

IR (neat): 1767, 1723, 1437, 1320, 1523, 1178, 1129, 1047, 988, 850, and 707 cm⁻¹.

HRMS (ESI-TOF): Calcd for C₁₁H₁₂NaO₅⁺ [M+Na⁺] requires 247.0577; found 247.0583.

mp: 126-129° C.

Preparation of 1-(furan-2-ylmethyl) 4-methyl 2-methylenesuccinate (15a$^{Me}$)

Method A:

A mixture of (commercial) mono-methyl itaconate 16 (1.0 g, 6.9 mmol), triphenylphosphine (2.6 g, 10.0 mmol), and furfuryl alcohol (0.6 mL, 6.9 mmol) was dissolved in 20 mL of CH₂Cl₂. The solution was gently stirred for 10 min at room temperature. Diethyl azodicarboxylate (DEA, 1.5 mL, 10.2 mmol) was added to the reaction mixture, that was then stirred at room temperature for 17 h. The reaction mass was filtered and the filtrate concentrated. The residue was purified by flash column chromatography on SiO₂ (hexanes/EtOAc, 3:1) to give 15a$^{Me}$ (1.9 g, 85%) as a colorless oil.

Method B:

A neat sample of the lactone methyl ester 14$^{Me}$ (200 mg, 0.89 mmol) was placed in a vial and heated to 140° C. for 20 min. The vial was allowed to cool to room temperature to leave a black oil. This residue was purified by flash column chromatography on SiO₂ (hexanes/EtOAc, 3:1) to give 15a$^{Me}$ as a colorless oil (153 mg, 75%).

¹H NMR (500 MHz, CDCl₃) δ 7.41 (dd, J=1.7, 0.7 Hz, 1H, H5'), 6.42 (d, J=3.2 Hz, 1H, H3'), 6.36-6.35 (m, 2H, H4' and =CH$_Z$H$_E$), 5.72 (br s, 1H, =CH$_Z$H$_E$), 5.15 (s, 2H, furanylCH₂O), 3.66 (s, 3H, CH₃O), and 3.34 (dd, J=1.1, 1.1 Hz, 2H, C3H₂).

¹³C NMR (125 MHz, CDCl₃) δ 171.2, 165.9, 149.4, 143.4, 133.6, 129.3, 110.9, 110.7, 58.8, 52.2, and 37.7.

IR (neat): 2955, 1717, 1637, 1422, 1289, 1152, 1014, 814, and 749 cm⁻¹.

HRMS (ESI-TOF): Calcd for C₁₁H₁₂NaO₅⁺ [M+Na⁺] requires 247.0582; found 247.0575.

TLC: R$_f$ 0.52 (5:1 Hex/EtOAc).

Preparation of 4-(furan-2-ylmethoxy)-2-methylene-4-oxobutanoic acid (15b)

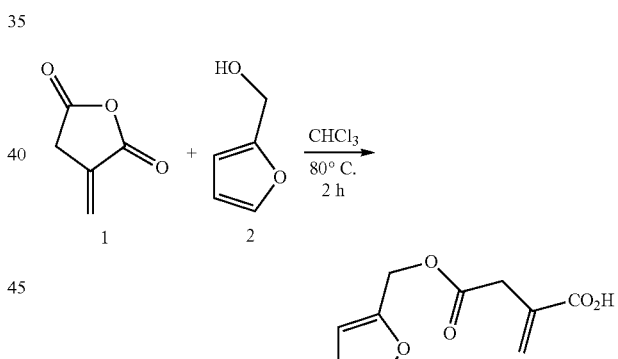

A mixture of itaconic anhydride (1, 200 mg, 1.7 mmol) and furfuryl alcohol (2, 175 mg, 1.7 mmol) was dissolved in 4 mL of CDCl₃ in a round-bottom flask. The solution was

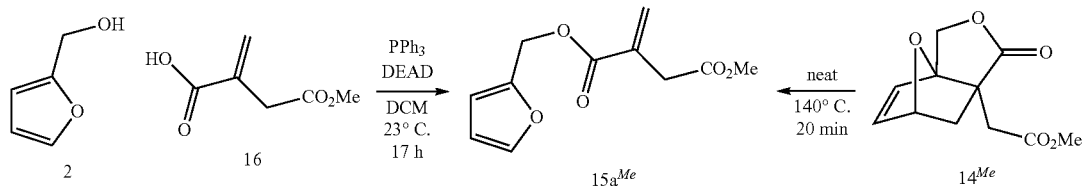

heated to 80° C. and stirred for 2 h. The reaction mass was concentrated and purified by flash column chromatography (SiO$_2$, hexanes/EtOAc, 3:1) to give 15b (0.12 g, 40%) as a white solid.

$^1$H NMR (500 MHz, CDCl$_3$) δ 7.42 (d, J=1.7 Hz, 1H, H5'), 6.47 (s, 1H, =CH$_Z$H$_E$), 6.41 (d, J=3.2 Hz, 1H, H3'), 6.36 (dd, J=3.2, 1.9 Hz, 1H, H4'), 5.83 (s, 1H, =CH$_Z$H$_E$), 5.11 (s, 2H, CH$_2$O), and 3.37 [s, 2H, (HOOC)C(=CH$_2$)CH$_2$].

$^{13}$C NMR (125 MHz, CDCl$_3$) δ 171.0, 170.4, 149.3, 143.5, 133.1, 131.1, 111.0, 110.8, 58.8, and 37.3.

IR (neat): 3300-2500 (br), 3116, 2968, 2903, 2751, 1735, 1695, 1635, 1321, 1168, 1152, 930, 915, and 744 cm$^{-1}$.

HRMS (ESI-TOF): Calcd for C$_{10}$H$_{10}$NaO$_5$$^+$ [M+Na$^+$] requires 233.0420; found 233.0418.

mp: 67-69° C.

Preparation of 4-(furan-2-ylmethyl) 1-methyl 2-methylenesuccinate (15b$^{Me}$)

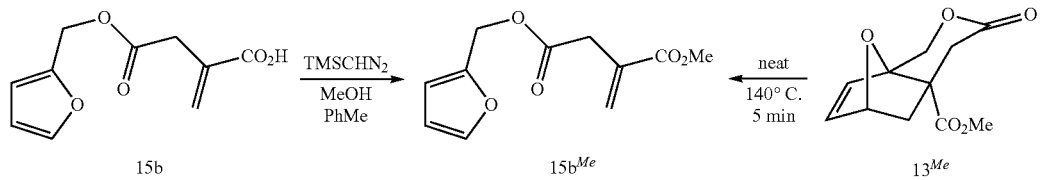 [SMILES: C=C(CC(=O)OCc1ccco1)C(=O)O ; "TMSCHN2" ; C=C(CC(=O)OCc1ccco1)C(=O)OC ; COC(=O)C12CC(=O)OCC13C=CC(C2)O3]

Method A:

Mono-ester acid 15b (1 mg) was dissolved in an equivolume mixture of MeOH and toluene (1 mL) in a 5 mL vial. Excess TMSCHN$_2$ (2 drops) was added to the solution, and the top portion of the solution turned yellow. The vial was capped, gently shaken, and allowed to stand for 30 minutes. The reaction mixture was then concentrated in vacuo to give 15b$^{Me}$ as an off-white solid (1 mg).

Method B:

A neat sample of the lactone methyl ester 13$^{Me}$ (1 mg) was placed in a vial and heated in a 140° C. heating bath for 5 min. The vial was allowed to cool to room temperature to give 15a$^{Me}$ as a brown solid (1 mg).

$^1$H NMR (500 MHz, CDCl$_3$) δ 7.42 (d, J=1.8 Hz, 1H, H5'), 6.41 (d, J=3.2 Hz, 1H, H3'), 6.36 (dd, J=3.1, 1.9 Hz, 1H, H4'), 6.33 (s, 1H, =CH$_Z$H$_E$), 5.71 (s, 1H, =CH$_Z$H$_E$), 5.09 (s, 2H, CH$_2$O), 3.74 (s, 3H, COOMe), and 3.35 (s, 2H, =C(CO$_2$Me)CH$_2$).

Preparation of (±)-3a,7a-(methanoxymethano)benzofuran-2,10(3H)-dione (17)

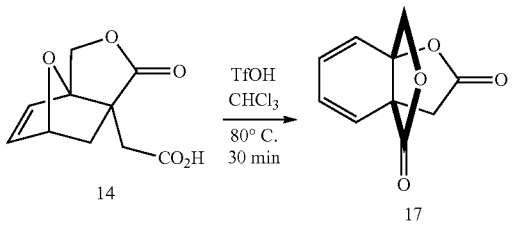

Lactone acid 14 (200 mg, 0.95 mmol) was suspended in chloroform (10 mL) in a 50 mL, two-neck, round-bottom flask. Trifluoromethanesulfonic acid (TfOH, 37 μL, 0.47 mmol) was added to the mixture. A brown-black color was immediately observed. This solution was stirred for 30 min at 80° C. The color of the solution turned dark brown and formation of a black precipitate was observed. The chloroform supernatant was decanted and the black residue was washed with 10 mL of additional chloroform. The combined chloroform layers were concentrated in vacuo and the residue was purified by flash column chromatography on SiO$_2$ (3:1 hexanes:EtOAc elution) to give the rearranged dilactone 17 (73 mg, 0.38 mmol, 40%) as a white crystalline solid.

$^1$H NMR (500 MHz, CDCl$_3$) δ 6.19-6.11 (nfom, 2H), 6.01-5.91 (nfom, 2H), 4.75 (d, J 10.8 Hz, 1H, C8H$_a$H$_b$), 4.25 (d, J=10.8 Hz, 1H, C8H$_a$H$_b$), 3.16 (d, J=18.1 Hz, 1H, C3H$_a$H$_b$), and 2.75 (d, J=18.1 Hz, 1H, C3H$_a$H$_b$).

$^{13}$C NMR (125 MHz, CDCl$_3$) δ 176.6, 171.8, 125.2, 124.0, 123.3, 123.0, 87.5, 76.2, 51.1, and 38.7.

IR (neat): 3150, 3050, 2950, 2900, 1770, 1417, 1361, 1246, 1209, 1186, 1040, 1005, 946, 769, and 715 cm$^{-1}$.

HRMS (ESI-TOF): Calcd for C$_{10}$H$_8$NaO$_4$$^+$ [M+Na$^+$] requires 215.0315; found 215.0325.

TLC: R$_f$ 0.42 (3:1 Hex/EtOAc).

mp: 105-107° C.

Preparation of 3-isochromanone (18)

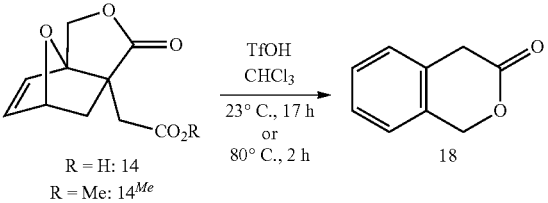

Method A:

Lactone acid 14 (1.0 g, 4.7 mmol) was suspended in chloroform-d (10 mL) in a 50 mL two-neck round-bottom flask. Trifluoromethanesulfonic acid (TfOH, 37 μL, 10 mol %) was added. A brown-black color was immediately observed. This solution was stirred overnight at room temp or heated to 80° C. at which time the color had become somewhat darker and a black solid material had precipitated. The chloroform supernatant was decanted and the black residue was washed with a portion of fresh chloroform. The combined chloroform layers were concentrated in vacuo and the residue was purified by flash column chromatography on SiO$_2$ (hexanes/EtOAc, 3:1) to give 3-isochromanone 18 (0.45 g, 65%) as white crystalline solid.

Method B:

The lactone methyl ester 14$^{Me}$ (0.5 g, 2.2 mmol) was dissolved in chloroform-d (10 mL) in a 50 mL two-neck round-bottom flask. Trifluoromethanesulfonic acid (TfOH, 20 μL, 10 mol %) was added. A brown-black color was immediately observed. This solution was stirred at 80° C. for 2 hours, at which time the color had become somewhat darker. The chloroform was concentrated in vacuo and the residue was purified by flash column chromatography on SiO$_2$ (hexanes/EtOAc, 3:1) to give the 3-isochromanone 18 (0.23 g, 70%) as a white crystalline solid.

$^1$H NMR (500 MHz, CDCl$_3$) δ 7.44-7.21 (m, 4H), 5.40 (s, 2H, CH$_2$O), and 3.79 (s, 2H, CH$_2$CO).

mp: 80-83 (lit. 80-81° C.; Li T., et al., *Helv. Chim. Acta* 2014, 97, 854)

Preparation of (±)-2-((3aR,6S,7aR)-1-Oxotetrahydro-3H-3a,6-epoxyisobenzofuran-7a(1H)-yl)acetic acid (19)

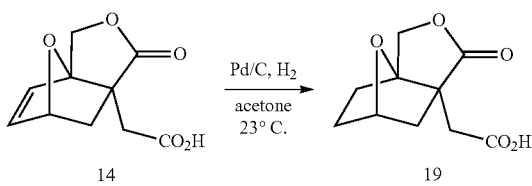 [SMILES: O=C(O)CC12CC3C=CC1(COC2=O)O3 ; O=C(O)CC12CC3CCC1(COC2=O)O3]

Acetone (100 mL) was placed in a 250 mL two-neck round-bottom flask. Lactone acid 14 (1.0 g, 4.7 mmol) was added and stirred for 10 minutes. Pd/C (5%, 50 mg) was added and the reaction flask headspace was immediately sparged with H$_2$. The mixture was stirred for 3 h and then filtered through a pad of Celite®, that was washed thoroughly with acetone (20 mL). The filtrate was concentrated in vacuo to provide an off-white solid, that was dried overnight under vacuum to give the lactone acid 19 (985 mg, 98%) as a white crystalline solid.

$^1$H NMR (500 MHz, CDCl$_3$) δ 4.59 (dd, J=5.3, 5.3 Hz, 1H, H6), 4.57 (d, J=10.5 Hz, 1H, C3H$_a$H$_b$), 4.52 (d, J=10.5 Hz, 1H, C3H$_a$H$_b$), 2.96 (d, J=15.7 Hz, 1H, C8H$_a$H$_b$), 2.54 (d, J=15.7 Hz, 1H, C8H$_a$H$_b$), 2.46 (ddd, J=12.6, 5.0, 2.3 Hz, 1H, C7H$_{endo}$H$_{exo}$), 2.03 (ddddd, J=12.3, 12.3, 5.3, 2.8, 2.8 Hz, 1H, H5exo), 1.93 (ddd, J=12.3, 8.7, 3.1 Hz, 1H, H4endo), 1.78 (ddd, J=12.3, 12.3, 5.6 Hz, 1H, H4exo), 1.75 (d, J=12.5 Hz, 1H, C7H$_{endo}$H$_{exo}$), and 1.63 (ddd, J=12.7, 8.8, 5.6 Hz, 1H, H5endo). $^1$H NMR (500 MHz, acetone-d$_6$) δ 4.58 (d, J=10.4 Hz, 1H, C3H$_a$H$_b$), 4.51 (dd, J=5.3, 5.3 Hz, 1H, H6), 4.42 (d, J=10.4 Hz, 1H, C3H$_a$H$_b$), 2.86 (d, J=15.6 Hz, 1H, C8H$_a$H$_b$), 2.62 (d, J=15.6 Hz, 1H, C8H$_a$H$_b$), 2.22 (ddd, J=12.4, 5.0, 2.3 Hz, 1H, C7H$_{endo}$H$_{exo}$), 2.09-1.99 (m, 1H), 1.94-1.86 (nfom, 1H), 1.84 (d, J=12.4 Hz, 1H, C7H$_{endo}$H$_{exo}$), and 1.78-1.66 (m, 2H).

$^{13}$C NMR (125 MHz, acetone-d$_6$) δ 179.5, 171.7, 92.8, 77.0, 69.6, 53.8, 45.5, 39.4, 29.4, and 25.1.

IR (neat): 3300-2600 (br), 2989, 1706, 1397, 1177, 1459, 1147, 1348, 997, 961, 826, and 604 cm$^{-1}$.

HRMS (ESI-TOF): Calcd for C$_{10}$H$_{12}$NaO$_5$$^+$ [M+Na$^+$] requires 235.0577; found 235.0579.

mp: 173-176° C.

Preparation of (±)-4,7-dihydro-3a,7a-(methanoxymethano)benzofuran-2,10(3H)-dione (20)

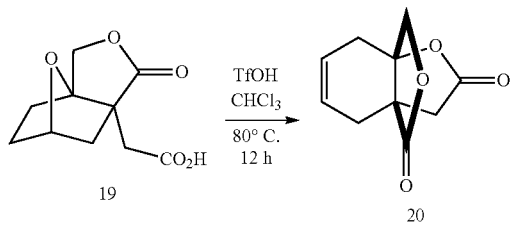

Hydrogenated lactone acid 19 (200 mg, 0.94 mmol) was suspended in chloroform (10 mL) in a 50 mL, two-neck, round-bottom flask. Trifluoromethanesulfonic acid (TfOH, 16 μL, 20 mol %) was added. A brown-black color was immediately observed. This solution was stirred for 12 h at 80° C., at which time the color had become somewhat darker. The chloroform was concentrated in vacuo and the residue was purified by flash column chromatography on SiO$_2$ (hexanes/EtOAc, 3:1) to give the dilactone 20 (56 mg, 30%), that coeluted with a portion of isomer 21, as a colorless oil.

$^1$H NMR (500 MHz, CDCl$_3$) δ 5.96-5.91 (m, 1H, H5 or H6), 5.91-5.86 (m, 1H, H5 or H6), 4.59 (d, J=10.9 Hz, 1H, C8H$_a$H$_b$), 4.20 (d, J=10.9 Hz, 1H, C8H$_a$H$_b$), 3.10 (d, J=18.3 Hz, 1H, C3H$_a$H$_b$), 2.74 (d, J=18.3 Hz, 1H, C3H$_a$H$_b$), 2.68-2.56 (m, 2H), and 2.55-2.45 (m, 2H).

$^{13}$C NMR (125 MHz, CDCl$_3$) δ 178.8, 172.4, 125.6, 124.8, 88.0, 75.0, 48.1, 38.2, 31.0, and 29.9.

IR (neat): 3047, 2963, 2940, 2854, 1768, 1463, 1417, 1308, 1239, 1191, 1018, and 940 cm$^{-1}$.

HRMS (ESI-TOF): Calcd for C$_{10}$H$_{10}$NaO$_4$$^+$ [M+Na$^+$] requires 217.0471; found 217.0481.

TLC: R$_f$0.52 (5:1 Hex/EtOAc).

Preparation of (±)-6,7-dihydro-3a,7a-(methanoxymethano)benzofuran-2,10(3H)-dione (21)

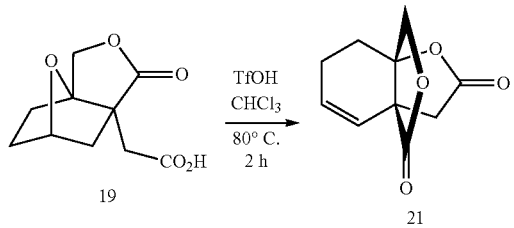

Hydrogenated lactone acid 19 (200 mg, 0.94 mmol) was suspended in chloroform (10 mL) in a 50 mL, two-neck, round-bottom flask. Trifluoromethanesulfonic acid (TfOH, 16 μL, 20 mol %) was added. A brown-black color was immediately observed. This solution was stirred for 2 h at 80° C., at which time the color had darkened. The chloroform was concentrated in vacuo and the residue was purified by flash column chromatography on SiO$_2$ (3:1 hexanes: EtOAc elution) to give the dilactone 21 (54 mg, 30%), that coeluted with a portion of isomer 20, as a colorless oil.

$^1$H NMR (500 MHz, CDCl$_3$) δ 6.06 (ddd, J=9.6, 5.6, 2.1 Hz, 1H, H5), 5.80 (ddd, J=9.8, 2.5, 1.1 Hz, 1H, H4), 4.52 (d, J=11.1 Hz, 1H, C8H$_a$H$_b$), 4.31 (d, J=11.1 Hz, 1H, C8H$_a$H$_b$), 3.20 (d, J=18.2 Hz, 1H, C3H$_a$H$_b$), 2.68 (d, J=18.2 Hz, 1H, C3H$_a$H$_b$), 2.40 (ddddd, J=18.7, 5.9, 5.9, 1.9, 1.9 Hz, 1H, C6H$_a$H$_b$), 2.27 (ddd, J=13.8, 5.8, 2.2 Hz, 1H, C7H$_a$H$_b$), 2.19-2.09 (m, 1H, C6H$_a$H$_b$), and 1.78 (ddd, J=13.6, 12.0, 6.2 Hz, 1H, C7H$_a$H$_b$).

$^{13}$C NMR (125 MHz, CDCl$_3$) δ 176.0, 172.3, 130.3 (C5), 122.5 (C4), 87.6 (C7a), 71.5 (C8), 50.0 (C3a), 38.4 (C3), 26.3 (C7), and 22.8 (C6) (assignments supported by analysis of the HMQC and HMBC spectra).

IR (neat): 3075, 3100, 2925, 2875, 1763, 1469, 1421, 1288, 1230, 1188, 1154, 1015, 936, 709, and 617 cm$^{-1}$.

HRMS (ESI-TOF): Calcd for C$_{10}$H$_{10}$NaO$_4^+$ [M+Na$^+$] requires 217.0471; found 217.0479.

TLC: R$_f$0.52 (5:1 Hex/EtOAc).

Preparation of (±)-tetrahydro-3a,7a-(methanoxymethano)benzofuran-2,10(3H)-dione (22)

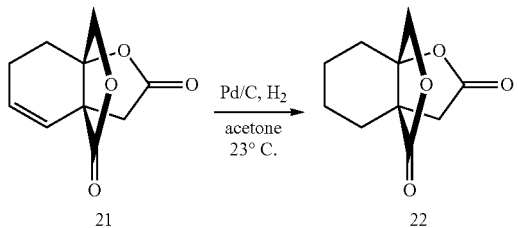

Alkene 21 (800 mg, 4.1 mmol) was dissolved in acetone (40 mL) in a 100 mL, two-neck, round-bottom flask. To this mixture was added palladium on activated carbon (10% Pd/C, 80 mg). The vessel was closed with a rubber septum and H$_2$ gas was introduced via a balloon. The mixture was stirred at room temperature for 4 h. The resulting suspension was filtered through a plug of Celite®. The filtrate was concentrated under reduced pressure and the crude material was purified by flash column chromatography (EtOAc/MeOH, 2:1) to give 22 (767 mg, 95%) as a white solid.

$^1$H NMR (500 MHz, CDCl$_3$) 4.49 (d, J=11.2 Hz, 1H, C8H$_a$H$_b$), 4.33 (d, J=11.2 Hz, 1H, C8H$_a$H$_b$), 2.96 (d, J=18.0 Hz, 1H, C3H$_a$H$_b$), 2.74 (d, J=18.0 Hz, 1H, C3H$_a$H$_b$), 2.22 (dddd, J=14.6, 3.6, 3.6, 1.5 Hz, 1H), 2.13 (dddd, J=14.6, 3.4, 3.4, 2.0 Hz, 1H), 1.94-1.88 (m, 1H), 1.82-1.76 (m, 1H), 1.59 (ddd, J=14.5, 13.1, 4.6 Hz, 1H), 1.54 (ddd, J=14.6, 12.9, 4.2 Hz, 1H), 1.36 (ddddd, J=12.6, 12.6, 12.6, 3.2, 3.2 Hz, 1H), and 1.28 (ddddd, J=14.6, 12.8, 12.8, 3.4, 3.4 Hz, 1H).

$^1$H NMR (500 MHz, C$_6$D$_6$) δ 3.75 (d, J=11.1 Hz, 1H, C8H$_a$H$_b$), 3.35 (d, J=11.1 Hz, 1H, C8H$_a$H$_b$), 2.65 (d, J=17.9 Hz, 1H, C3H$_a$H$_b$), 2.01 (d, J=17.9 Hz, 1H, C3H$_a$H$_b$), 1.34 (dddd, J=14.4, 3.4, 3.4, 2.0 Hz, 1H), 1.24 (dddd, J=14.4, 2.1, 2.1, 1.2 Hz, 1H), 0.96-0.89 (m, 1H), 0.82 (dddddd, J=13.6, 3.1, 3.1, 3.1, 3.1, 1.2 Hz, 1H), 0.75 (ddd, J=14.6, 13.3, 4.7 Hz, 1H), 0.73 (ddd, J=14.9, 12.8, 4.2 Hz, 1H), 0.40 (ddddd, J=12.6, 12.6, 12.6, 3.4, 3.4 Hz, 1H), and 0.26 (ddddd, J=13.3, 13.3, 13.3, 3.3, 3.3 Hz, 1H).

$^{13}$C NMR (125 MHz, CDCl$_3$) δ 178.4, 172.4, 87.6, 71.0, 48.1, 34.6, 30.2, 28.0, 22.0, and 19.7.

IR (neat): 2941, 2867, 1776, 1461, 1379, 1237, 1189, 1042, 1003, and 921 cm$^{-1}$.

HRMS (ESI-TOF): Calcd for C$_{10}$H$_{12}$NaO$_4^+$ [M+Na+] requires 219.0628; found 219.0626.

mp: 95-99° C.

Preparation of o-tolylacetic acid (23)

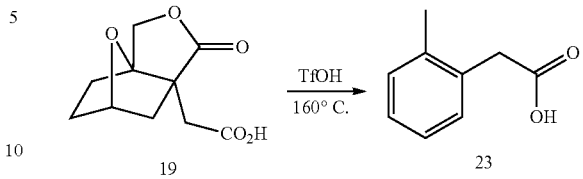

Hydrogenated lactone acid (19, 2.0 g, 9.4 mmol) was placed in a 50 mL, two-neck, round-bottom flask. Trifluoromethanesulfonic acid (TfOH, 80 μL, 1.0 mmol) was added; and the mixture was purged with N$_2$, tightly capped, and heated to 160° C. for 7 h. The reaction time depended on scale for this heterogeneous process. Reaction progress could be monitored by $^1$H NMR analysis of an aliquot. The reaction mixture turned deep brown. The reaction mixture was dissolved in EtOAc (ca. 10 mL) and that solution was washed with water (ca. 10 mL). The organic layer was washed with brine, dried with MgSO$_4$, filtered, and concentrated in vacuo to give crude o-tolylacetic acid 23 (1.3 g, 7.7 mmol, 81%) as a dark brown solid. A portion (350 mg) was purified by MPLC (3:1 hexanes:EtOAc elution) to give a pale yellow solid (332 mg; 77% yield).

$^1$H NMR (400 MHz, CDCl$_3$) δ 7.22-7.16 (m, 4H), 3.67 (s, 2H, CH$_2$CO$_2$H), and 2.33 (s, 3H, CH$_3$).

mp: 84-86° C. (lit. 88-89° C.; Chauffe, L., et al., J. Org. Chem. 1966, 31, 3758-3764).

Preparation of 2-(o-tolyl)ethanol (S1)

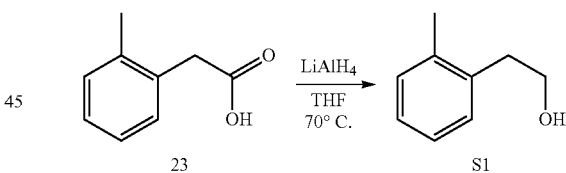

A solution of o-tolylacetic acid 23 (330 mg, 2.20 mmol) in dry ether (5 mL) was slowly added to a stirred mixture of LiAlH$_4$ (180 mg, 4.7 mmol) in dry ether (5 mL) in a 100 mL round-bottom flask. Once gas evolution had subsided, the mixture was refluxed for 3 h. The mixture was quenched by careful addition of 0.2 mL of water, 0.2 mL of 15% NaOH aqueous solution, and 1.2 mL of water. The insoluble salts were removed by filtration, and the organic layer was washed with brine and dried over anhydrous MgSO$_4$. The ether was removed on a rotary evaporator with an ambient temperature bath to leave 2-(o-tolyl) ethanol (S1) (Sakai, N., et al., Eur. J. Org. Chem. 2011, 3178-3183) as a light yellow liquid (219 mg, 1.61 mmol, 75%).

$^1$H NMR (500 MHz, CDCl$_3$) δ 7.22-7.10 (m, 4H), 3.85 (t, J=6.9 Hz, 2H, CH$_2$OH), 2.90 (t, J=6.8 Hz, 2H, CH$_2$Ar), 2.34 (s, 3H, CH$_3$), and 1.42 (br s, 1H, OH).

Preparation of 2-methylstyrene (24) and o-xylene (25)

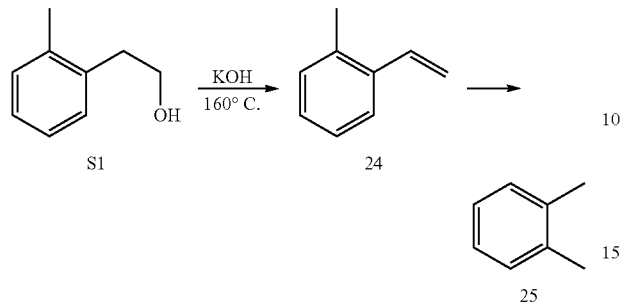

2-(o-Tolyl) ethanol (S1, 34 mg, 0.25 mmol) and KOH pellets (85 mg, 1.5 mmol) were added to a culture tube. The reaction mixture was heated in a 160° C. oil bath for 1 h. The residue from the cooled mixture was purified using MPLC (19:1, Hexanes:EtOAc elution) to give a mixture of 2-methylstyrene (24) and o-xylene (25) as a coeluting, colorless liquid (17 mg, 0.15 mmol, 58%). The ratio, judged from analysis of the $^1$H NMR spectrum, was 3.3:1 of 24:25.

$^1$H NMR (of the mixture of hydrocarbons, 500 MHz, CDCl$_3$) δ 7.49-7.46 (nfom, 1H), 7.19-7.08 (m, 5H), 6.95 (dd, J=17.4, 11.0 Hz, 1H), 5.63 (dd, J=17.4, 1.3 Hz, 1H), 5.29 (dd, J=11.0, 1.3 Hz, 1H), 2.35 (s, 3H, styrenylCH$_3$), and 2.26 (s, 1.8H, xylenylCH$_3$s). (literature spectral data: E. Alacid, C. Najera, *J. Org. Chem.* 2009, 74, 8191-8195).

C. Ring-Opening Metathesis Polymerization (ROMP) of Lactone Methyl Ester 14$^{Me}$ to Give 26

The lactone methyl ester 14$^{Me}$ (100 mg, 0.45 mmol) was added to a 10 mL culture tube and dissolved in CH$_2$Cl$_2$ (1 mL). Diethyl diallylmalonate (2-10 μL, 2-10 mg, 9-42 mmol, see Table 1) was added. The vial was sealed with a rubber septum and the solution and headspace were sparged with argon gas. In a separate scintillation vial, a solution of Grubbs III pre-catalyst [(SIMes)Ru(Cl$_2$)(3-Br-py)$_2$=CHPh or dichloro[1,3-bis(2,4,6-trimethylphenyl)-2-imidazolidinylidene]-(benzylidene)bis(3-bromopyridine)ruthenium(II)] in CH$_2$Cl$_2$ was prepared and then added to the lactone methyl ester solution within 2 minutes of its preparation. This solution was allowed to stir at ambient temperature for 24 hours. Excess ethyl vinyl ether (0.5 mL) was added to arrest further metathesis events. The product was purified by precipitation: the CH$_2$Cl$_2$ solution was added into methanol (200 mL) and stirred for ca. 30 min. The slurry was filtered and the off-white solid was dried under vacuum overnight to provide 50-60 mg of material. All manipulations were carried out at ambient temperature.

26 (Sample from Entry 1)

$^1$H NMR (500 MHz, DMSO-d$_6$) δ 5.76 (br d, J=10.9 Hz, 2H), 5.6-5.3 (m, =CH$_2$ from terminating methylenes), 4.48 (br s, 1H), 4.29 (m, 2H), 3.60 (br s, 3H), 2.96 (br d, J=17.4 Hz, 1H), 2.63 (br d, J=17.3 Hz, 1H), 2.32 (br s, 1H), and 1.76 (br s, 1H).

TABLE 1

[a]Characterization data for two samples of ROMP polymer 26.

| Entry | Initiator (mol %) | $M_n$ (theo) | $M_n$ (NMR)[b] | $M_n$ (SEC)[c] | $M_w$ (SEC)[c] | Đ | $T_g$ (° C.) |
|---|---|---|---|---|---|---|---|
| 1 | 9.3 | 2.4 | 1.6 | 2.6 | 3.2 | 1.22 | 123 |
| 2 | 5.3 | 4.2 | 2.7 | 3.0 | 3.7 | 1.26 | 131 |

[a]$M_n$ and $M_w$ values in kg · mol$^{-1}$.
[b]$M_n$ from $^1$H NMR analysis, assuming every polymer has a vinyl group (i.e., RCH=CH$_2$) on each of its termini - a reasonable assumption since even if a malonate unit is present (see MALDI below), that group should still be terminated by a vinyl group.
[c]vs. polystyrene standard (in CHCl$_3$).

D. General Procedure for the DA Reaction Between Furan 3, 5, 7, or 9 and IA (1)

An excess amount of the furan (ca. 20 equiv) was added to a capped flask containing 1 (1 equiv) to form a slurry. The mixture was allowed to stir at room temperature. Aliquots of the mixture were periodically removed in order to monitor the progress of the DA reaction by $^1$H NMR analysis, that was carried out immediately after each NMR sample was prepared. To obtain useful signal to noise levels of the $^1$H NMR resonances for the minor amounts of product often being observed, relatively concentrated solutions of CDCl$_3$ NMR samples were used. The percent conversion to DA adducts was recorded as the equilibrium conversion in Table 10. When the relative amounts of observed species remained constant in two consecutive aliquots, it was deemed that equilibrium had been reached. The reaction time required to reach half of the equilibrium conversion is provided as $t_{1/2}$ in Table 10. FIGS. 4-7 display the final equilibrium $^1$H NMR spectrum for each of the reactions shown in entries 1-4 of Table 10.

E. Computational (DFT) Methodology Used and Free Energies and Geometries for 13'/13, 14'/14, 13'$^{Me}$/13$^{Me}$, and 14'$^{Me}$/14$^{Me}$ Each of structures in Scheme 2B was subjected to a molecular mechanics multiconformational search in Macromodel (version 10.7). The resulting minima were each subjected to an M06-2X/6-31+G(d,p) optimization calculation with a "tight" cutoff and an "ultrafine" integration grid in Gaussian 09 (Y. Zhao, D. G. Truhlar, *Theor. Chem. Acc.* 2008, 120, 215-241; M. J. Frisch, et al., Gaussian 09, Revision A.02, Gaussian, Inc., Wallingford Conn., 2009). This was followed by a frequency calculation (at 298 K) to obtain the Gibbs energy for each conformer. Solvation in chloroform was accounted for by using the SMD solvation model. (V. Marenich, C. J. Cramer, D. G. Truhlar, *J. Phys. Chem. B* 2009, 113, 6378-6396). Each conformer was Boltzmann-weighted based on its Gibbs energy to obtain its mole fraction. The mole fractions of all conformers for each isomer were used to determine the overall (Boltzmann-averaged) Gibbs energy of that isomer.

F. NMR-Based Assignment of Relative Configuration to 4-Exo Vs. 4-Endo, Including Comparisons Between Computed and Experimental Chemical Shifts To assign the structure of the endo vs. exo stereoisomers in these series of compounds, the following sequence of experiments were carried out. First, the equilibrium mixture of products 4 was dissolved in acetone and quickly exposed to 10% Pd/C and hydrogen gas (1 atm) in order to saturate the alkene, thereby arresting further cycloreversion to itaconic anhydride (1) and furan (3), a process that is promoted by the simple act of dilution. The diastereomeric saturated analogs 4-h2 were chromatographically separated and individually characterized.

Second, in order to correlate that isomer of 4-h2 came from that isomer of the alkene adducts 4 it was necessary to separate the latter pair. A mixture of the exo- and endo-isomers of 4 was quickly chromatographed on $SiO_2$ (MPLC), and $^1H$ NMR data were collected for each (in both $CDCl_3$ and $C_6D_6$). A sample of the slower eluting isomer of 4, immediately following chromatographic separation, was then quickly reduced by $H_2$ to give the same isomer of 4-h2, that eluted more slowly, thereby allowing the correlation of the two slower eluting isomers of each pair.

Figure 10A:
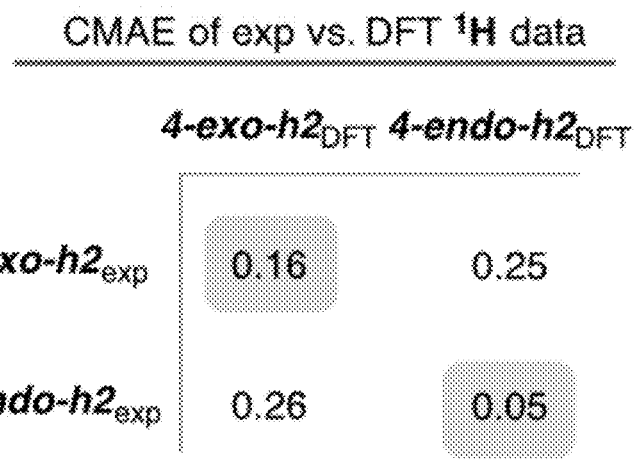
FIGS. 10A and 10B show the CMAEs for $^1$H (10A) and $^{13}$C (10B) computed chemical shifts between matched and unmatched 4-exo-h2 and 4-endo-h2.
Figure 10B:
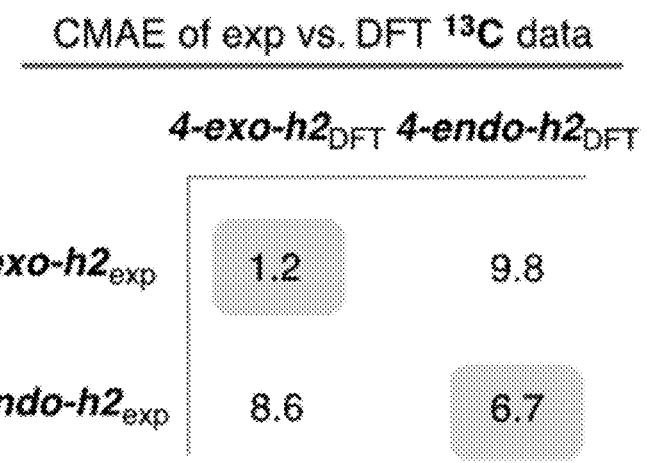

To aid in the assignment of relative configuration of each of the diastereomeric pairs, the NMR chemical shifts of each of the four structures of 4 and 4-h2 were computed in Gaussian 09 using DFT [B3LYP/6-311+G(2d,p)//M06-2X/6-31+G(d,p), both using SMD:$CHCl_3$]. Optimizations were run using an "ultrafine" integration grid and were subjected to a "tight" cutoff. A multiconformational search (carried out in Macromodel, version 10.7) resulted in only a single minimum energy conformation for each of these rigid anhydrides, making Boltzmann averaging unnecessary. Experimental and computed values were then compared (Tables 2-9). In order to reduce error, least-squares linear regression analysis of the experimental vs. the computed chemical shifts ($\delta_{exp}$ and $\delta_{comp}$, respectively) was carried out for each isomer. The corrected chemical shift values ($\delta_{corr}$) were extracted from the resulting linear equation ($\delta_{corr}$=slope×$\delta_{comp}$+intercept). The corresponding corrected mean absolute error (CMAE) for the sets of both the carbon and, especially, the proton chemical shifts (FIGS. 10 and 11) suggested that the structure of the faster eluting isomer in each pair was 4-endo-h2 and 4-endo, while that of the less chromatographically mobile isomer was 4-exo-h2 and 4-exo.

Figure 12A:
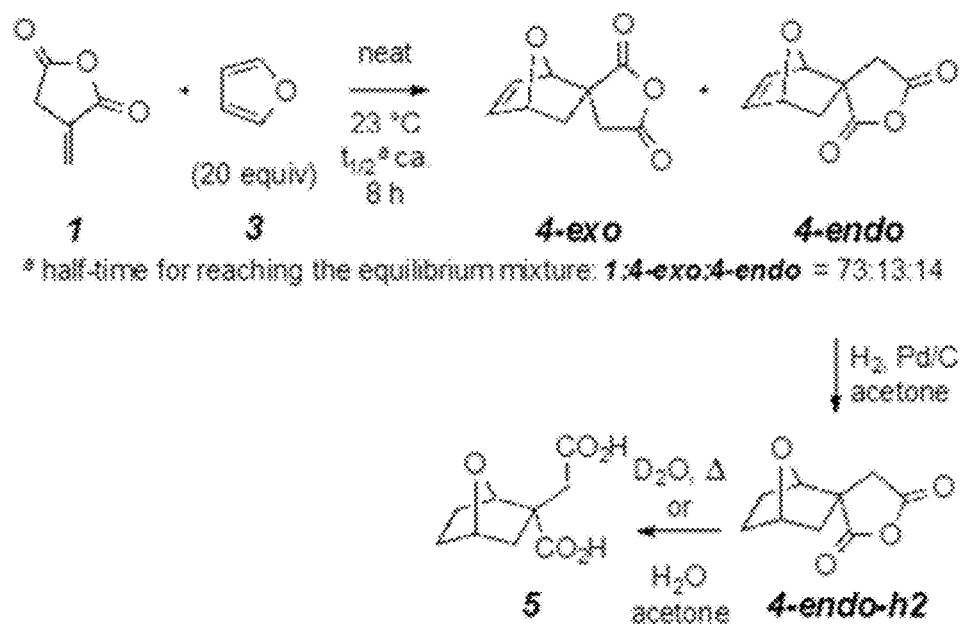
FIG. 12A shows the rate and final equilibrium resting state for the DA reaction between IA (1) and furan (3) and the conversion of 4-endo to 5 via 4-endo-h2.
Figure 12B:
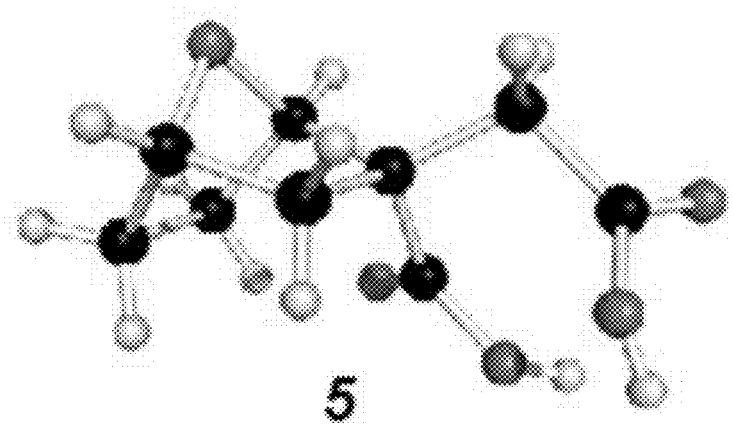
FIG. 12B shows the 3D structure of 5 from a single crystal X-ray analysis.
Figure 14:
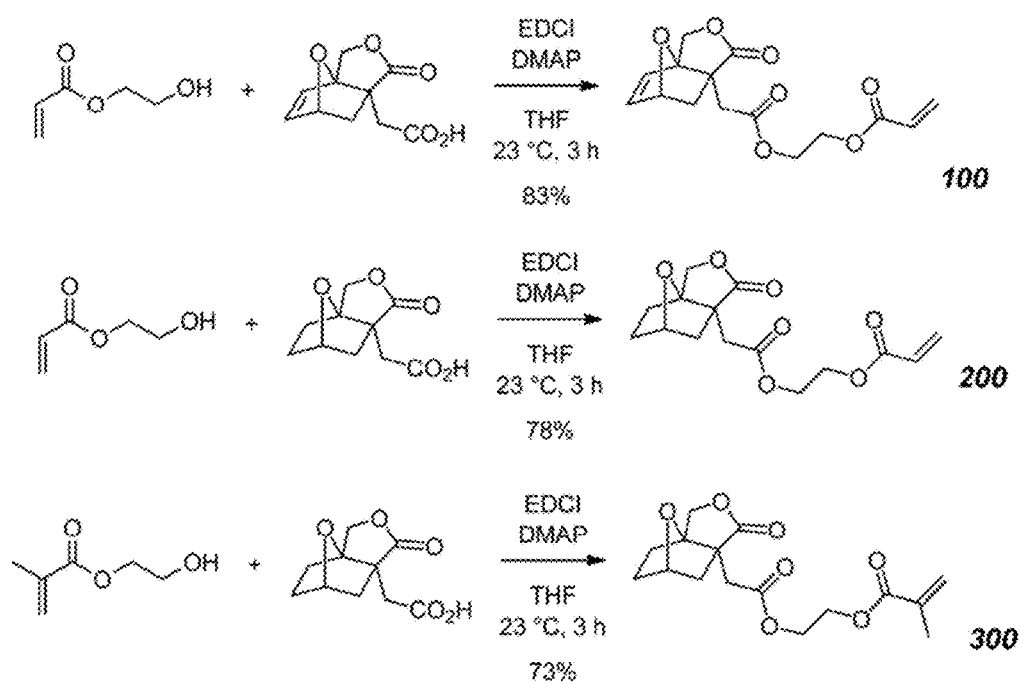
FIG. 14 shows the preparation of compounds 100, 200, and 300, as further described in Examples 2, 3, and 4.
Figure 15:
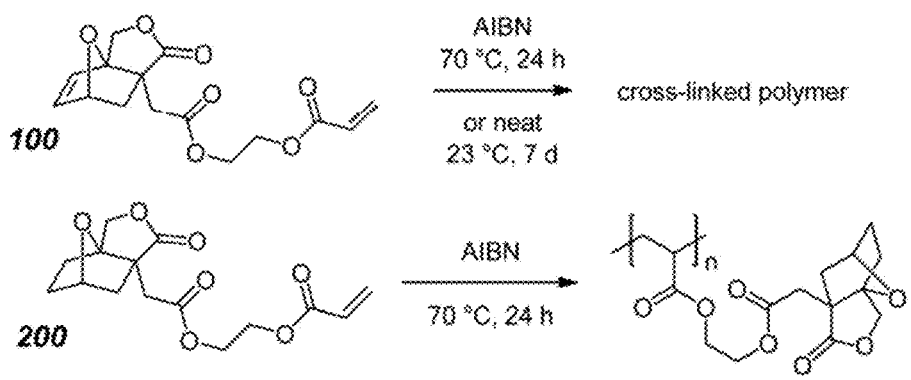
FIG. 15 shows the polymerization of compounds 100 and 200, as further described in Examples 5 and 6.
Figure 16:
FIG. 16 shows the polymerization of compound 200 under RAFT conditions, as further described in Example 7, and 300.
Figure 17:
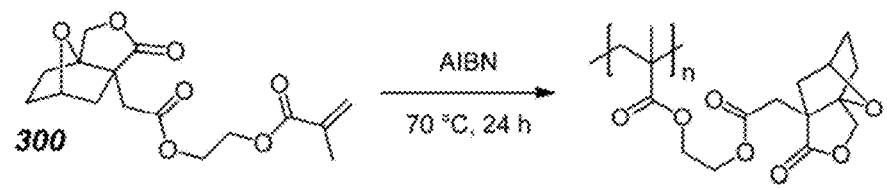
FIG. 17 shows the polymerization of compound 300, as further described in Example 8.
Figure 18:
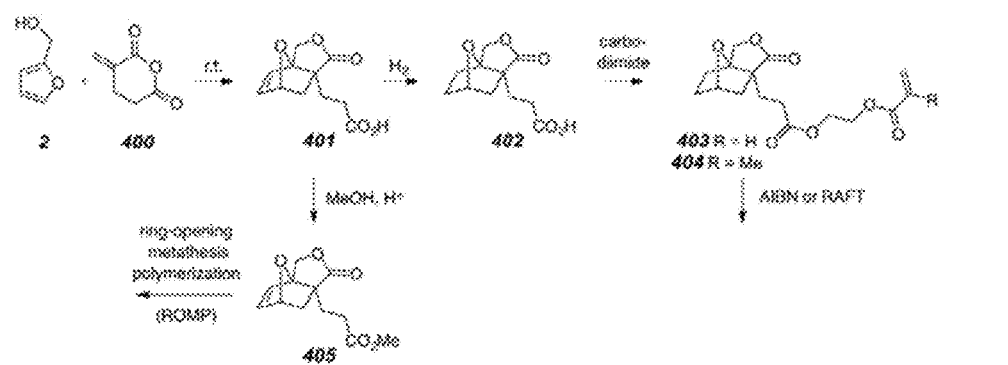
FIG. 18 illustrates compounds and synthetic processes of the invention.

It is worth noting that NOE experiments did not provide a definitive basis for confidently assigning either of these pairs of exo- and endo-diastereomers. Finally, these structural assignments were confirmed by the X-ray diffraction analysis of the diacid 5 derived from the faster eluting, hydrogenated compound—4-endo-h2 (FIG. 12B). When this anhydride was added to hot $D_2O$ (or incubated in a homogenous solution of aqueous acetone), it smoothly opened to the diacid 5.

Figure 9:
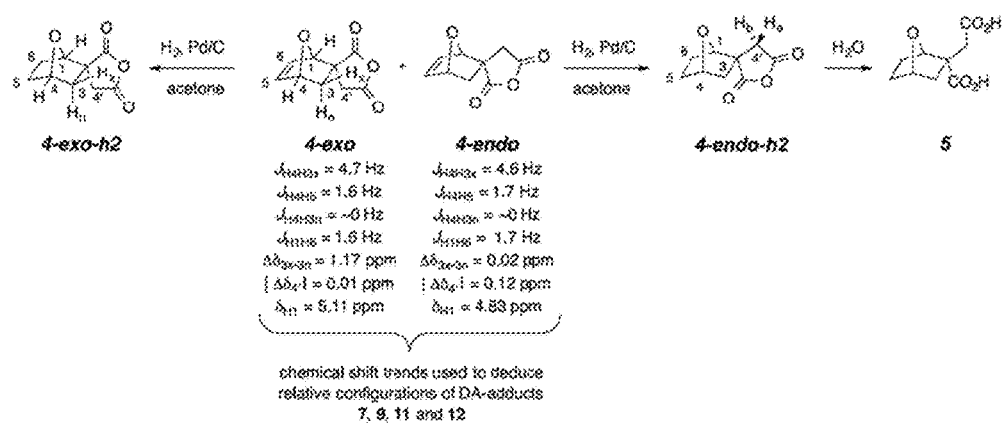
FIG. 9 shows the diagnostic trends in NMR data that for 4-exo vs. 4-endo that were used to deduce and assign the relative configuration within DA adducts 7, 9, and 11.

Diagnostic features in the $^1H$ NMR spectral data of each diastereomer of 4 were then useful to assess and deduce the relative configuration of the DA adducts prepared from additional furan derivatives (7, 9, and 11 in Table 10). As shown in FIG. 9, these include (i) the multiplicity of the bridgehead proton adjacent to vs. remote from the spirocyclic quaternary carbon [H1 in, e.g., 4-exo was a simple doublet (J=ca. 2 Hz) whereas H4 was a dd (J=ca. 5 and 2 Hz) showing coupling to $H3_x$ but not $H3_n$, because the H4/$H3_n$ dihedral angle is near 90°] and (ii) the differences in chemical shifts of the diastereotopic methylene protons at C3 and C4' as well as the $\delta_{rel}$ values for the bridgehead protons, when present. Because the equilibrium concentration for all of these adducts was typically low (5-20%, Table 10), their spectral data were recorded and analyzed from a mixture of the endo and exo adducts along with the excess diene (i.e., furan derivative) and remaining IA (1) (FIG. 12 and FIGS. 4-7).

TABLE 2

Error correction for computed 4-endo-h2 $^1H$ chemical shifts.

| Atom | Computed Shift | Experimental Shift | Error | Scaled (Linearly Corrected) Shift | Scaled Error |
|---|---|---|---|---|---|
| 2 | 4.35 | 4.43 | 0.08 | 4.41 | 0.02 |
| 3-Endo | 1.99 | 2.14 | 0.15 | 2.04 | 0.10 |
| 3-Exo | 1.58 | 1.65 | 0.07 | 1.63 | 0.02 |
| 4-Endo | 1.66 | 1.73 | 0.07 | 1.71 | 0.02 |
| 4-Exo | 1.76 | 1.82 | 0.06 | 1.81 | 0.01 |
| 5 | 4.64 | 4.76 | 0.12 | 4.70 | 0.06 |
| 6-Endo | 2.30 | 2.26 | −0.04 | 2.35 | −0.09 |
| 6-Exo | 1.83 | 1.92 | 0.09 | 1.88 | 0.04 |
| 9 (pro-R) | 3.21 | 3.22 | 0.01 | 3.27 | −0.05 |
| 9 (pro-S) | 2.81 | 2.76 | −0.05 | 2.87 | −0.11 |

TABLE 3

Error correction for computed 4-endo-h2 $^{13}C$ chemical shifts.

| Atom | Computed Shift | Experimental Shift | Error | Scaled (Linearly Corrected) Shift | Scaled Error |
|---|---|---|---|---|---|
| 1 | 62.5 | 54.6 | −7.9 | 61.3 | −6.7 |
| 2 | 91.8 | 84.9 | −6.9 | 89.4 | −4.5 |
| 3 | 29.0 | 24.6 | −4.4 | 30.2 | −5.6 |
| 4 | 32.9 | 29.2 | −3.7 | 34.1 | −4.9 |
| 5 | 84.7 | 78.2 | −6.5 | 84.2 | −6.0 |
| 6 | 48.5 | 44.5 | −4.0 | 45.3 | −0.8 |
| 7 | 187.0 | 173.6 | −13.4 | 188.1 | −14.5 |
| 8 | 182.5 | 168.7 | −13.8 | 183.4 | −14.7 |
| 9 | 49.2 | 44.2 | −5.0 | 41.4 | 2.8 |

TABLE 4

Error correction for computed 4-exo-h2 $^1H$ chemical shifts.

| Atom | Computed Shift | Experimental Shift | Error | Scaled (Linearly Corrected) Shift | Scaled Error |
|---|---|---|---|---|---|
| 2 | 4.52 | 4.73 | 0.2055 | 4.57 | 0.16 |
| 3-Endo | 1.97 | 1.80 | −0.17 | 2.02 | −0.22 |
| 3-Exo | 1.74 | 1.57 | −0.17 | 1.79 | −0.22 |
| 4-Endo | 1.42 | 1.86 | 0.4357 | 1.48 | 0.38 |
| 4-Exo | 1.78 | 1.88 | 0.1027 | 1.83 | 0.05 |
| 5 | 4.65 | 4.79 | 0.1369 | 4.70 | 0.09 |
| 6-Endo | 1.42 | 1.63 | 0.2057 | 1.48 | 0.15 |
| 6-Exo | 2.56 | 2.50 | −0.0563 | 2.61 | −0.11 |
| 9 (pro-S) | 3.19 | 3.09 | −0.1 | 3.24 | −0.15 |
| 9 (pro-R) | 3.09 | 3.02 | −0.0672 | 3.14 | −0.12 |

TABLE 5

Error correction for computed 4-exo-h2 $^{13}C$ chemical shifts.

| Atom | Computed Shift | Experimental Shift | Error | Scaled (Linearly Corrected) Shift | Scaled Error |
|---|---|---|---|---|---|
| 1 | 61.0 | 52.7 | −8.3 | 54.6 | −1.9 |
| 2 | 89.1 | 81.2 | −7.9 | 84.8 | −3.6 |
| 3 | 30.0 | 26.5 | −3.5 | 24.6 | 1.9 |
| 4 | 33.9 | 29.4 | −4.5 | 29.2 | 0.2 |
| 5 | 83.9 | 77.4 | −6.5 | 78.1 | −0.7 |
| 6 | 45.1 | 44.1 | −1.0 | 44.5 | −0.4 |
| 7 | 187.4 | 174.7 | −12.7 | 173.4 | 1.3 |
| 8 | 182.7 | 169.0 | −13.7 | 168.5 | 0.5 |
| 9 | 41.2 | 37.5 | −3.7 | 44.2 | −0.1 |

TABLE 6

Error correction for computed 4-endo $^1$H chemical shifts.

| Atom | Computed Shift | Experimental Shift | Error | Scaled (Linearly Corrected) Shift | Scaled Error |
|---|---|---|---|---|---|
| 2 | 4.80 | 4.83 | 0.03 | 4.70 | 0.13 |
| 3 | 6.60 | 6.36 | −0.24 | 6.40 | −0.04 |
| 4 | 7.01 | 6.66 | −0.35 | 6.79 | −0.13 |
| 5 | 5.14 | 5.2 | 0.06 | 5.02 | 0.18 |
| 6-endo | 2.07 | 2.07 | 0.00 | 2.13 | −0.06 |
| 6-exo | 1.99 | 2.05 | 0.06 | 2.05 | 0.00 |
| 9 (pro-S) | 3.18 | 3.08 | −0.10 | 3.17 | −0.09 |
| 9 (pro-R) | 3.20 | 3.2 | 0.00 | 3.20 | 0.00 |

TABLE 7

Error correction for computed 4-exo-h2 $^{13}$C chemical shifts.

| Atom | Computed Shift | Experimental Shift | Error | Scaled (Linearly Corrected) Shift | Scaled Error |
|---|---|---|---|---|---|
| 1 | 57.4 | 49.8 | −7.6 | 52.2 | −2.4 |
| 2 | 93.4 | 86.4 | −7.0 | 86.0 | 0.4 |
| 3 | 141.4 | 130.5 | −10.9 | 131.0 | −0.5 |
| 4 | 149.1 | 138.5 | −10.6 | 138.2 | 0.3 |
| 5 | 86.5 | 80.0 | −6.5 | 79.5 | 0.5 |
| 6 | 44.7 | 41.7 | −3.0 | 40.3 | 1.4 |
| 7 | 186.3 | 173.5 | −12.8 | 173.1 | 0.4 |
| 8 | 182.9 | 169.5 | −13.4 | 169.9 | −0.4 |
| 9 | 47.1 | 42.7 | −4.4 | 42.5 | 0.2 |

TABLE 8

Error correction for computed 4-exo $^1$H chemical shifts.

| Atom | Computed Shift | Experimental Shift | Error | Scaled (Linearly Corrected) Shift | Scaled Error |
|---|---|---|---|---|---|
| 2 | 5.01 | 5.11 | 0.10 | 4.88 | 0.23 |
| 3 | 6.84 | 6.48 | −0.36 | 6.59 | −0.11 |
| 4 | 7.08 | 6.71 | −0.37 | 6.82 | −0.11 |
| 5 | 5.18 | 5.26 | 0.08 | 5.04 | 0.22 |
| 6-endo | 1.39 | 1.53 | 0.14 | 1.50 | 0.03 |
| 6-exo | 2.78 | 2.71 | −0.07 | 2.79 | −0.08 |
| 9 (pro-S) | 3.00 | 2.77 | −0.23 | 3.00 | −0.23 |
| 9 (pro-R) | 2.68 | 2.76 | 0.08 | 2.70 | 0.06 |

TABLE 9

Error correction for computed 4-exo-h2 $^{13}$C chemical shifts.

| Atom | Computed Shift | Experimental Shift | Error | Scaled (Linearly Corrected) Shift | Scaled Error |
|---|---|---|---|---|---|
| 1 | 58.0587 | 49.70 | −8.4 | 52.8 | −3.1 |
| 2 | 90.7399 | 83.00 | −7.7 | 82.8 | 0.2 |
| 3 | 143.1034 | 133.20 | −9.9 | 130.8 | 2.4 |
| 4 | 151.533 | 140.60 | −10.9 | 138.5 | 2.1 |
| 5 | 86.2166 | 79.60 | −6.6 | 78.6 | 1.0 |
| 6 | 43.6927 | 38.50 | −5.2 | 39.7 | −1.2 |
| 7 | 187.6446 | 175.10 | −12.5 | 171.6 | 3.5 |
| 8 | 182.777 | 160.00 | −22.8 | 167.1 | −7.1 |
| 9 | 43.2746 | 41.40 | −1.9 | 39.3 | 2.1 |

G. Discussion

The reaction of IA (1) with various furans was investigated. A hallmark of furans as participants in DA cycloaddition chemistry is the fact that the enthalpic change upon formation of the DA adduct is not nearly as favorable as is the case for more typical dienes. This is because loss of the furan aromatic resonance stabilization accompanies this class of cycloaddition. An important consequence of these thermodynamic facts is that DA adducts derived from furans have only rarely been accessed with sufficient efficiency to be useful in sustainable materials applications (Mahmoud, E., et al., *Green Chem.* 2014, 16, 167-175; Shiramizu, M., Toste, F. D., *Chem. Eur. J.* 2011, 17, 12452-12457; Williams, C. L., et al., *ACS Catal.* 2012, 2, 935-939; Pacheco, J. J., Davis, M. E., *Proceedings of the National Academy of Sciences* 2014, 111, 8363-8367). As demonstrated herein anhydride opening along with crystal lattice forces, as enthalpic driving forces, can overcome otherwise sub-optimal thermodynamic parameters of furan DA reactions. Specifically, furfuryl alcohol (FA, 2) and IA (1) form a crystalline adduct, the lactone acid 14 (Scheme 2A), that drives the overall process to high conversion.

The reactions between IA (1) and a variety of simple furans, starting with furan (3) itself were first investigated. In one experiment IA was dissolved in 20 equivalents of furan and held at ambient temperature. Aliquots were periodically withdrawn and dissolved in $CDCl_3$ to monitor the progress of reaction. It was important in this kind of analysis that the spectral data be recorded soon after sample preparation, because the retro-Diels-Alder reaction was also operative at room temperature, and dilution (here, from neat to NMR sample concentration) shifts the equilibrium composition of any bimolecular to unimolecular process toward the starting pair of reactants (here, 1+3). Two diastereomeric products, 4-endo and 4-exo, are produced (FIG. 12A and Table 10, entry 1). Even at early time points, the formation of these two products were observed at nearly identical rates. After 40 hours the system had essentially reached its equilibrium state that is comprised of a ratio of 73% of the initial IA (1) and 27% of the sum of the two DA adducts. At equilibrium, there was a very slight predominance of 4-endo over the amount of 4-exo. These diastereomeric DA adducts were sufficiently stable to be isolable by rapid chromatographic separation on silica gel, even though some retro-DA reaction was occurring as the solutions were being manipulated. Isolated solid-state samples of each isomer were considerably more stable. Upon dissolution in $CDCl_3$ or $C_6D_6$, each isomer began to slowly revert to 1 and 3 (ca. 50% conversion after 6 h), consistent with the rate of their formation and final equilibrium ratios.

TABLE 10

Reactions of itaconic anhydride (1) with the series of furan derivatives 3, 6, 8, and 10 (20 equiv) at ambient temperature

| entry | 20:1 molar ratio | endo | exo | equil. conv. (isomer ratio) [$t_{1/2}$ to equil] |
|---|---|---|---|---|
| 1 | furan (3) + IA 1, neat, r.t. | 4-endo | 4-exo | 27% (1:1) [8 h] |
| 2 | 2,5-dimethylfuran (6) + IA 1, neat, r.t. | 7-endo | 7-exo | ca. 5% (2:1) [0.25 h] |
| 3 | 2-methylfuran (8) + IA 1, neat, r.t. | 9-dist-endo / 9-dist-exo | 9-prox-endo / 9-prox-exo | ca. 13% (11:8:3:1)[a] [10 h] |
| 4 | 2-acetoxymethylfuran (10) + IA 1, neat, r.t. | 11-dist-endo / 11-dist-exo | 11-prox-endo / 11-prox-exo | ca. 20% (8:6:2:1)[b] [24 h] |

The assignment of the diastereomeric relationship within each of 4-exo and 4-endo was initially based on detailed analyses of NMR data as described herein above. This was subsequently confirmed by an X-ray structure of the diacid 5 (FIG. 12B) obtained by catalytic hydrogenation of 4-endo to the derivative 4-endo-h2, that was then hydrolyzed to the crystalline diacid that. Diagnostic features in the 1H NMR spectral data of each diastereomer of 4 were then useful in assessing the relative configuration of the DA adducts prepared from additional furan derivatives (4, 7, 9, and 11 in Table 10).

2,5-Dimethylfuran (6) was the next diene studied, again in an experiment where it was used as the reaction solvent and in ca. 20-fold excess over IA (1). The results are summarized in Table 10 (entry 2). The reaction of 6 with 1 was notably faster than that of furan ($t_{1/2}$~15 min vs. ~8 h at 23° C.), consistent with the greater electron density in diene 6. However, the reaction proceeded to a considerably lower equilibrium conversion (approximately 5%) of the sum of DA adducts 7-endo and 7-exo, that reflects the greater steric compression between the substituents on the spirocyclic carbon and the adjacent (proximal) bridgehead methyl group present in adducts 7 vis-à-vis adducts 4. At an intermediate time point (10 min, approximately 3% conversion), the formation of the major isomer had outpaced that of the minor to the extent of ca. 2:1, a ratio that remained essentially constant.

2-Acetoxymethylfuran (10) was another diene substrate that was studied (Table 10, entry 4). At equilibrium, the IA DA adducts 11 were formed, again to an extent intermediate between that of 4 vs. 7. This was observed to be the slowest of all reactions we studied, consistent with the acetoxymethyl substituent having weakly electron withdrawing character. As was the case for 9, at equilibrium the distal isomers predominated. The assignments of structure to the distal vs. proximal substitution patterns among the isomers of 9 and 11 were based on the difference in coupling patterns of the resonances for the bridgehead protons (at C4) in each (see SI). HMQC and HMBC NMR analyses also were consistent with these assignments.

The reaction between the bio-derived FA (2) and IA (1) was then investigated. Initially, the behavior of an equimolar mixture of this diene/dienophile pair in CDCl$_3$ solution (~1.5 M) was monitored. After being held at 55° C. for 10 minutes, a few percent of total conversion to a mixture of four DA adducts was detected that is consistent with the behavior (rate and ratio) observed for the reaction between the acetate 10 and 1. By analogy, it was presumed that these four compounds were a mixture of the isomeric anhydrides 12 (Scheme 2A). When this reaction solution was examined after 7 days, a new, fifth, component was seen to emerge to the extent of ca. 15% relative to the unconsumed IA (1). The appearance of (i) a broad downfield resonance and (ii) a pair of downfield doublets (δ 4.62 and 4.83, J$_{ab}$=10.8 Hz) in this new, dominant compound suggested that a carboxylic acid lactone had formed; it is reasonable to anticipate a conversion of one of 12-prox-exo or 12-prox-endo to a ring-opened lactone acid by one of the four pathways implied by arrows "a" or "b" in 12-prox-exo or "a'" or "b'" in 12-prox-endo (Scheme 2A). The favorable free energy change associated with anhydride opening provides an additional driving force to help favor the DA adduct(s).

Scheme 2A
Reaction manifold showing the equilibration among 1 + 2, four isomeric anhydrides 12, lactone acids 13 and 14, and mono-furfuryl itaconates 15.

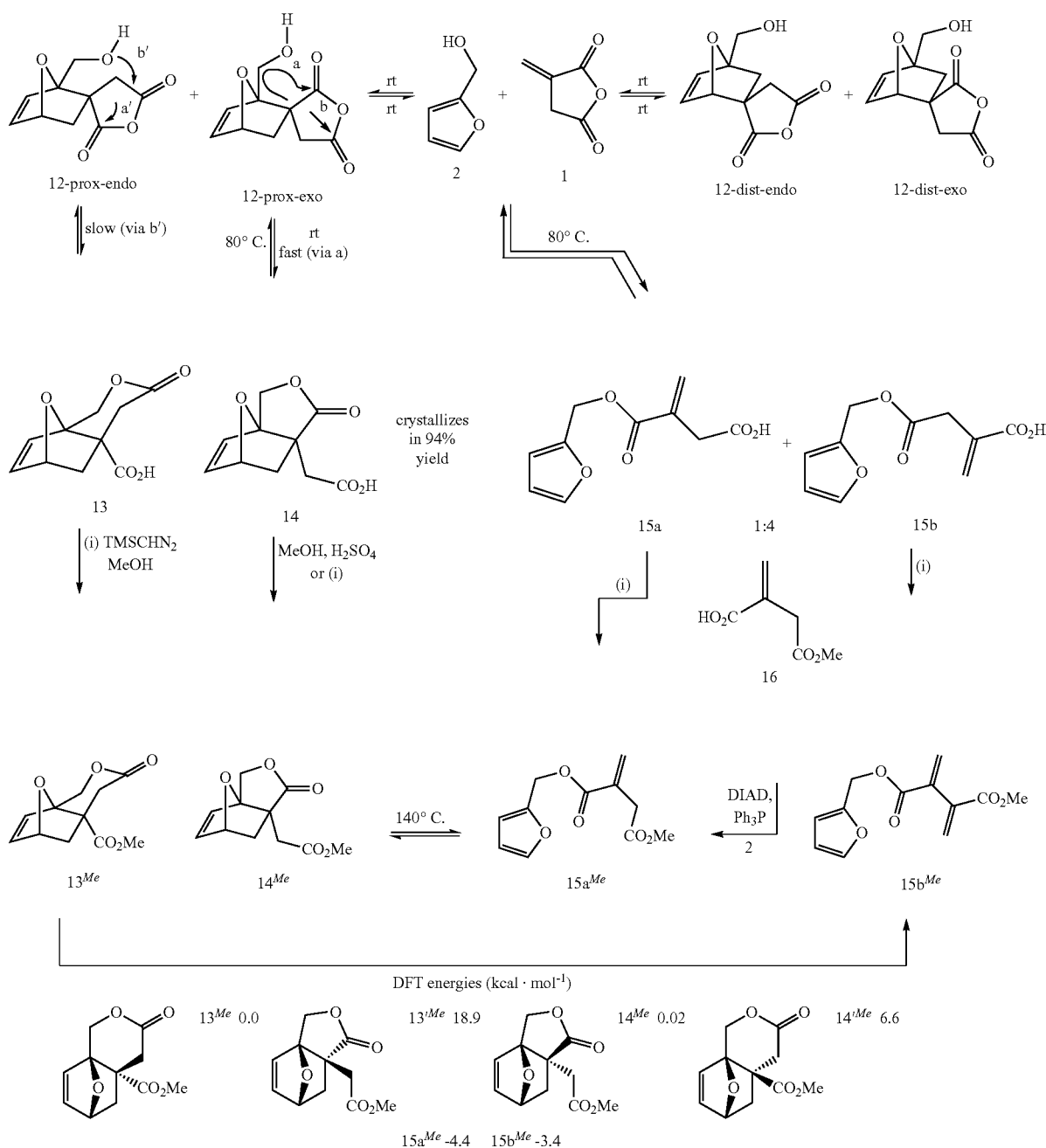

Scheme 2B
DFT free energies [M06-2X/6-31+G(d,p)(SMD:CHCl3)] of the four isomeric lactone acids (methyl esters) from ring opening of 12-prox-endo and 12-prox-exo

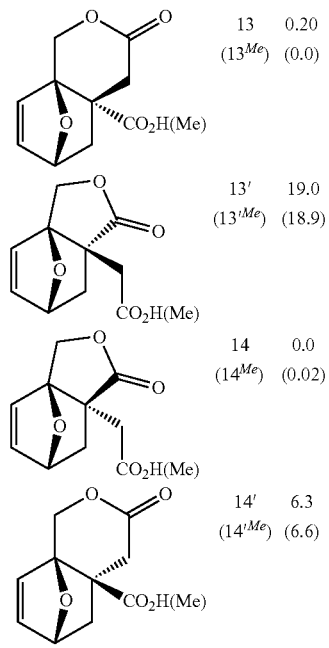

| | | |
|---|---|---|
| 13 | 0.20 | |
| ($13^{Me}$) | (0.0) | |
| 13' | 19.0 | |
| ($13'^{Me}$) | (18.9) | |
| 14 | 0.0 | |
| ($14^{Me}$) | (0.02) | |
| 14' | 6.3 | |
| ($14'^{Me}$) | (6.6) | |

An additional important discovery occurred when an equimolar mixture of 1 and 2 was allowed to react in the bulk. A suspension of solid 1 (95% grade) in liquid 2 (98% grade) at ambient temperature changed over time in consistency. After 3-4 hours the initial heterogeneous slurry could no longer be magnetically stirred; we could identify in the NMR spectrum of an aliquot the presence of all four isomeric anhydrides 12 (Scheme 2A) to the total extent of ca. 5%, along with a significant amount of the same fifth component mentioned in the paragraph above. After 10 h the composition of the bulk reaction mixture was that of a paste, and after 18 h it had turned to a solid mass. This material was comprised of largely a single component, having the same spectral properties as those of the new, fifth component that had appeared after 7 days in the homogenous CDCl$_3$ solution experiment described above. The $^{13}$C NMR spectrum of this compound showed a carbonyl resonance at δ 177.8 ppm, suggestive that it contained a 5-membered butyrolactone ring (J. B. Lambert, et al., J. Org. Chem. 1983, 48, 3982-3985) X-ray diffraction showed the structure to be that of the lactone acid 14, arising therefore from (event "a" in) 12-prox-exo.

Analysis of aliquots from the bulk reaction mixture over time showed the steady-state mixture of the four DA adducts 12 transforming to largely the single component 14, establishing the ready reversibility of each of 12 back to IA (1) and FA (2). The $^1$H NMR spectrum of an aliquot taken from an equimolar mixture after 2 days is shown in FIG. 13. From careful integration the chemical yield for formation of 14 was determined to be 94%. The driving force for the conversion of IA+FA to 14 comes both from (i) the opening of the anhydride as well as (ii) the crystallization of the product from a dynamic, interconverting mixture of multiple components.

A sample removed from the bulk mixture of 1 and 2 after just 30 minutes was immediately chromatographed on silica gel. Small amounts (approximately 1 mg each) of three samples were unearthed, each in <1% yield but each highly informative in various ways. The dilute CDCl$_3$ solution of each of the anhydrides 12-dist-endo and 12-dist-exo, assigned as such by comparative NMR analyses with some of the previous DA adducts, was observed to begin reverting to 1 and 2 at room temperature in a matter of minutes. The third sample proved to be an acid lactone isomeric with 14. It contained ~20% of a second compound whose $^1$H NMR resonances suggested it to be the anhydride 12-prox-endo. Within a day in CDCl$_3$, this anhydride had converted to the same, new acid lactone. By a series of correlation experiments it was concluded that the structure of this new lactone was that of 13, arising by the attack indicated by "b"' in structure 12-prox-endo (FIG. 13, spectrum a).

Monitoring the thermal behavior of a CDCl$_3$ solution of the lactone acid 14 was also informative. At 80° C. formation of a 1:4 mixture of the two mono-furfuryl itaconate esters 15a and 15b (see below for structure assignment) was observed. The formation of 15b cannot arise from direct retro-DA reaction of 14. Instead 14 apparently reverts to 12-prox-exo and, in turn 2 and 1, that then can proceed to the mixture of 15a and 15b. All of these intermediates were detectable through $^1$H NMR monitoring. To probe whether 14 can produce 15a directly by a retro-DA reaction, 14 was converted to the methyl ester $14^{Me}$. This compound proved to be quite stable at 80° C. in CDCl$_3$ and only upon heating to 140° C. in the melt did it finally revert solely to the ester $15a^{Me}$. An authentic sample of $15a^{Me}$ was produced by Mitsunobu esterification reaction between FA (2) and the commercially available mono-methyl itaconate 16. The rate of the retro-DA reaction of $14^{Me}$ suggests that 14 does not proceed directly to 15a. Addition of alcohols IA (1) is known to occur faster at the non-conjugated carbonyl carbon (Cheng, X., et al., Org. Lett. 2014, 16, 1414-1417). When a 1:1 mixture of IA and benzyl alcohol, a DA-silent mimic of FA (2), was heated at 80° C., a similar mixture of analogous mono-benzyl itaconates was formed.

Isomeric lactone acid 13 was converted to the methyl ester $13^{Me}$. Like its analog $14^{Me}$, this ester also showed clean retro-DA behavior when heated neat at 140° C. (partial reversion after 1 min and complete after 5 min). Only the mixed diester $15b^{Me}$ was produced, verifying that 13 embodied a valero- rather than butyrolactone. All told, given the subtle and multi-faceted interplay of kinetic and thermodynamic factors within this array of competitive processes, it is notable that a single metastable adduct (i.e., 14) arises through trivial manipulation and in high yield. Unraveling the process to the extent captured in Scheme 2A required critical interrogation of minor components present in $^1$H NMR spectra at numerous junctures.

With a robust process in hand for producing a 100% bio-derived compound with a novel structure, several transformations with an eye toward production of monomers having potential utility in polymer synthesis were investigated. The reactivity of 14 and $14^{Me}$ was explored under a number of reaction conditions that are either reagent free or use inexpensive reagents, and/or that are amenable to large-scale, and/or that are free of byproduct formation. Such non-limiting reaction types include catalytic hydrogenation, pyrolysis, and simple acid- or base-catalyzed transformations. Scheme 3 summarizes some of these reactions.

Scheme 3
Derivatization reactions of 14, for accessing useful building blocks.

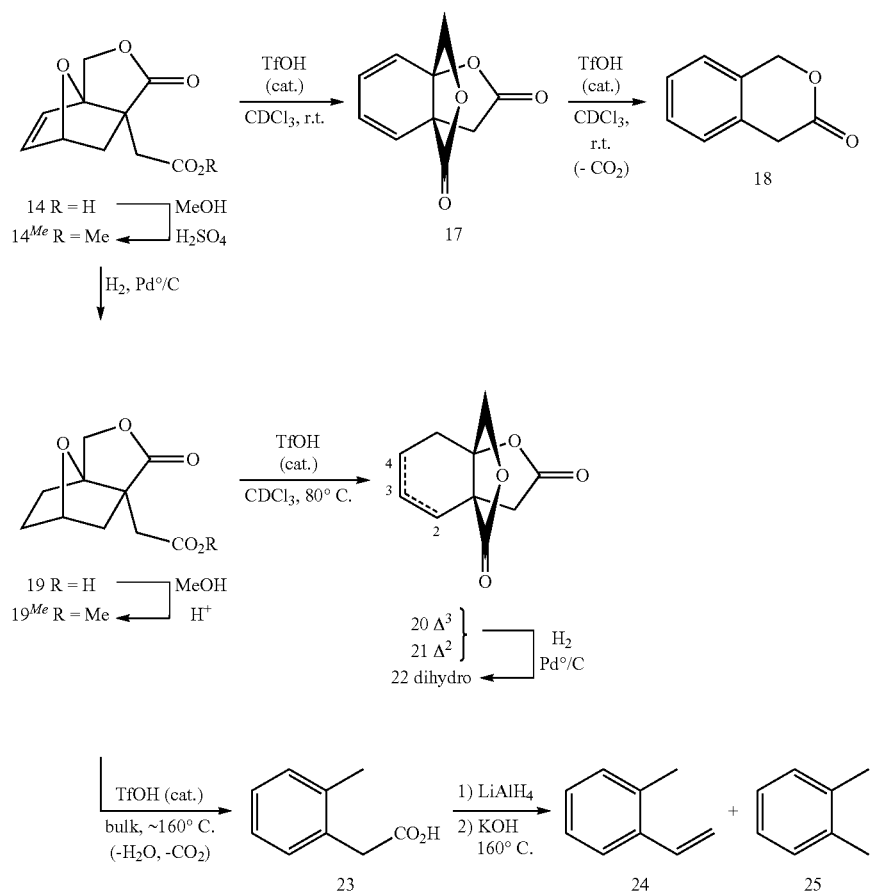

Treatment of either 14 or 14$^{Me}$ at ambient temperature with a strong Brønsted acid (e.g., TfOH), either as a neat sample or in chloroform solution, resulted in loss of water or methanol, respectively, and concomitant formation of the bis-lactone diene 17. The structure of an isolated and purified sample (40% yield) of this interesting dioxapropellane derivative was supported by both 1D and 2D NMR spectroscopic studies. This diene was further converted under the reaction conditions to 3-isochromanone (18); the maximum extent of accumulation of 17 under the conditions we explored was ca. 50%. Isochromenone 18 is known to polymerize in a Friedel-Crafts sense when a neat sample is heated at 120° C. in the presence of TfOH (Suzuki, A. et al., *J. Polym. Sci., Part A: Polym. Chem.* 2009, 47, 2214-2218).

Either 14 or 14$^{Me}$ could be smoothly reduced by dihydrogen over palladium on carbon to give 19 or 19$^{Me}$, respectively. The former (acid) could also be converted to the latter (ester) by Fischer esterification. Upon treatment again with TfOH in chloroform solution, now at 80° C., either of 19 or 19$^{Me}$ could be dehydrated to the dilactone mono-enes 20 and 21. These reactions were slower than those of the oxanorbornenes 14/14$^{Me}$ to 17, presumably because the ring-opening of the ether bridge no longer results in formation of an allylic carbenium ion. When either of 19 or 19$^{Me}$ was heated in the bulk with TfOH at 160° C., 20 and 21 were again produced, but further reaction ensued—namely, the production of 2-methylphenylacetic acid (23), accompanied by loss of CO$_2$. Arene 23 was isolated in 77% yield following chromatographic purification. A sample of this acid 1 was reduced with lithium aluminum hydride to the corresponding phenethanol derivative and then dehydrated at 160° C. over molten KOH to give a mixture of 2-methylstyrene (24) and o-xylene (25). Alternatively, the esters can be reduced to alcohols by hydrogen gas using the Milstein/Saudan family of catalysts (Zhang, J., et al., *Angew. Chem. Int. Ed.* 2006, 45, 1113-1115; Saudan, L. A., et al., *Angew. Chem. Int. Ed.* 2007, 46, 7473-7476). None of the transformations described in Scheme 3, including the dehydration of 2-(2-methylphenyl)ethanol, has been optimized.

In addition, a ring-opening metathesis polymerization (ROMP) of the monomer 14$^{Me}$ (Scheme 4) was performed. The Grubbs-III initiator induced polymerization of a methylene chloride solution of the strained alkene 14$^{Me}$. An analogous ROMP was recently reported for 27, the DA adduct between cyclopentadiene and dimethyl itaconate (Winkler, M., et al., *Macromolecules* 2015, 48, 1398-1403). In contrast to the behaviour of norbornene derivative 27, that lacked bridgehead substituents, an initiator diene (diethyl diallylmalonate) was added to promote the ROMP of 14$^{Me}$. MALDI analysis suggested that the majority of polymer molecules were both initiated and terminated with =CH$_2$ groups. Presumably the bulk of the quaternized bridgehead carbon in 14$^{Me}$ provides a steric barrier that is best accommodated by methylidene moieties (from ethylene) in the first and/or second steps of propagation.

Scheme 4
ROMP of methyl ester lactone 14$^{Me}$.

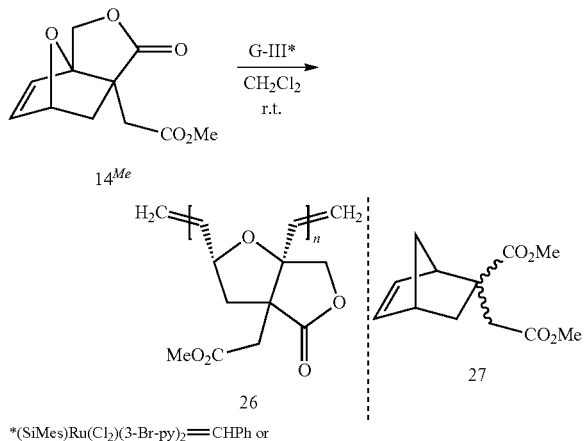

*(SiMes)Ru(Cl$_2$)(3-Br-py)$_2$=CHPh or dichloro[1,3-bis{2,4,6-trimethylphenyl)-2-imidazolidinylidene}-(benzylidene)bis(3-bromopyridine)ruthenium(II)

Thus, lactone acid 14 was produced in high yield (94%) under efficient and mild reaction conditions (e.g., 1:1 mixture of IA (1) and FA (2), neat, ambient temperature). Moreover, 14 can be readily transformed into a variety of derivatives (17-25, Scheme 3) that have potential non-limiting utility as monomers in sustainable polymer synthesis (e.g., compound 26, Scheme 4).

Example 2. Preparation of (±)-2-(2-((3aR,6R)-1-Oxo-6,7-dihydro-3H-3a,6-epoxyisobenzofuran-7a(1H)-yl)acetoxy)ethyl acrylate (100)

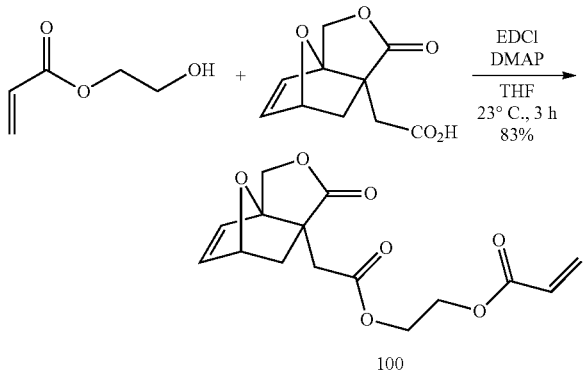

Hydroxyethyl acrylate (147 mg, 1.27 mmol) was dissolved in THF (10 mL). Acid 14 (280 mg, 1.33 mmol), EDCI (293 mg, 1.52 mmol), and DMAP (77 mg, 0.64 mmol) were added, resulting in a suspension that was stirred at room temperature for 3 h. Dilute aqueous HCl was added and the resulting mixture was extracted with 4 mL of methylene chloride. The organic layer was dried over Na$_2$SO$_4$ and concentrated in vacuo. The residue was purified by flash column chromatography on silica gel (1:1 hexanes: EtOAc elution) to give 100 (325 mg, 1.05 mmol, 83%) as a colorless liquid.

$^1$H NMR (500 MHz, CDCl$_3$) δ 6.58 (dd, J=5.8, 1.7 Hz, 1H), 6.50 (d, J=5.8 Hz, 1H), 6.47 (dd, J=17.3, 1.3 Hz, 1H), 6.16 (dd, J=17.3, 10.5 Hz, 1H), 5.90 (dd, J=10.5, 1.3 Hz, 1H), 5.06 (dd, J=4.7, 1.7 Hz, 1H), 4.82 (d, J=10.8 Hz, 1H), 4.63 (d, J=10.8 Hz, 1H), 4.43-4.33 (m, 4H), 2.56 (dd, J=12.3, 4.7 Hz, 1H), 2.56 (d, J=14.7 Hz, 1H), 2.37 (d, J=14.7 Hz, 1H), and 1.52 (d, J=12.3 Hz, 1H).

$^{13}$C NMR (125 MHz, CDCl$_3$) δ 177.0, 169.3, 166.0, 138.3, 131.7, 130.7, 128.0, 94.1, 78.8, 68.7, 63.1, 62.0, 52.1, 39.9, and 36.7.

IR (neat): 2959, 1773, 1726, 1410, 1325, 1274, 1179, 1133, 998, 969, 854, and 810 cm$^{-1}$.

HRMS (ESI-TOF): Calcd for C$_{15}$H$_{16}$NaO$_7$ [M+Na$^+$] requires 331.0788; found 331.0780.

Example 3. Preparation of (±)-2-(2-((3aR,6S)-1-Oxotetrahydro-3H-3a,6-epoxyisobenzofuran-7a(1H)-yl)acetoxy)ethyl acrylate (200)

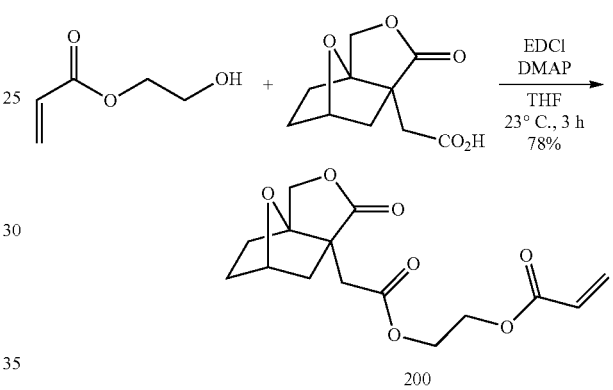

Hydroxyethyl acrylate (154 mg, 1.33 mmol) was dissolved in THF (10 mL). Acid 19 (280 mg, 1.33 mmol), EDCI (303 mg, 1.58 mmol), and DMAP (83 mg, 0.69 mmol) were added, resulting in a suspension that was stirred at room temperature for 3 h. Dilute aqueous HCl was added and the resulting mixture was extracted with 4 mL of methylene chloride. The organic layer was dried over Na$_2$SO$_4$ and concentrated in vacuo. The residue was purified by flash column chromatography on silica gel (1:1 hexanes: EtOAc elution) to give 200 (320 mg, 1.03 mmol, 78%) as a colorless liquid.

$^1$H NMR (500 MHz, CDCl$_3$) δ 6.45 (dd, J=17.3, 1.4 Hz, 1H), 6.14 (dd, J=17.3, 10.5 Hz, 1H), 5.88 (dd, J=10.5, 1.4 Hz, 1H), 4.57 (t, J=5.3 Hz, 1H), 4.53 (d, J=10.4 Hz, 1H), 4.50 (d, J=10.5 Hz, 1H), 4.43-4.33 (m, 4H), 2.91 (d, J=15.3 Hz, 1H), 2.53 (d, J=15.3 Hz, 1H), 2.42 (ddd, J=12.6, 5.0, 2.3 Hz, 1H), 2.00 (dddd, J=14.9, 12.1, 5.7, 2.8 Hz, 1H), 1.93 (ddd, J=12.1, 8.7, 3.2 Hz, 1H), 1.75 (ddd, J=12.2, 12.2, 5.6 Hz, 1H), 1.75 (d, J=12.6 Hz, 1H), and 1.62 (ddd, J=12.4, 8.7, 5.6 Hz, 1H).

$^{13}$C NMR (125 MHz, CDCl$_3$) δ 178.6, 169.5, 165.9, 131.7, 127.9, 91.8, 76.4, 69.1, 63.0, 62.0, 53.1, 44.9, 39.1, 29.0, and 24.6.

IR (neat): 2963, 1773, 1727, 1410, 1327, 1271, 1189, 1174, 1127, 1006, 964, 850, and 811 cm$^{-1}$.

HRMS (ESI-TOF): Calcd for C$_{15}$H$_{18}$NaO$_7$ [M+Na$^+$] requires 333.0945; found 333.0947.

Example 4. Preparation of (±)-2-(2-((3aR,6S)-1-Oxotetrahydro-3H-3a,6-epoxyisobenzofuran-7a(1H)-yl)acetoxy)ethyl methacrylate (300)

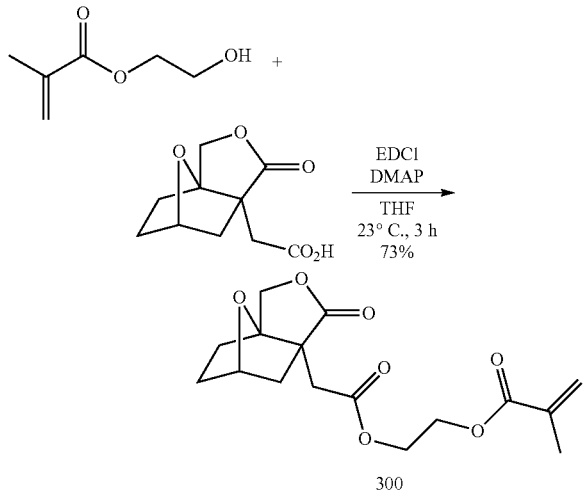

Hydroxyethyl acrylate (173 mg, 1.33 mmol) was dissolved in THF (10 mL). Acid 19 (280 mg, 1.33 mmol), EDCl (290 mg, 1.51 mmol), and DMAP (86 mg, 0.70 mmol) were added, resulting in a suspension that was stirred at room temperature for 3 h. Dilute aqueous HCl was added and the resulting mixture was extracted with 4 mL of methylene chloride. The organic layer was dried over $Na_2SO_4$ and concentrated in vacuo. The residue was purified by flash column chromatography on silica gel (1:1 hexanes: EtOAc elution) to give 300 (315 mg, 1.03 mmol, 73%) as a colorless liquid.

$^1$H NMR (500 MHz, $CDCl_3$) δ 6.11 (dq, J=1.5, 1.0 Hz, 1H), 5.58 (dq, J=1.5, 1.5 Hz, 1H), 4.54 (t. J=5.3 Hz, 1H), 4.50 (d, J=10.5 Hz, 1H), 4.46 (d, J=10.5 Hz, 1H), 4.36-4.29 (m, 4H), 2.88 (d, J=15.3 Hz, 1H), 2.49 (d, J=15.3 Hz, 1H), 2.39 (ddd, J=12.6, 5.0, 2.3 Hz, 1H), 1.97 (tdd, J=10.9, 5.2, 2.2 Hz, 1H), 1.92 (dd, J=1.5, 1.0 Hz, 3H), 1.89 (ddd, J=12.1, 8.7, 3.2 Hz, 1H), 1.72 (ddd, J=12.2, 12.2, 5.6 Hz, 1H), 1.75 (d, J=12.6 Hz, 1H), and 1.59 (ddd, J=12.5, 8.7, 5.6 Hz, 1H).

$^{13}$C NMR (125 MHz, $CDCl_3$) δ 178.6, 169.5, 167.1, 135.9, 126.3, 91.8, 76.4, 69.1, 63.1, 62.2, 53.1, 44.9, 39.2, 29.0, 24.6, and 18.3.

IR (neat): 2960, 1773, 1719, 1458, 1322, 1297, 1162, 1129, 1008, and 938 $cm^{-1}$.

HRMS (ESI-TOF): Calcd for $C_{16}H_{20}NaO_7$ [M+Na$^+$] requires 347.1101; found 347.1111.

Example 5. AIBN Initiated Free Radical Polymerization of Compound 100

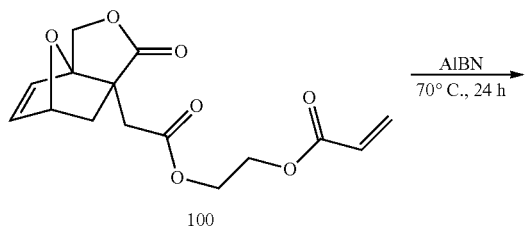

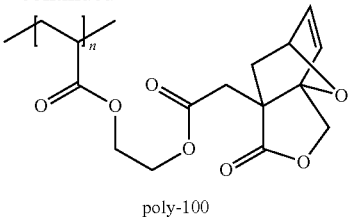

poly-100

A solution of 100 (80 mg, 0.260 mmol) and 2,2'-(diazene-1,2-diyl)bis(2-methylpropanenitrile) (AIBN, 3.7 mg, 0.024 mmol) was prepared. After the full dissolution of AIBN in the acrylate, the solution was transferred into a 5 mL round-bottom flask and degassed through a series of three freeze-pump-thaw cycles and then sealed under vacuum. The reaction mixture was heated at 70° C. for 24 h. The reaction mixture was allowed to cool to ambient temperature to give a clear disk that was insoluble in all common solvents, suggestive of a cross-linked structure.

IR (neat, selected peaks): 2959, 1773, 1722, 1176, and 968 $cm^{-1}$.

Figure 19:
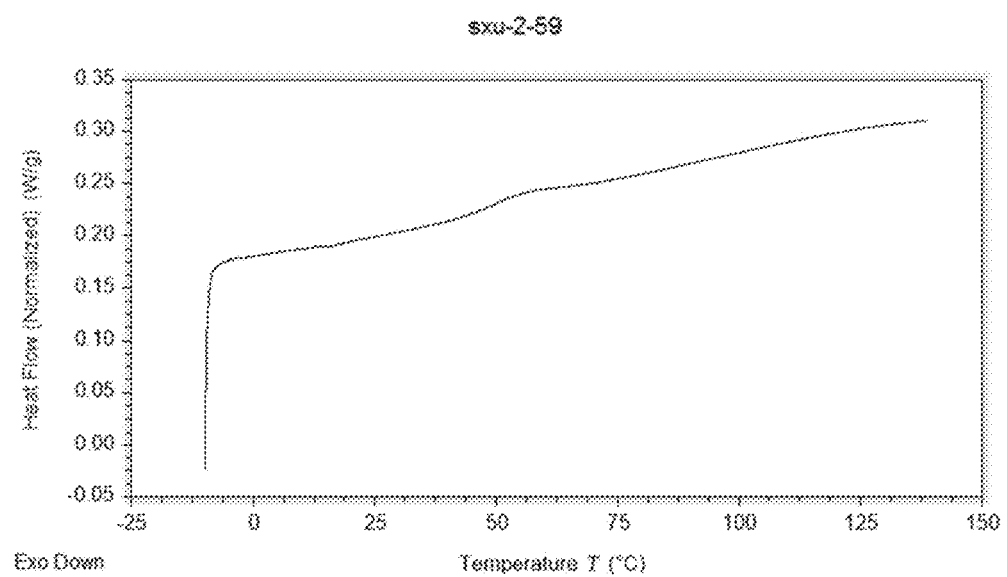
FIG. 19 shows the Tg for the material prepared at Example 5.

DSC $T_g$=50° C. (See FIG. 19)

Example 6. AIBN Initiated Free Radical Polymerization of Compound 200

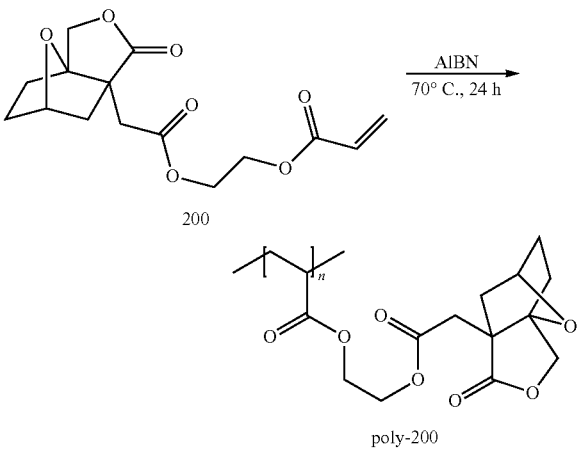

poly-200

A solution of 200 (160 mg, 0.516 mmol) and 2,2'-(diazene-1,2-diyl)bis(2-methylpropanenitrile) (AIBN, 4.1 mg, 0.027 mmol) was prepared. After the full dissolution of AIBN in the acrylate, the solution was transferred into a 5 mL round-bottom flask and degassed through a series of three freeze-pump-thaw cycles and sealed under vacuum. The reaction mixture was heated at 70° C. for 24 h. The reaction mixture was allowed to cool to ambient temperature and a portion of the contents was analyzed by $^1$H NMR spectroscopy.

$^1$H NMR (500 MHz, $d_6$-DMSO): δ 4.60-4.50 (m, 2.0H), 4.50-4.42 (m, 1.0H), 4.30-4.10 (m, 4.0H), 2.35-2.20 (m, 1.1H), 2.15-2.06 (m, 1.5H), 1.90-1.75 (m, 3.0H), and 1.72-1.58 (m, 3.5H).

IR (neat, selected peaks): 2998, 2939, 1778, 1461, 1383, 1183, and 1149 $cm^{-1}$.

Example 7. RAFT Polymerization of Compound 200

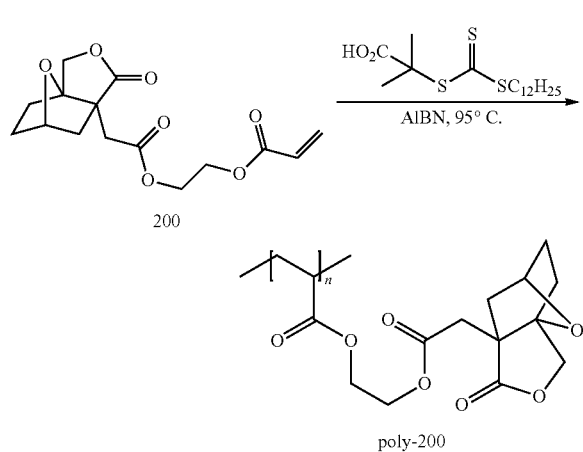

AIBN (0.08 equiv, 0.16 mg, 1.0 μmol) was added to a 10 mL Schlenk flask. 2-{[(Dodecylthio)carbonothioyl]thio}-2-methylpropanoic acid (DDMAT, 1.0 equiv, 14.2 mg, 39.2 μmol) and acrylate 200 (18 equiv, 224 mg, 0.723 mmol) were added. The headspace was degassed through several freeze-pump-thaw cycles, under static vacuum, until bubbling no longer was observed during thawing. Nitrogen was then admitted and the flask was heated in an oil bath held at 95° C. Aliquots were periodically withdrawn under nitrogen flow. $^1$H NMR analysis of the crude aliquots indicated that >94% conversion of the monomer had been achieved after 2 days. The flask was allowed to cool to ambient temperature, the residue was dissolved in THF, and the polymer was precipitated by addition of the THF solution to swirled methanol held at 0° C. The resulting slurry was cooled (−20° C.), centrifuged, decanted, and rendered free of solvent under vacuum overnight at 70° C. to provide 195 mg of poly-200 (87% yield).

$^1$H NMR (500 MHz, d$_6$-acetone): δ 4.62-4.54 (m, 2.1H), 4.51-4.45 (m, 1H), 4.38-4.28 (m, 3.8H), 2.29-2.23 (m, 1H), 2.05-1.99 (m, 1H), 1.94-1.87 (m, 2.7H), and 1.83-1.68 (m, 3.3H).

IR (neat, selected peaks): 2957, 1770, 1729, 1159, 1122, and 1001 cm$^{-1}$.

Figure 20:
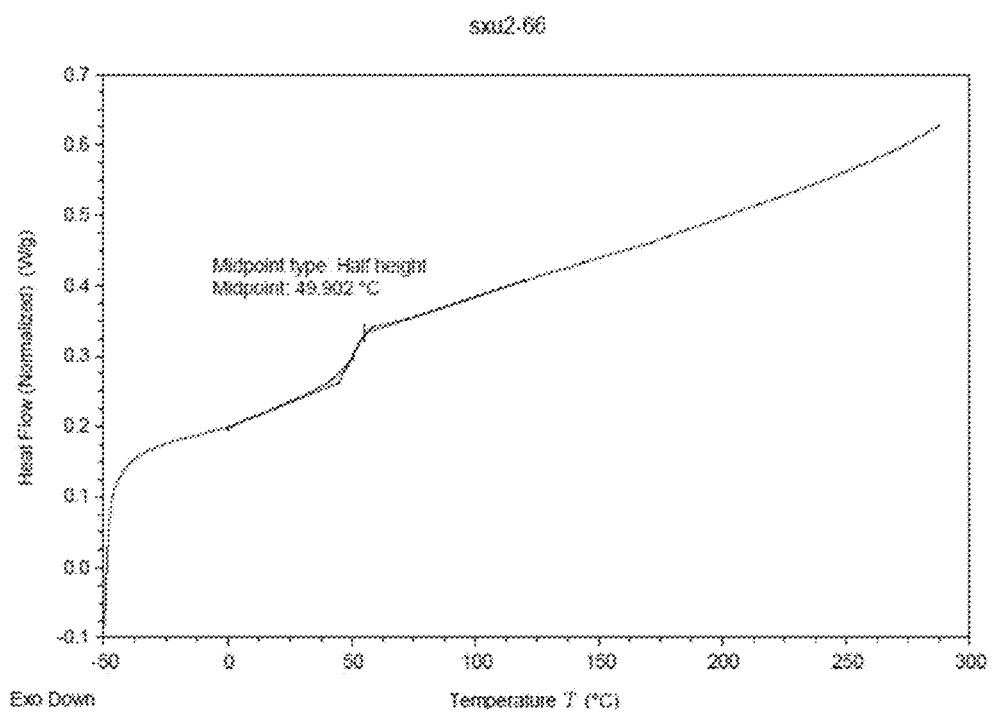
FIG. 20 shows the Tg for the material prepared at Example 7.

DSC $T_g$=50° C. (See FIG. 20)

Figure 21:
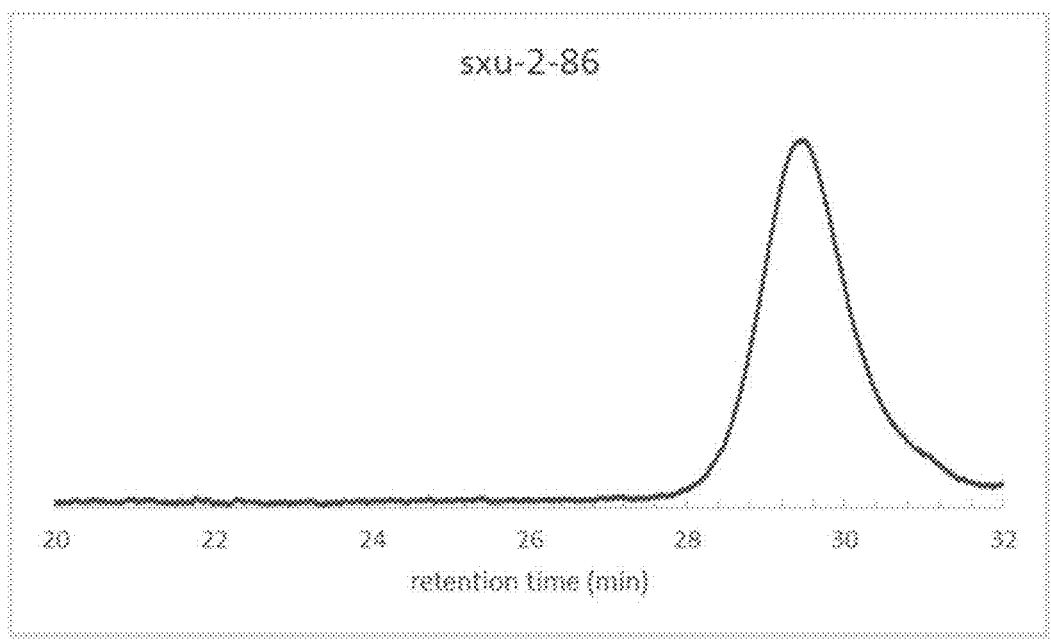
FIG. 21 shows the retention time for the material prepared at Example 7.

SEC PS-GPC (THF): $M_n$=3,630 g mol$^{-1}$, $M_w$=3,830 g mol$^{-1}$, Đ=1.06 (See FIG. 21)

Example 8. AIBN Initiated Free Radical Polymerization of Compound 300

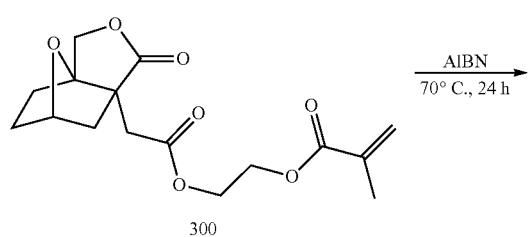

A solution of the methacrylate ester 300 (70 mg, 0.216 mmol) and 2,2'-(diazene-1,2-diyl)bis(2-methylpropanenitrile) (AIBN, 1.1 mg, 6.7 μmol) was prepared. After the full dissolution of AIBN in the methacrylate, the solution was transferred into a 5 mL round-bottom flask and degassed through a series of three freeze-pump-thaw cycles and sealed under vacuum. The reaction mixture was heated at 70° C. for 24 h. The reaction mixture was allowed to cool to ambient temperature to give an insoluble, clear disk.

IR (neat, selected peaks): 2960, 1770, 1724, 1188, 1169, and 1000 cm$^{-1}$.

Figure 22:
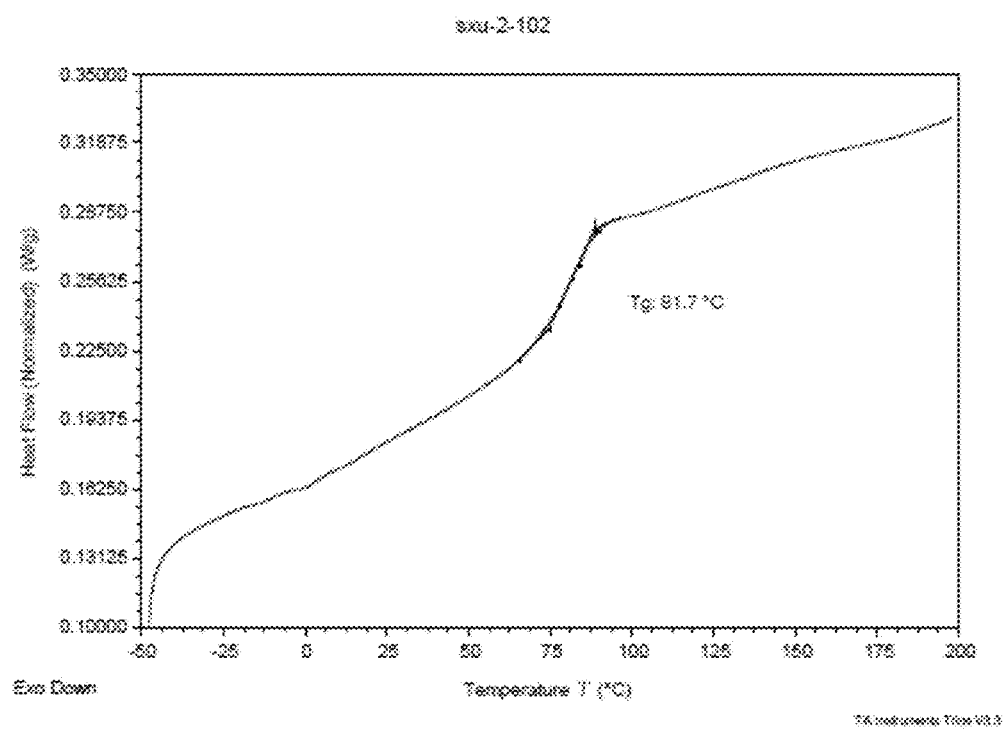
FIG. 22 shows the Tg for the material prepared at Example 8.

DSC $T_g$=82° C. (See FIG. 22)

Example 9. Preparation of (±)-3-((3aR,6R)-1-Oxo-6,7-dihydro-3H-3a,6-epoxyisobenzofuran-7a(1H)-yl)propanoic acid (29)

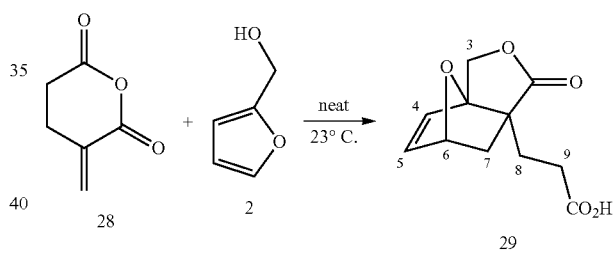

Homoitaconic anhydride (28, 280 mg, 2.22 μmol) was suspended in furfuryl alcohol (2, 217 mg, 2.21 μmol) and this slurry was allowed to stir (magnetically) at ambient temperature. After about 17 hours, the suspension had turned to a light yellow solution. The residue was purified by flash column chromatography on SiO$_2$ (hexanes/EtOAc, 3:1) to give 29 (245 mg, 50%) as a colorless oil.

$^1$H NMR (500 MHz, acetone-d$_6$) δ 11.05-10.35 (br s, 1H, COOH), 6.64 (d, J=5.8 Hz, 1H, H4), 6.62 (dd, J=5.9, 1.5 Hz, 1H, H5), 5.04 (dd, J=4.8, 1.0 Hz, 1H, H6), 4.94 (d, J=11.0 Hz, 1H, C3H$_a$H$_b$), 4.55 (d, J=11.0 Hz, 1H, C3H$_a$H$_b$), 2.49 (ddd, J=16.8, 11.3, 5.5 Hz, 1H, C9H$_a$H$_b$), 2.36 (ddd, J=16.8, 11.0, 5.3 Hz, 1H, C9H$_a$H$_b$), 2.28 (dd, J=11.8, 4.8 Hz, 1H, C7H$_{exo}$H$_{endo}$), 1.94 (ddd, J=14.0, 11.0, 5.5 Hz, 1H, C8H$_a$H$_b$), 1.43 (ddd, J=14.0, 11.3, 5.2 Hz, 1H, C8H$_a$H$_b$), and 1.38 (d, J=11.8 Hz, 1H, C7H$_{exo}$H$_{endo}$).

All publications, patents, and patent documents are incorporated by reference herein, as though individually incorporated by reference. The invention has been described with reference to various specific and preferred embodiments and techniques. However, it should be understood that many variations and modifications may be made, while remaining within the spirit and scope of the invention.

What is claimed is:

1. A compound of formula III or a salt thereof:

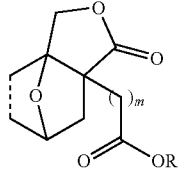

III wherein: m is 1 or 2; R is H, $(C_1$-$C_6)$alkyl, or $(C_3$-$C_6)$cycloalkyl; and the dashed bond is a single bond or double bond.

2. A compound of formula I or a salt thereof, or a compound of formula II or an enantiomer thereof:

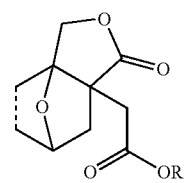

I

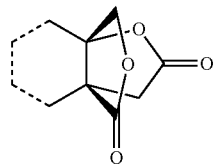

II wherein R is R is H, $(C_1$-$C_6)$alkyl, or $(C_3$-$C_6)$cycloalkyl and each dashed bond is a single bond or double bond provided no two double bonds of the compound of formula II are cumulated.

3. The compound of claim 2 that is a compound of formula Ia or a salt thereof or an enantiomer thereof or a salt thereof, or a compound of formula II or an enantiomer thereof:

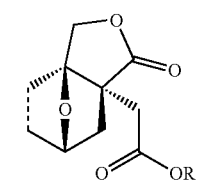

Ia

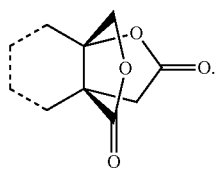

II

4. The compound of claim 2 that is a compound of formula Ia:

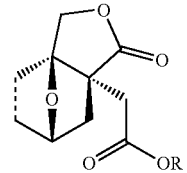

Ia or a salt thereof or an enantiomer or a salt thereof.

5. The compound of claim 2 that is a compound of formula Ic or Id:

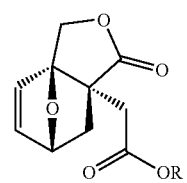

Ic

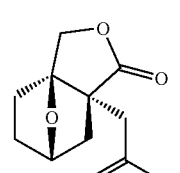

Id or a salt thereof or an enantiomer or a salt thereof.

6. The compound of claim 2 that is a compound of formula Ic or Id:

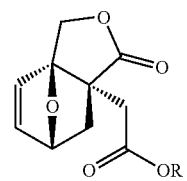

Ic

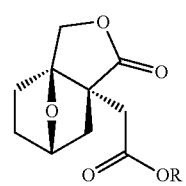

Id or an enantiomer thereof.

7. The compound of claim 2 that is a compound of formula II:

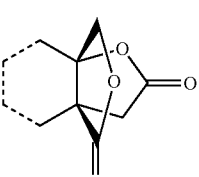

II or an enantiomer thereof.

8. The compound of claim 2 that is:
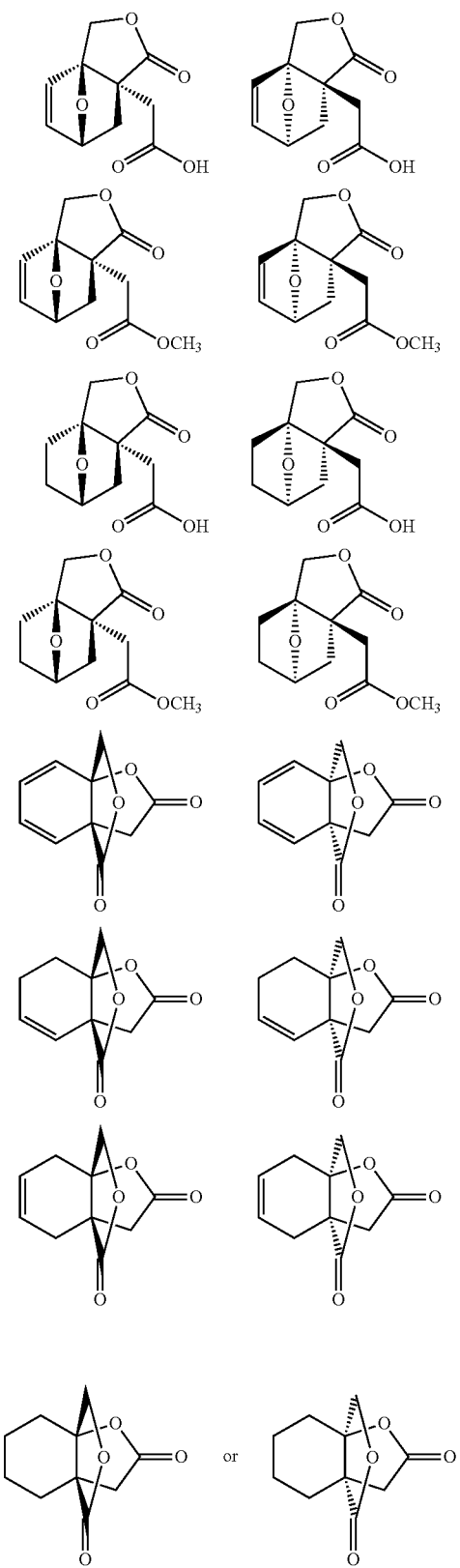
or a salt thereof.
9. The compound of claim 2 that is:
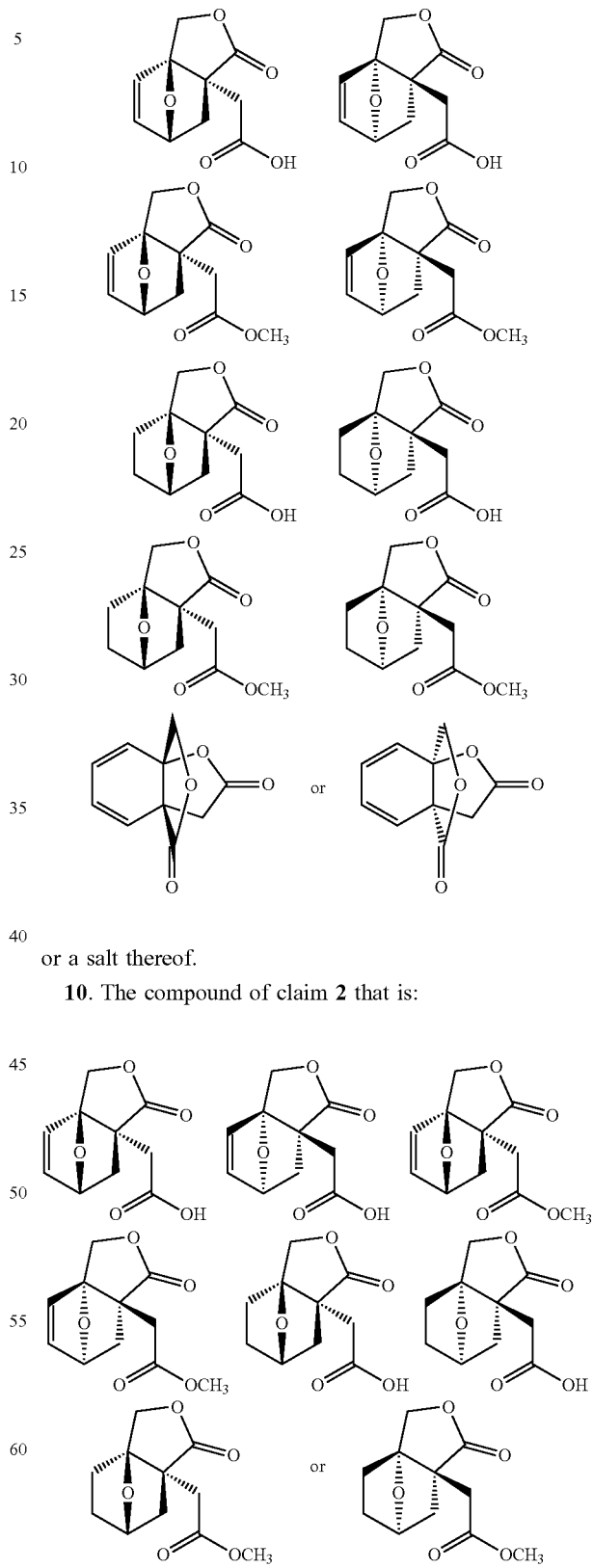
or a salt thereof.
10. The compound of claim 2 that is:
or a salt thereof.

11. The compound of claim 2 that is:

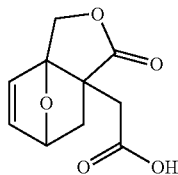 [SMILES: O=C(O)CC12CC3C=CC1(COC2=O)O3]

or a salt thereof.

12. The compound of claim 2 that is:

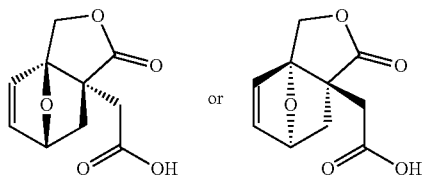 [SMILES: O=C(O)C[C@]12C[C@@H]3C=C[C@@]1(COC2=O)O3 ; O=C(O)C[C@@]12C[C@H]3C=C[C@]1(COC2=O)O3] or or a salt thereof.

13. The compound of claim 2 that is:

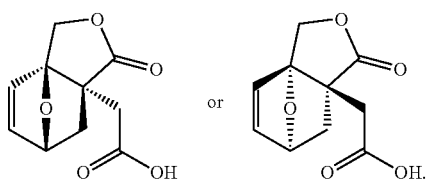 [SMILES: O=C(O)C[C@]12C[C@@H]3C=C[C@@]1(COC2=O)O3 ; O=C(O)C[C@@]12C[C@H]3C=C[C@]1(COC2=O)O3] or

14. A composition comprising:

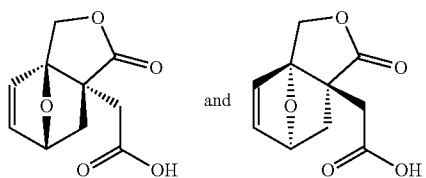 [SMILES: O=C(O)C[C@]12C[C@@H]3C=C[C@@]1(COC2=O)O3 ; O=C(O)C[C@@]12C[C@H]3C=C[C@]1(COC2=O)O3] and or salts thereof.

15. A method for preparing a compound of claim 2 which is a compound of formula Ic1:

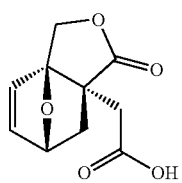

Ic1 or a salt thereof or an enantiomer or a salt thereof, comprising converting furfuryl alcohol to the compound of formula Ic1 or a salt thereof or an enantiomer or a salt thereof.

16. A method for preparing a compound of claim 2 which is a compound of formula Ic1:

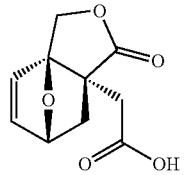

Ic1 or a salt thereof or an enantiomer or a salt thereof, comprising converting itaconic anhydride to the compound of formula Ic1 or a salt thereof or an enantiomer or a salt thereof.

17. A method for preparing a compound of claim 2 which is a compound of formula IIa:

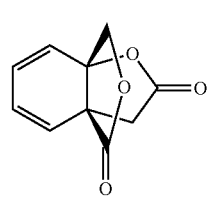

IIa or enantiomer thereof comprising converting a compound of formula Ic:

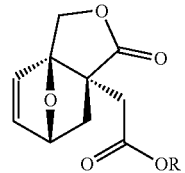

Ic or a salt thereof or an enantiomer or a salt thereof to the compound of formula IIa wherein R is H, $(C_1$-$C_6)$alkyl, or $(C_3$-$C_6)$cycloalkyl.

18. A method for preparing 2-methylstyrene comprising converting a compound of formula Id:

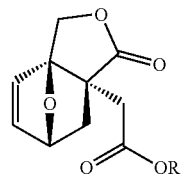

Id or a salt thereof or an enantiomer or a salt thereof to 2-methylstyrene, wherein R is H, $(C_1$-$C_6)$alkyl, or $(C_3$-$C_6)$ cycloalkyl.

19. A method for preparing a compound of claim 2 which is a compound of formula Id:

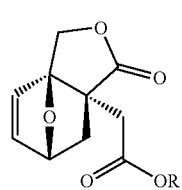
Id
or a salt thereof or an enantiomer or a salt thereof, comprising converting a compound of formula Ic:
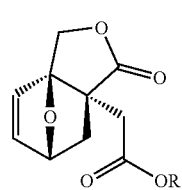
Ic
or a salt thereof or an enantiomer or a salt thereof to the compound of formula Id, wherein R is H, $(C_1-C_6)$alkyl, or $(C_3-C_6)$cycloalkyl.
* * * * *

UNITED STATES PATENT AND TRADEMARK OFFICE
CERTIFICATE OF CORRECTION

PATENT NO. : 10,047,100 B2
APPLICATION NO. : 15/474401
DATED : August 14, 2018
INVENTOR(S) : Thomas R. Hoye, Ashok Pehere and Shu Xu Page 1 of 2

It is certified that error appears in the above-identified patent and that said Letters Patent is hereby corrected as shown below:

In the Claims

Column 64, Lines 50-60, Claim 18, delete the following compound:

"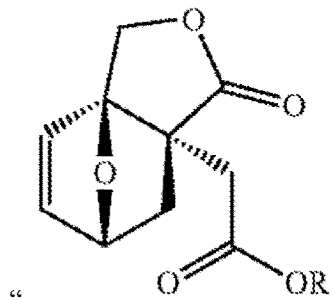"

And insert the following:

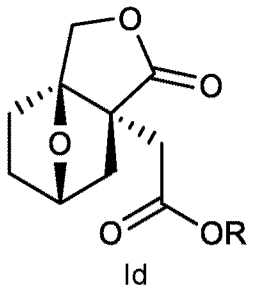

--    --;

Signed and Sealed this
Eighth Day of January, 2019

Andrei Iancu
*Director of the United States Patent and Trademark Office*

Column 65, Lines 1-10, Claim 19, delete the following compound:
" 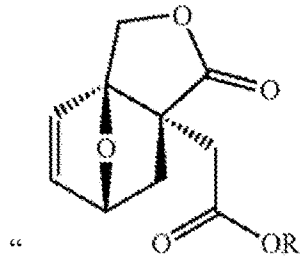 Id "
And insert the following:
-- 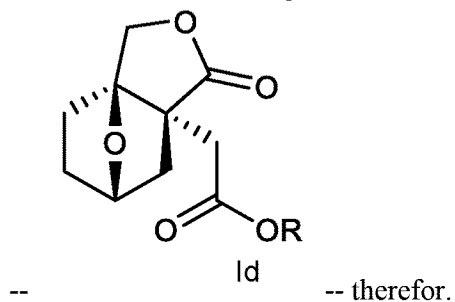 Id -- therefor.